United States Patent [19]

Wetzel et al.

[11] 4,388,315
[45] Jun. 14, 1983

[54] CEPHALOSPORINS

[75] Inventors: Bernd Wetzel; Eberhard Woitun; Roland Maier, all of Biberach an der Riss; Wolfgang Reuter, Laupertshausen; Uwe Lechner, Ummendorf; Hanns Goeth, Biberach an der Riss, all of Fed. Rep. of Germany

[73] Assignee: Boehringer Ingeleheim GmbH, Ingelheim am Rhein, Fed. Rep. of Germany

[21] Appl. No.: 307,117

[22] Filed: Sep. 30, 1981

Related U.S. Application Data

[62] Division of Ser. No. 151,694, May 20, 1980, Pat. No. 4,316,898.

[30] Foreign Application Priority Data

Jun. 21, 1979 [DE] Fed. Rep. of Germany ....... 2924948

[51] Int. Cl.³ ................. A61K 31/545; C07D 501/36
[52] U.S. Cl. ...................................... 424/246; 544/27
[58] Field of Search .......................... 544/27; 424/246

[56] References Cited
U.S. PATENT DOCUMENTS 4,015,000 3/1977 Kocsis et al. ...................... 544/36

Primary Examiner—Robert Gerstl
Attorney, Agent, or Firm—Hammond & Littell, Weissenberger & Muserlian

[57] ABSTRACT

Cephalosporins of the formula

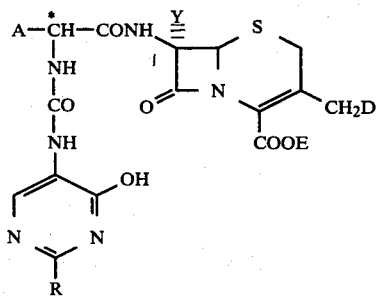

wherein
A is phenyl, 4-hydroxyphenyl, cyclohexyl, cyclohexene-1-yl, cyclohexa-1,4-diene-1-yl, 2-thienyl, 3-thienyl, 2-furyl, 3-furyl or 3,4-disubstituted phenyl, where the substituents, which may be identical to or different from each other, are each chlorine, hydroxyl or methoxy;
Y is hydrogen or methoxy;
D is hydrogen, hydroxyl, acetoxy, aminocarbonyloxy, pyridinium, aminocarbonyl-pyridinium or the group S-Het, where Het is 1-methyl-tetrazol-5-yl, tetrazol-5-yl, 3-methyl-1,2,4-thiadiazol-5-yl,1,2,4-thiadiazol-5-yl, 1,3,4-thiadiazol-5-yl, 2-methyl-1,3,4-thiadiazol-5-yl, 2-methylamino-1,3,4-thiadiazol-5-yl, 2-dimethylamino-1,3,4-thiadiazol-5-yl, 2-formylamino-1,3,4-thiadiazol-5-yl, 2-acetylamino-1,3,4-thiadiazol-5-yl, 2-methyl-1,3,4-oxadiazol-5-yl, 1,2,3-triazol-4-yl or 1,2,4-triazol-3-yl;
R is hydrogen, methyl, cyclopropyl, hydroxyl, methoxy, ethoxy, mercapto, morpholino, thiomorpholino, thiomorpholino-S-oxide, thiomorpholino-S,S-dioxide,

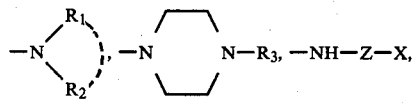

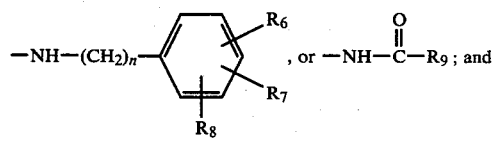

E is hydrogen or a protective group which is easily removable in vitro or in vivo;
and non-toxic, pharmacologically acceptable salts thereof.

24 Claims, No Drawings

CEPHALOSPORINS

This is a division of copending application Ser. No. 151,694, filed May 20, 1980, now U.S. Pat. No. 4,316,898, issued Feb. 23, 1982.

This invention relates to novel cephalosporins, to methods of preparing these compounds, to pharmaceutical compositions containing them as active ingredients, and to methods of using them as antibiotics.

More particularly, the present invention relates to a novel class of cephalosporins represented by the formula

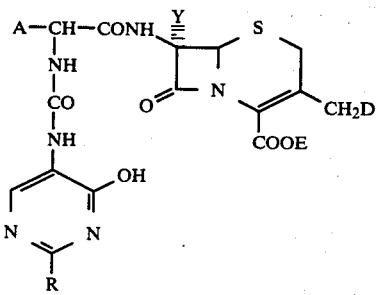

wherein

A is phenyl, 4-hydroxyphenyl, cyclohexyl, cyclohexene-1-yl, cyclohexa-1,4-diene-1-yl, 2-thienyl, 3-thienyl, 2-furyl, 3-furyl or 3,4-disubstituted phenyl, where the substituents, which may be identical to or different from each other, are each chlorine, hydroxyl or methoxy;

Y is hydrogen or methoxy;

D is hydrogen, hydroxyl, acetoxy, aminocarbonyloxy, pyridinium, aminocarbonyl-pyridinium or the group S-Het, where Het is 1-methyl-tetrazol-5-yl, tetrazol-5-yl, 3-methyl-1,2,4-thiadiazol-5-yl, 1,2,4-thiadiazol-5-yl, 1,3,4-thiadiazol-5-yl, 2-methyl-1,3,4-thiadiazol-5-yl, 2-methylamino-1,3,4-thiadiazol-5-yl, 2-dimethylamino-1,3,4-thiadiazol-5-yl, 2-formylamino-1,3,4-thiadiazol-5-yl, 2-acetylamino-1,3,4-thiadiazol-5-yl, 2-methyl-1,3,4,-oxadiazol-5-yl, 1,2,3-triazol-4-yl or 1,2,4-triazol-3-yl;

R is hydrogen, methyl, cyclopropyl, hydroxyl, methoxy, ethoxy, mercapto, morpholino, thiomorpholino, thiomorpholino-S-oxide, thiomorpholino-S,S-dioxide,

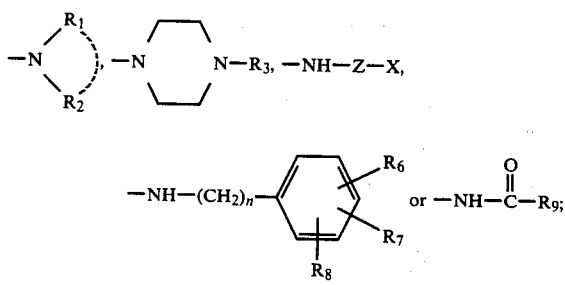

$R_1$ and $R_2$, which may be identical to or different from each other, are each hydrogen, straight or branched aliphatic hydrocarbyl of 1 to 6 carbon atoms, optionally containing one to two double bonds or a triple bond; cycloalkyl of 3 to 6 carbon atoms; or cycloalkyl-alkyl of 3 to 6 carbon atoms in the cycloalkyl moiety and 1 to 2 carbon atoms in the alkyl moiety;

$R_1$ and $R_2$, together with each other, form an alkylene chain of 2 to 7 carbon atoms and thus, together with the nitrogen atom to which they are attached, a 3- to 8-membered heterocyclic ring;

$R_3$ is formyl, acetyl or ethoxycarbonyl;

Z is straight or branched alkylene of 1 to 4 carbon atoms or cycloalkylene of 3 to 6 carbon atoms;

X is cyano, hydroxyl, mercapto, amino, aminocarbonyl, aminosulfonyl, aminocarbonylamino,

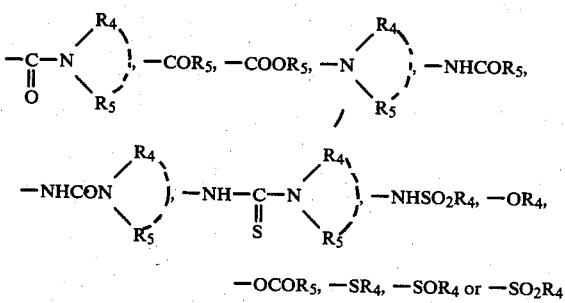

$-OCOR_5, -SR_4, -SOR_4$ or $-SO_2R_4$ $R_4$ is straight or branched alkyl of 1 to 3 carbon atoms;

$R_5$ is hydrogen or alkyl of 1 to 3 carbon atoms;

$R_4$ and $R_5$, together with each other and the nitrogen atoms to which they are attached, form a 3- to 6-membered heterocyclic ring optionally containing an additional ring nitrogen atom;

n is 0 or 1;

$R_6$, $R_7$ and $R_8$, which may be identical to or different from each other, are each hydrogen, halogen, amino, alkylamino, dialkylamino, hydroxy, alkoxy, formylamino, aliphatic acylamino, aminocarbonylamino, alkylaminocarbonylamino, dialkylaminocarbonylamino, nitro, alkylsulfonylamino, formyl, alkylcarbonyl, alkylcarbonyloxy, alkoxycarbonyl, alkoxycarbonyloxy, carboxyl, aminocarbonyl, alkylaminocarbonyl, dialkylaminocarbonyl, aminocarboxyl, alkylaminocarboxyl, dialkylaminocarboxyl, alkoxycarbonylamino, cyano, mercapto, alkylmercapto, alkylsulfinyl, alkylsulfonyl groups, aminosulfonyl, alkylaminosulfonyl, dialkylaminosulfonyl, hydroxysulfonyl, or straight or branched alkyl, whereby each alkyl moiety in these variants may contain 1 to 3 carbon atoms;

$R_9$ is hydrogen, alkyl of 1 to 4 carbon atoms, alkoxy of 1 to 3 carbon atoms, amino, methylamino or dimethylamino; and E is hydrogen or a protective group which is easily removable in vitro or in vivo, such as those which have heretofore been used in the field of penicillins and cephalosporins, especially ester-forming groups which can be removed under mild conditions by hydrogenation or hydrolysis or other treatments, or ester-forming groups which can easily be split off in the living organism;

and, when E is hydrogen, their non-toxic, pharmacologically acceptable salts thereof, such as their alkali metal or alkaline earth metal salts, especially the sodium, potassium, magnesium or calcium salts; their ammonium salts; or their organic amine salts, especially the triethylamine or dicyclohexylamine salts.

In vitro easily removable protective groups are, for example, benzyl, diphenylmethyl, trityl, tert. butyl, 2,2,2-trichloroethyl or trimethylsilyl.

In vivo easily removable protective groups are, for example, alkanoyloxyalkyl, such as acetoxymethyl, propionyloxymethyl, 2-acetoxyethyl or pivaloyloxymethyl, phthalidyl or indanyl.

When D is pyridinium or aminocarbonylpyridinium, the compounds of this invention have the formula

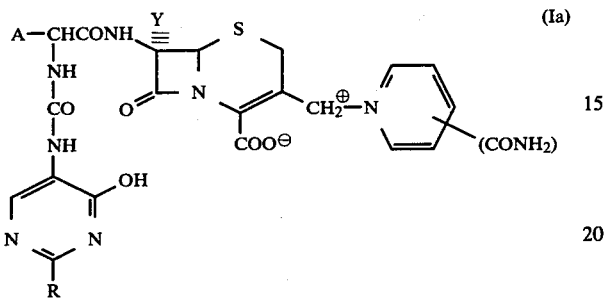

A preferred sub-genus is constituted by compounds of the formula I wherein

A is phenyl, p-hydroxyphenyl, 3,4-dihydroxyphenyl, 2-thienyl, 3-thienyl, 2-furyl or 3-furyl;

Y is hydrogen or methoxy;

D is hydrogen, hydroxyl, acetoxy; aminocarbonyloxy, pyridinium, 4-aminocarbonylpyridinium, -S-Het, where Het is 3-methyl-1,2,4-thiadiazol-5-yl, 1,2,4-thiadiazol-5-yl, 1,3,4-thiadiazol-2-yl, 2-methyl-1,3,4-thiadiazol-5-yl, 2-methylamino-1,3,4-thiadiazol-5-yl, 2-dimethylamino-1,3,4-thiadiazol-5-yl, 2-formylamino-1,3,4-thiadiazol-5-yl, 2-acetylamino-1,3,4-thiadiazol-5-yl, 1-methyl-tetrazol-5-yl, tetrazol-5-yl, 1,2,3-triazol-4-yl, 1,2,4-triazol-3-yl or 2-methyl-1,3,4-oxadiazol-5-yl;

R is hydrogen, cyclopropyl, hydroxyl, methoxy, formylamino, acetylamino, aminocarbonylamino,

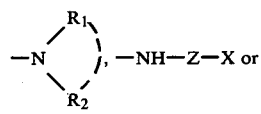

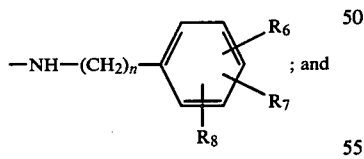

$R_1$, $R_2$, Z, X, $R_6$, $R_7$, $R_8$, n and E have the meanings previously defined;

and, when E is hydrogen, non-toxic, pharmacologically acceptable salts thereof.

An especially preferred sub-genus is constituted by compounds of the formula I wherein A is phenyl, p-hydroxyphenyl, 2-thienyl, 2-furyl or 3-furyl;

Y is hydrogen or methoxy;

E is hydrogen or pivaloyloxymethyl;

D is hydrogen, acetoxy, aminocarbonyloxy or S-Het, where

Het is tetrazol-5-yl, 1-methyl-tetrazol-5-yl, 1,3,4-thiadiazol-5-yl or 2-methyl-1,3,4-thiadiazol-5-yl;

R is hydrogen, cyclopropyl, hydroxyl, methoxy, dimethylamino, 4'-hydroxycyclohexyl-amino

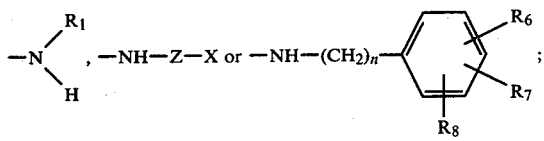

$R_1$ is hydrogen, saturated or unsaturated aliphatic hydrocarbyl of 1 to 4 carbon atoms, or cycloalkyl of 3 to 6 carbon atoms;

Z is ethylene or propylene;

X is hydroxyl, amino, methoxy, ethoxy, mercapto, aminocarbonyl, methylaminocarbonyl, dimethylaminocarbonyl, aminosulfonyl, methylaminosulfonyl, dimethylaminosulfonyl, aminocarbonylamino, methylaminocarbonylamino, methoxycarbonyl, ethoxycarbonyl, methylcarbonyl, ethylcarbonyl, methylmercapto, ethylmercapto, carboxy, methylamino, dimethylamino, formylamino, acetylamino, methylsulfonylamino, acetoxy, methylsulfinyl or methylsulfonyl;

n is 0 or 1; and one to two of $R_6$, $R_7$ and $R_8$ are hydrogen, chlorine, fluorine, methyl, ethyl, amino, methylamino, dimethylamino, hydroxyl, methoxy, ethoxy, nitro, formylamino, acetylamino, aminocarbonylamino, methylaminocarbonylamino, methylsulfinyl, methylsulfonyl, acetyl, methylcarbonyloxy, methoxycarbonyl, carboxyl, aminocarbonyl, methylaminocarbonyl, dimethylaminocarbonyl, cyano, methylmercapto, methylsulfonylamino, aminosulfonyl, methylaminosulfonyl, dimethylaminosulfonyl, ethylaminosulfonyl, and the remainder of $R_6$, $R_7$ and $R_8$ are hydrogen;

and, when E is hydrogen, non-toxic, pharmacologically acceptable salts thereof.

A further especially preferred sub-genus is constituted by compounds of the formula I wherein R is

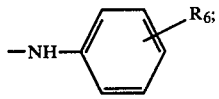

$R_6$ is hydrogen, chlorine, hydroxyl, nitro, acetylamino, methylsulfinyl, methylsulfonyl acetyl, aminocarbonyl, aminocarbonylamino, methylsulfonylamino, aminosulfonyl, methylaminosulfonyl, dimethylaminosulfonyl or ethylaminosulfonyl; and A, Y, D and E have the same meanings as page 6, lines 18–26, and, when E is hydrogen, non-toxic pharmacologically acceptable salts thereof.

The cephalosporin compounds of the formula I exist in two tautomeric forms, that is, the lactim and the lactam form. Which of the two forms I or I' is predominant, depends particularly on the respective solvent and on the type of substituent R:

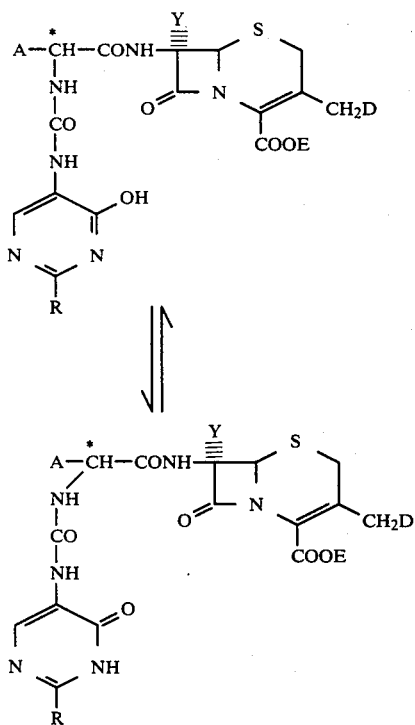

(I)

(I')

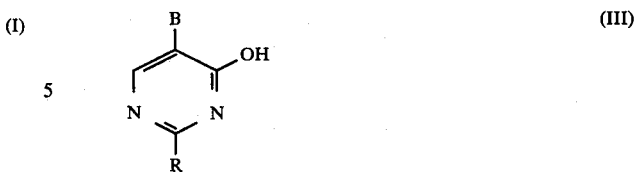

(III)

wherein
R has the meanings previously defined, and
B is =NCO or a reactive derivative of —NHCOOH, such as —NHCOCl, —NHCOBr or

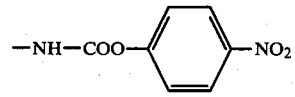

where =NCO and —NHCOCl are especially preferred.

Also mixtures of such pyrimidine derivatives of the formula III can be used, wherein B has partly the one and partly the other of the above-mentioned meanings, for instance =NCO and —NHCOCl simultaneously.

If E is a hydrogen, the starting compounds of the formula II can be used in form of their inorganic or organic salts, for instance as the triethylammonium salts or the sodium salts. In that case the reaction can be carried out in any desired mixtures of water and those organic solvents which are miscible with water such as ketones, for example acetone; cyclic ethers, for example tetrahydrofuran or dioxane; nitriles, for example acetonitril; formamides, for example dimethylformamide; dimethylsulfoxide; or alcohols, for example isopropanol; or in hexametapol. By addition of a base or by use of a buffer solution, the pH of the reaction mixture is kept in a pH range of about 2.0 to 9.0, preferably between pH 6.5 and 8.0. However, it is also possible to carry out the reaction in an anhydrous organic solvent, such as halogenated hydrocarbons like chloroform or methylene chloride, in the presence of a base, preferably triethylamine, diethylamine or N-ethylpiperidine.

The reaction can further be carried out in a mixture of water and a water-immiscible solvent, such as an ether, for example diethyl ether; a halogenated hydrocarbon, for example chloroform or methylene chloride; carbon disulfide; ketone, for example isobutylmethyl ketone; an ester, for example ethyl acetate; or an aromatic solvent, for example benzene, where it is advantageous to stir vigorously and to keep the pH value in a range of about pH 2.0 to 9.0, preferably between 6.5 and 8.0, by addition of a base or by use of a buffer solution. The reaction can be carried out, however, also in water alone in the presence of an organic or inorganic base or of a buffer substance.

If E is trimethylsilyl, that is, if a silyl derivative of a compound of the formula II, such as a mono- or, more advantageously, a di-trimethylsilyl derivative silylated at the amino and carboxyl group, is used as the starting compound, and it is reacted with a compound of the formula III, the reaction is generally advantageously carried out in an anhydrous solvent or a solvent free from hydroxyl groups, for example in a halogenated hydrocarbon, such as methylene chloride or chloroform, benzene, tetrahydrofuran, acetone or dimethylformamide, etc. The addition of a base is not essential, It goes without saying that the compounds of the formula I referred to above always comprise both tautomeric forms.

With regard to the chiral centre C, the compounds of the formula I may be present in two possible R- and S-configurations or as mixtures of these. Particularly preferred are those compounds which have the D=R configuration. If the end product is obtained in the D,L-form, the pure D- and L-diasteroisomers can be separated by preparative high pressure liquid chromatography (HPLC).

The compounds of the formula I may be prepared by the following methods.

Method A

For the preparation of a compound of the formula I wherein D has the meanings previously defined with the exception of pyridinium or aminocarbonylpyridinium, by reacting a compound of the formula

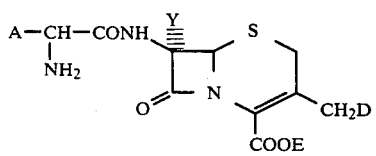

(II)

wherein
A, Y and E have the meanings previously defined, and
D has the meanings previously defined with the exception of pyridinium or aminocarbonylpyridinium, with a pyrimidine derivative of the formula but may be of advantage in individual cases to improve the yield or the purity of the end product. Examples of such bases are tertiary aliphatic or aromatic amines, such as pyridine or triethylamine, or by steric hindrance difficulty acylatable secondary amines, such as dicyclohexylamine.

If E is one of the above-mentioned in vitro or in vivo easily removable protective groups, such as diphenylmethyl or pivaloyloxymethyl, it is of advantage to perform it in an aprotic solvent, such as absolute methylene chloride, chloroform, tetrahydrofuran or dimethylformamide.

The amount of base to be used is determined, for example, by the desired maintenance of a certain pH value.

Where no pH measurement or adjustment is made or where no measurement is possible or practical because of a lack of sufficient water in the diluting agent, 1.0 to 2.0 mol-equivalents of base are used when silylated compounds of the formula II are not present. When such silylated compounds are present, preferably up to one molequivalent of base is used.

In general, all organic and inorganic bases which are usually used in organic chemistry, can be used as base additives. Such bases may be alkali metal and alkaline earth metal hydroxides, alkaline earth metal oxides, alkali metal and alkaline earth metal carbonates and bicarbonates, ammonia, primary, secondary and tertiary aliphatic and aromatic amines, as well as heterocyclic bases. Preferred bases are sodium, potassium and calcium hydroxide, calcium oxide, sodium and potassium carbonate, sodium and potassium bicarbonate, ethylamine, methylethylamine, triethylamine, hydroxyethylamine, aniline, dimethylaniline, pyridine and piperidine. When using silylated starting compounds, however, the above-mentioned restrictions concerning the kind of base should be considered.

Suitable buffer system include all the usual buffer mixtures, such as phosphate buffer, citrate buffer and tris-(hydroxymethyl)-amino-methane buffer.

The reaction temperatures can be varied over a wide range. In general, the reaction is carried out between −20° and +50° C., preferably between 0° and +20° C.

The reaction partners of the formulas II and III can be reacted with each other in equimolar quantities. However, in some cases it may be advantageous to use one of the reaction partners in excess to facilitate the purification of the end product or to increase the yield.

Method B

For the preparation of a compound of the formula I wherein D has the meanings previously defined with the exception of pyridinium or aminocarbonylpyrimidinium, by reacting a ureidocarboxylic acid of the formula

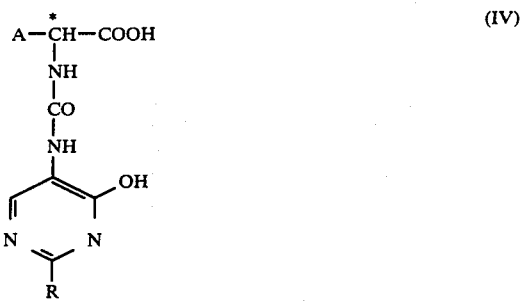

wherein A and R have the meanings previously defined, or a salt or reactive derivative thereof, with a 7-aminocephalosporanic acid derivative of the formula

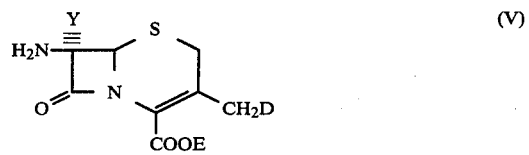

wherein E and Y have the meanings previously defined, and D has the meanings previously defined with the exception of pyridinium and aminocarbonylpyrimidinium.

Suitable reactive derivatives of the ureidocarboxylic acids of the formula IV include, for example, their acid anhydrides such as those derived from chloroformates, for instance ethyl or isobutyl chloroformate, or their reactive esters such as the p-nitrophenyl ester or the N-hydroxysuccinimide ester, or their reactive amides such as the N-carbonyl-imidazole, but also their acid halides such as the corresponding acid chloride or their acid azides.

In general, however, all methods of bonding which are known in β-lactam chemistry can be used.

The 7-aminocephalosporanic acid derivative is advantageously reacted in the form of an in vitro or in vivo easily cleavable derivative. For example, the compounds of the formula V wherein E has the above-mentioned meanings, with the exception of hydrogen, are suitable; especially preferred derivatives are the diphenylmethyl ester, the tert. butyl ester, the trimethylsilyl ester or the N,O-bistrimethylsilyl derivative.

For example, the ureidocarboxylic acid or a salt or reactive derivative thereof is reacted with the 7-aminocephalosporanic acid derivative in a solvent at temperatures between −40° C. and +40° C., optionally in the presence of a base. If, for example, an anhydride of the ureidocarboxylic acid, such as the anhydride with ethylchloroformate, is used, the reaction is carried out while cooling, for instance at −10° C. to +10° C., in the presence of a tertiary amine such as triethylamine or N,N-dimethylaniline, in a solvent such as acetone, tetrahydrofuran, dimethylformamide, chloroform, dichloromethane, hexametapol, or a mixture of these solvents. If, for example, an N-hydroxysuccinimide ester of the ureidocarboxylic acid is reacted with a derivative of the formula V, the reaction is preferably carried out at 0° to 20° C. in the presence of a base such as triethylamine, in a solvent such as dimethylformamide, dichloromethane, dioxane, or a mixture of such solvents.

The reaction of ureidocarboxylic acid of the formula IV or a salt thereof with a compound of the formula V is advantageously carried out in the presence of a condensation agent, for instance in the presence of N,N'-dicyclohexylcarbodiimide.

Method C

A compound of the formula I wherein D is either —S-Het, where Het has the meanings previously defined, pyridinium or aminocarbonylpyridinium, and E is hydrogen, can be prepared by reacting a compound of the formula

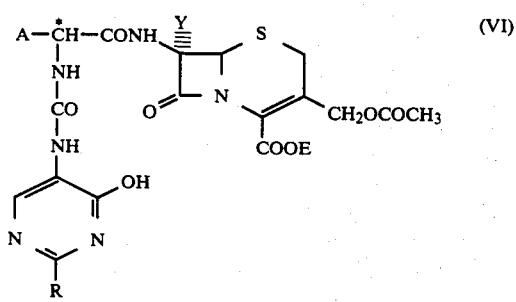

wherein

A, R and Y have the meanings previously defined, and

E is hydrogen, either with a compound of the formula

Het-S-N    (VII)

wherein

Het has the meanings previously defined, and

M is hydrogen, an alkali metal or an alkaline earth metal, or with pyridine or 4-aminocarbonyl-pyridine.

A compound of the formula I, wherein D is —SHet, pyridinium or 4-aminocarbonylpyridinium, and E is hydrogen, is obtained. For Example, a compound of the formula VI is reacted with 5-methyl-2-mercapto-1,3,4-thiadiazole in a solvent such as water, methanol, ethanol, acetone, methyl ethyl ketone, tetrahydrofuran, acetonitrile, ethyl acetate, dimethoxyethane, dimethylformamide, dimethyl sulfoxide, chloroform or a mixture of these solvents. Preferably, a strong polar solvent such as water or the like is used. In this case the pH of the reaction solution is advantageously maintained between 2 and 10, and particularly between 4 and 8. The desired pH value can be adjusted by addition of a buffer solution, such as sodium phosphate. The reaction conditions are not subject to special restrictions. Normally, the reaction is carried out at a temperature in a range of 0° to 100° C., over a reaction time of several hours.

Method D

A compound of the formula I wherein Y is methoxy can be obtained by reacting a compound of the formula I wherein Y is hydrogen, in the presence of methanol with an alkali metal methylate of the formula M+OCH3−, where M+ is an alkali metal, and then with a halogenating agent. For this purpose, a cephalosporin of the formula I wherein Y is hydrogen is dissolved or suspended in an inert solvent, such as tetrahydrofuran, dioxane, ethyleneglycol dimethylether, methylene chloride, chloroform, dimethyl formamide, methanol or the like or in a mixture of two of these solvents.

An alkali metal methylate together with methanol is added to the obtained solution or suspension. The obtained mixture is caused to react, and the reaction mixture is then reacted with a halogenating agent. In this reaction methanol is used in excess, and the quantity of the alkali metal methylate is preferably 2 to 6 equivalents per equivalent of cephalosporin. "Excess" means an amount of more than one equivalent per equivalent of cephalosporin. All reactions are carried out at temperatures between −120° and −10° C., and preferably between −100° and −50° C. A reaction time of 5 to 30 minutes is sufficient. The reaction is terminated by acidifying the reaction system.

The halogenating agent used in this process is generally known as source for postive halogen atoms, such as Cl+, Br+ or I+. Examples of such halogenating agents are halogens, such as chlorine, bromine, etc; N-haloimides, such as N-chloro-succinimide, N-bromo-succinimide, and the like; N-halo-imides, such as N-chloroacetamide, N-bromoacetamide, etc; N-halo-sulfonamides, such as N-chloro-benzenesulfonamide, N-chloro-p-toluenesulfonamide, etc.; 1-halo-benzotriazoles; 1-halo-triazines; organic hypohalites, such as tert. butylhypochlorite, tert. butylhypoiodite, etc.; and halo-hydantoins, such as N,N-dibromohydantoin, etc. Tert. butylhypochlorite is preferred among these halogenating agents. The halogenating agent is used in a quantity sufficient to produce an equivalent quantity of positive halogen atoms with regard to the amount of cephalosporing of the formula VI.

Suitable acids for termination of the reaction are those which do not lead to solidification of the reaction mixture or to freezing of the reaction mixture into a heavy viscous mass when they are added to the cold reaction mixture. Suitable acids are, for example, 98% formic acid, glacial acetic acid, trichloroacetic acid or methane sulfonic acid.

After the interruption of the reaction the excess halogenating agent is removed by treatment with a reducing agent, such as trialkyl phosphite, sodium thiosulfate or the like.

The compounds prepared according to methods A, B and D, wherein E is an in vitro easily removable protective group, can be converted according to known methods in cephalosporin chemistry into the free carboxylic acids of the formula I wherein E is hydrogen. Thus, the trimethylsilyl group can, for example, be easily removed by aqueous hydrolysis, and the benzhydryl group can be removed, for example, by hydrolytic cleavage with trifluoroacetic acid. This elimination of the protective groups is known from the literature.

Moreover, the cephalosporin antibiotics of the formula I wherein E is hydrogen can be converted into the acyloxyalkyl esters, wherein E is, for example, a pivaloyloxymethyl radical

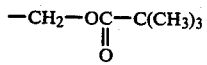

by reacting an alkali metal salt of the cephalosporin carboxylic acid, for example a sodium or potassium salt, with a pivaloyloxymethyl halide of the formula

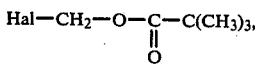

wherein Hal is chlorine, bromine or iodine.

Further suitable acyloxyalkyl halides are, for example, chloromethyl acetate, bromomethylpropionate or 1-bromoethyl acetate.

The preparation of an acyloxyalkyl ester of the formula I is carried out by reacting the respective alkali metal salt of the parent acid in an inert solvent with a slight molar excess of the iodine, bromine or chloroalkyl ester, such as pivaloyloxymethyl iodide, at room temperature or slightly elevated temperature up to about 40° to 45° C. Suitable solvents are, for example, acetone, tetrahydrofuran, dioxane, dimethylformamide or methylene chloride.

An indanyl ester of the formula I, wherein E is

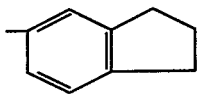

can be prepared by reacting 5-indanol in an inert solvent, such as dioxane or tetrahydrofuran, with the free acid form of a compound of the formula I, wherein E is hydrogen, in the presence of a condensation agent, for example a diimide such as dicyclohexyl carbodiimide. The reaction is carried out while stirring at a temperature of about 20° to 35° C. during a reaction time of about 6 to 8 hours. For the isolation of the indanyl ester, the reaction mixture is first diluted with water, and the insoluble dicyclohexylurea is filtered off from the reaction mixture. Then, the ester is extracted from the filtrate.

The indanyl esters can also be prepared by reacting an anhydride, formed from a cephalosporanic acid of the formula I and acetic acid, with 5-indanol.

A phthalidyl ester of the formula I, wherein $R_3$ is

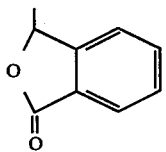

can be prepared by reacting the bromophthalide of formula

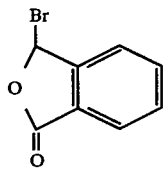

with a salt of a cephalosporanic acid of the formula I. The esterification can be effected by slowly heating a mixture of equimolar amounts of the cephalosporin salt, such as the sodium or potassium salt, and bromophthalide in dimethylformamide, dimethylacetamide, dioxane, tetrahydrofuran or mixtures thereof.

After the reaction has gone to completion, the reaction mixtures obtained according to methods A–D are further processed by conventional methods for β-lactam antibiotics. The same is the case concerning the isolation and purification of the end products, for instance concerning the liberation of the acid to form other salts with inorganic or organic bases. Especially suitable for the preparation of potassium or sodium salts is the precipitation of these salts from an alcoholic-ethereal solution of a free acid by addition of potassium or sodium 2-ethylhexanoate, or the reaction of a free acid with the corresponding quantity of sodium bicarbonate under pH control and subsequent freeze-drying.

Typical starting compounds of the formula II, wherein A is phenyl, substituted phenyl or thienyl, and D is 1-methyl-1H-tetrazol-5-yl or 2-methyl-1,3,4-thiadiazol-5-yl, are known from the literature; see, for example, U.S. Pat. No. 3,641,021. Starting compounds of the formula II, wherein A is furyl, thienyl, hydrogen or methoxy, are described, for example, in J. Antibiotics 31, page 546, and page 560 (1978). The starting compounds of the formula V are also known from the literature. For example, 7-aminocephalosporanic acid systems wherein D has the meaning of a heterocyclic system can be obtained by reacting 7-aminocephalosporanic acid with the corresponding mercaptoheterocycle in conventional manner.

The starting compounds of the formula III can be obtained, for example, by reacting a corresponding 5-aminopyrimidine of the formula

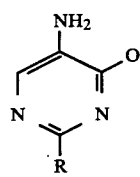

(VIII)

wherein R has the meanings previously defined, with phosgene. This reaction is preferably carried out in a solvent which does not contain hydroxyl groups, such as tetrahydrofuran, methylene chloride, chloroform, dimethoxyethane or hexametapol, at temperatures between −40° and +60° C., preferably between −10° and +20° C. It is recommended to neutralize the hydrogen chloride released by the reaction with equimolar quantities of an inert organic base, such as triethylamine or pyridine. Also, pyridine in excess can be used as the solvent. If the particular aminopyrimidine of the formula VIII is difficultly soluble in one of the mentioned solvents, the phosgenation can also be carried out in a heterogeneous system. In an especially preferred manner, the aminopyrimidine of the formula VIII can be converted by treatment with a silylating agent, such as hexamethyldisilazane, trimethyl chlorosilane/triethylamine, trimethylsilyl diethylamine or N,O-bis-trimethylsilyl acetamide, into an aminopyrimidine which, in general, is very easily soluble in the mentioned solvents and which is, depending on the number of exchangeable hydrogen atoms, mono- or poly-silylated. After addition of phosgene, the aminopyrimidine reacts with the corresponding compound of the formula III, where the reaction is preferably carried out without the addition of a base.

Depending on the kind of solvent, the temperature, the amount and kind of base which is optionally added, either mainly the corresponding isocyanate of the carbamic acid halide or a mixture of these two compounds is obtained. Depending on the conditions, the isocyanate of the formula III can also be present as a dihydrooxazole-pyrimidine of the formula IIIa, this compound being isomeric with the isocyanate.

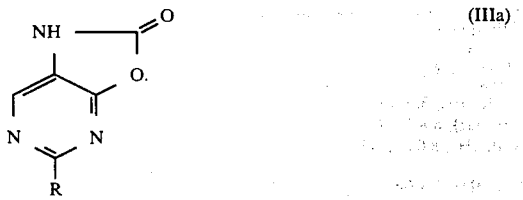

Depending on the kind of the substituent R, the isocyanate of the formula VI may also be present as a mono- or poly-silylated analog.

The starting compounds of the formula III or IIIa or mixtures thereof or silylated analogs thereof obtained by phosgenation, as described above, are in general readily soluble in the above-mentioned solvents, and after removal of excess phosgene they can be reacted directly without further purification with the corresponding cephalosporin derivative of the formula II.

However, it is also possible to isolate the intermediate product of the formula IIIa, de-silylate the intermediate, optionally with a protic solvent such as water or methanol, or, based on the properties of solubility, to purify it or react it in the manner mentioned above.

The syntheses for 2-substituted 5-amino-4-hydroxypyrimidines of the formula VIII are described in the German Offenlegungsschriften Nos. 2,808,153 and 2,910,190.

The ureidocarboxylic acids of the formula IV can be easily obtained by reacting a pyrimidine derivative of the formula III with a glycine derivative of the formula

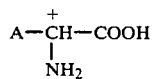

wherein A has the meanings previously defined. The reaction is carried out at temperatures between $-20°$ and $+40°$ C., preferably between $0°$ and $+20°$ C., in a solvent. Suitable solvents are, for example, mixtures of water and organic solvents which are miscible with water, such as acetone, tetrahydrofuran, dioxane, acetonitrile, dimethylformamide, ethanol or dimethylsulfoxide, optionally in the presence of a hydrogen-halide-binding agent. Suitable representatives thereof are, for example, trialkylamines such as triethylamine, or inorganic bases such as dilute sodium hydroxide solution.

The following examples illustrate the present invention and will enable others skilled in the art to understand it more completely. It should be understood, however, that the invention is not limited solely to the particular examples given below.

EXAMPLE 1

Preparation of ureidocarboxylic acids of the formula IV (a) D-α-(2-Cyclopropyl-4-hydroxy-2-pyrimidinyl)-ureido-p-hydroxyphenyl-acetic acid 1.8 gm of 5-amino-2-cyclopropyl-4-hydroxy-pyrimidine (0.012 mol) were dissolved in 80 ml of absolute tetrahydrofuran and admixed with 1.65 ml of triethylamine. This solution was added dropwise at $0°$ C. to a solution of 1.20 gm of phosgene in 25 ml of tetrahydrofuran and the resulting mixture was stirred for 10 minutes while cooling with ice. Subsequently, nitrogen was blown through the solution to remove unreacted phosgene. A suspension of 2.0 gm (0.012 mol) of D-α-amino-p-hydroxyphenyl-acetic acid in 50 ml of tetrahydrofuran and 20 ml of water was caused to form a solution by addition of 12 ml of 1 N sodium hydroxide while cooling and stirring. The above prepared suspension was added dropwise to this solution while cooling with ice and keeping the pH between 8.0 and 8.5 with 1 N sodium hydroxide. The reaction mixture was stirred for one hour at $5°$ C. and for two hours at room temperature. After removing the tetrahydrofuran in vacuo, the residual solution was extracted twice with ethyl acetate at a pH of 8.0–8.5. The aqueous phase was then covered with 200 ml of ethyl acetate and was adjusted to pH 1.5 by adding dilute hydrochloric acid while cooling and stirring. The organic layer was separated, and the aqueous phase was again extracted with 50 ml of ethyl acetate. The organic phases were combined, dried over sodium sulfate, and the solvent was removed in vacuo.

Yield: 3.0 gm (73%).

IR spectrum: 3320 (broad), 1650, 1550 cm$^{-1}$; NMR spectrum: (CDCl$_3$+D$_2$O) signals at ppm: 1.15 (m, 4H), 1.9 (m, 1H), 5.45 (s, 1H), 6.9 (d, 2H), 7.45 (d, 2H), 8.6 (s, 1H).

The ureidocarboxylic acids of the formula

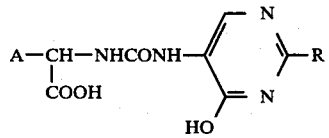

shown in the following table were synthesized in analogous manner:

TABLE I

| | A | R | Yield % | IR-spectrum cm$^{-1}$ | NMR-spectrum signals at ppm (DMSO + CD$_3$OD) |
|---|---|---|---|---|---|
| (b) | ⟨thienyl⟩ D,L | ▷– | 64.5 | 3360 (broad), 1670, 1560 | 1.10 (m, 4H), 1.95 (m, 1H), 5.5 (s, 1H), 7.0 (m, 2H) 7.4 (d, 1H), 8.55 (s, 1H) |
| (c) | ⟨furyl⟩ D,L | ▷– | 62 | 3350 (broad), 1650, 1570 | 1.05 (m, 4H), 1.90 (m, 1H), 5.45 (s, 1H), 6.4 (m, 2H), 7.65 (s, 1H), 8.50 (s, 1H) |
| (d) | HO–⟨phenyl⟩– | NHC$_3$H$_7$ | 71 | 3300 (broad), 1680, 1620, 1530 | 0.9 (t, 3H), 1.5 (m, 2H), 3.2 (m, 2H), 5.05 (s, 1H), 6.7 (d, 2H), 7.15 (d, 2H), 8.0 (s, 1H) |

TABLE I-continued

| | A | R | Yield % | IR-spectrum cm$^{-1}$ | NMR-spectrum signals at ppm (DMSO + CD$_3$OD) |
|---|---|---|---|---|---|
| (e) |  | NHCH(CH$_3$)$_2$ | 66 | 3350, 1650, 1560 | 1.15 (d, 6H), 3.9 (m, 1H), 5.1 (s, 1H), 6.8 (d, 2H), 7.3 (d, 2H), 8.05 (s, 1H) |
| (f) |  | NHC$_3$H$_7$ | 49 | 3350, 1670, 1570 | 1.0 (t, 3H), 1.6 (m, 2H), 3.2 (m, 2H), 5.4 (s, 1H), 6.4 (m, 2H), 7.6 (s, 1H), 8.05 (s, 1H) |
| (g) |  | NHCH$_2$CH=CH$_2$ | 54 | 3350, 1665, 1575 | 3.75 (broad 2H), 4.65 (broad, 2H), 5.05 (s, 1H), 5.4 (m, 1H), 6.80 (2H), 7.3 (2H), 8.1 (1H) |
| (h) |  | NHC$_3$H$_7$ | 52 | 3370, 1675, 1550 | 0.9 (t, 3H), 1.55 (m, 2H), 3.2 (m, 2H), 5.5 (s, 1H), 7.0 (m, 2H), 7.4 (d, 1H), 8.0 (s, 1H) |
| (i) |  | N(CH$_3$)$_2$ | 72 | 3350, 1670, 1560 | 3.0 (s, 6H), 5.1 (s, 1H), 6.75 (d, 2H), 7.2 (d, 2H), 8.0 (s, 1H) |
| (j) |  | NHCH$_2$CH(CH$_3$)$_2$ | 63.5 | 3300, 1670, 1565 | 0.85 (d, 6H), 1.8 (m, 1H), 3.1 (m, 2H), 5.0 (s, 1H), 6.75 (d, 2H), 7.2 (d, 2H), 8.0 (s, 1H) |
| (k) |  | NHCH$_2$CH=CHCH$_3$ | 66 | 3370 (broad), 1680, 1565 | 1.65 (d, 3H), 3.75 (broad), 5.1 (s, 1H), 5.4 (m, 2H), 6.8 (d, 2H), 7.3 (d, 2H), 8.05 (s, 1H) |
| (l) |  | NHCH$_2$C(CH$_3$)=CH$_2$ | 71 | 3350, 1670, 1560 | 1.75 (s, 3H), 3.75 (s, 2H), 4.7 (broad, 2H), 5.1 (s, 1H), 6.85 (2H), 7.3 (2H), 8.1 (1H) |
| (m) |  | NHCH$_2$C(CH$_3$)=CH$_2$ | 44 | 3380, 1650, 1550 | 1.70 (s, 3H), 3.80 (s, 2H), 4.75 (broad, 2H), 5.25 (s, 1H), 6.9 (m, 2H), 7.3 (1H), 8.05 (1H) |
| (n) |  | —NH— | 80 | 3800, 2950, 1660, 1520 | 1.6 (m, 8H), 4.1 (m, 1H), 5.2 (s, 1H), 6.85 (d, 2H), 7.3 (d, 2H), 8.1 (s, 1H) |
| (o) |  | —NH— | 72 | 3350 (broad), 1660, 1540 | 1.65 (m, 10H), 4.05 (m, 1H), 5.45 (s, 1H), 7.0 (m, 2H), 7.4 (d, 1H), 8.05 (s, 1H) |
| (p) |  | NH— | 67.5 | 3370 (broad), 1665, 1545 | 1.70 (m, 10H), 4.0 (m, 1H), 5.1 (s, 1H), 6.8 (d, 2H), 7.35 (d, 2H), 8.05 (s, 1H) |
| (q) | HO—⟨⟩— | NH—CH$_2$—◁ | 58 | 3350 (broad), 1670, 1610, 1540, 1520 | (CDCl$_3$/CD$_3$OD) 0.3 (m, 2H), 0.6 (m, 2H), 1.1 (m, 1H), 3.1 (d, 2H), 5.25 (s, 1H), 6.75 (d, 2H), 7.2 (d, 2H), 8.0 (s, 1H) |
| (r) | ⟨S⟩— | NH—⟨⟩ | 71 | 3360 (broad), 1665, 1600, 1540 | 1.65 (m, 8H), 4.05 (m, 1H), 5.5 (s, 1H), 7.0 (m, 2H), 7.4 (d, 1H), 8.05 (s, 1H) |
| (s) | HO—⟨⟩— | NH—⟨⟩ | 66.5 | 3350, 1660, 1600, 1535 | 5.15 (s, 1H), 6.8 (d, 2H), 7.35 (m, 7H), 8.35 (s, 1H) |

(t) D-α-(4-hydroxy-2-(4'-hydroxycyclohexylamino-5-pyrimidinyl)-ureido-p-hydroxy-phenyl-acetic acid 2.24 gm (0.01 mol) of 5-amino-4-hydroxy-2-(4'-hydroxycyclohexylamino)-pyrimidine were heated together with 7.5 gm of trimethylsilyldiethylamine at 80° C. for 10 minutes. The reaction mixture was evaporated to dryness in vacuo, and the solid residue was dissolved in 60 ml of dry tetrahydrofuran in a nitrogen atmosphere. This solution was added dropwise, while cooling with ice, to 1.05 gm of phosgene dissolved in 50 ml of tetrahydrofuran. After stirring for 5 minutes at room temperature, the reaction mixture was evaporated in vacuo to about half of its volume. The further reaction with 1.7 gm of p-hydroxyphenyl glycine was carried out analogous to Example 1(a).

The further processing, however, was carried out as follows: The aqueous phase was extracted twice at pH 7.0 with ethyl acetate and acidified with 2 N hydrochloric acid to pH 3.0, while cooling with ice. The precipitated product was suction-filtered off and dried.

Yield: 1.84 gm (44%).

IR-spectrum: 3400 (broad), 1670, 1550 cm$^{-1}$, NMR-spectrum (DMSO+CD$_3$OD) signals at ppm: 1.8 (m, 8H), 3.8 (m, 2H), 5.1 (s, 1H), 6.8 (d, 2H), 7.3 (d, 2H), 8.0 (S, 1H).

The ureidocarboxylic acids of the formula IV shown in the following table were synthesized in analogous manner:

TABLE II

| | A | R | Yield % | IR-spectrum cm$^{-1}$ | NMR-spectrum Signals at ppm (DMSO + CD$_3$OD) |
|---|---|---|---|---|---|
| (u) | furan-2-yl (D,L), O | NH—⟨cyclohexyl⟩—OH | 41 | 3380 (broad), 1660, 1560 | 1.75 (m,8H), 3.6-4-1 (m,1 + 1H), 5.5 (s,1H), 6.4 (m,2H), 7.65 (s,1H), 8.0 (s,1H) |
| (v) | thiophen-2-yl (D,L), S | NH—⟨cyclohexyl⟩—OH | 47 | 3360 (broad), 1670, 1570 | 1.80 (m,8H), 3.55-4-1 (m,1 + 1H), 5.45 (s,1H), 7.0 (m,2H), 7.4 (d,1H), 8.05 (s,1H) |
| (w) | HO—⟨phenyl⟩— | NH—CH$_2$CH$_2$SC$_2$H$_5$ | 61 | 3350 (broad), 1660, 1540 | 1.3 (t,3H), 2.7 (m,4H), 3.4 (m,2H), 5.1 (s,1H), 6.8 (d,2H), 7.2 (d,2H), 8.1 (s,1H) |
| (x) | HO—⟨phenyl⟩— | NHCH$_2$CH$_2$OCH$_3$ | 56 | 3320, 1670, 1550, 1515 | 3.0–3.6 (4H,m), 3.5 (3H,s), 5.2 (s,1H), 6.8 (d,2H), 7.3 (d,2H) 8.15 (s,1H) |
| (y) | furan-2-yl (D,L), O | NH(CH$_2$)$_3$OH | 42 | 3350, 1660, 1550 | 1.85 (m,2H), 3.3 (m,2H), 3.6 (m,2H), 5.4 (s,1H), 6.45 (m,2H), 7.6 (s,1H), 8.05 (s,1H) |
| (z) | HO—⟨phenyl⟩— | NH(CH$_2$)$_3$OH | 51 | 3340, 1650, 1570 | 1.85 (m,2H), 3.3 (m,2H), 3.65 (m,2H), 5.15 (s,1H), 6.8 (d,2H), 7.3 (d,2H), 8.05 (s,1H) |
| (aa) | thiophen-2-yl (D,L), S | NH(CH$_2$)$_3$OH | 44 | 3320, 1640, 1530 | 1.90 (m,2H), 3.3 (m,2H), 3.65 (m,2H), 5.5 (s,1H), 7.0 (m,2H), 7.4 (d,1H), 8.05 (s,1H) |
| (ab) | HO—⟨phenyl⟩— | NH(CH$_2$)$_3$SO$_2$NH$_2$ | 56 | 3340, 1635, 1540 | 2.0 (m,2H), 2.7 (m,2H), 3.40 (m,2H), 5.15 (s,1H), 6.8 (d,2H), 7.3 (d,2H), 8.10 (s,1H) |
| (ac) | HO—⟨phenyl⟩— | NH(CH$_2$)$_3$CONH$_2$ | 51.5 | 3800, 1630, 1580, 1530 | 1.9 (t,2H), 2.5 (m,2H), 3.45 (m,2H), 5.15 (s,1H), 6.8 (d,2H), 7.35 (d,2H), 8.10 (s,1H) |
| (ad) | thiophen-2-yl (D,L), S | NH(CH$_2$)$_3$SO$_2$NH$_2$ | 54 | 3330, 1640, 1545 | 1.95 (t,2H), 2.8 (m,2H), 3.35 (m,2H) 5.45 (s,broad, 1H), 7.05 (m,2H) 7.4 (m,2H), 7.4 (d,1H), 8.05 (s,1H) |
| (ae) | HO—⟨phenyl⟩— | NH(CH$_2$)$_2$NHCOCH$_3$ | 38 | 3320, 1635, 1575, 1525 | 2.2 (s,3H), 2.7 (m,2H), 3.3 (m,2H), 5.10 (s,1H), 6.85 (d,2H), 7.35 (d,2H), 8.10 (s,1H) |
| (af) | HO—⟨phenyl⟩— | NH—⟨phenyl⟩—Cl | 71 | 3330, 1645, 1540 | 5.15 (s,1H), 6.8 (d,2H), 7.3 (m,2 + 2H), 7.7 (d,2H), 8.3 (s,1H) |
| (ag) | furan-2-yl (D,L), O | NH—⟨phenyl⟩—Cl | 65 | 3350, 1640 | 5.45 (s,1H), 6.40 (m,2H), 7.3 (d,2H), 7.6 (m,2 + 1H), 8.35 (s,1H) |
| (ah) | thiophen-2-yl (D,L), S | NH—⟨phenyl⟩—OH | 60 | 3320, 1660, 1570 | 5.4 (s,1H), 7.0 (m,2H), 7.4 (d,1H), 7.6 (m,1H), 8.25 (s,1H) |

TABLE II-continued

| | A | R | Yield % | IR-spectrum cm$^{-1}$ | NMR-spectrum Signals at ppm (DMSO + CD$_3$OD) |
|---|---|---|---|---|---|
| (aj) | HO—⟨⟩— | —NHCH$_2$—⟨⟩—OH | 62 | 3340, 1650, 1540 | 4.25 (broad, 2H), 5.15 (s,1H), 6.65 (m,4H), 7.15 (m,4H), 8.0 (s,1H) |
| (ak) | HO—⟨⟩— | —NHCH$_2$—⟨⟩—SO$_2$NH$_2$ | 48 | 3300, 1645, 1535 | 4.5 (broad, 2H), 6.80 (d,2H), 7.20 (d,2H), 7.50 (d,2H), 7.80 (d,2H), 8.05 (s,1H) |
| (al) | HO—⟨⟩— | —NH—⟨⟩—OH | 71.5 | 3320, 1650, 1545 | 5.15 (s,1H), 6.85 (d,2H), 7.5 (m,4H), 8.0 (d,2H), 8.30 (s,1H) |
| (am) | HO—⟨⟩— | —NH—⟨⟩—N(CH$_3$)$_2$ | 49 | 3350 (broad), 1645, 1540 | 3.0 (d,6H), 5.15 (s,1H), 6.80 (d,2H), 7.5 (m,4H), 7.7 (d,2H), 8.25 (s,1H) |
| (an) | HO—⟨⟩— | —NH—⟨⟩—NO$_2$ | 61 | 3300, 1640, 1545 | 3.05 (d,6H), 5.10 (s,1H), 6.75 (d,2H), 7.35 (d,2H), 7.6 (d,2H), 7.95 (d,2H), 8.40 (s,1H) |
| (ao) | HO—⟨⟩— | —NH—⟨⟩—COCH$_3$ | 57 | 3320, 1650 | 2.1 (s,3H), 5.15 (s,1H), 6.8 (d,2H), 7.40 (m,4H), 7.7 (d,2H), 8.25 (s,1H) |
| (ap) | HO—⟨⟩— | —NH—⟨⟩—NHCOCH$_3$ | 46 | 3350, 1640, 1610, 1540 | 2.05 (s,3H), 5.15 (s,1H), 6.75 (d,2H), 7.3 (d,2H), 7.4 (d,2H), 7.7 (d,2H), 8.3 (s,1H) |
| (aq) | HO—⟨⟩— | —NH—⟨⟩—NHCONH$_2$ | 64 | 3340, 1650, 1600, 1550 | 5.10 (s,1H), 6.70 (d,2H), 7.3 (d,2H), 7.35 (d,2H), 7.55 (d,2H), 8.2 (s,1H) |
| (ar) | HO—⟨⟩— | —NH—⟨⟩—SO$_2$NHC$_2$H$_5$ | 51 | 3330, 1645, 1545 | 1.25 (t,3H), 3.55 (m,2H), 5.15 (s,1H), 6.75 (d,2H), 7.25 (d,2H), 7.8 (q,4H), 8.35 (s,1H) |
| (as) | HO—⟨⟩— | —NH—⟨⟩—CONH$_2$ | 58 | 3350 (broad), 1650, 1600, 1550 | 5.15 (s,1H), 6.75 (d,2H), 7.35 (d,2H), 7.8 (dd), 8.40 (s,1H) |
| (at) | HO—⟨⟩— | —NH—⟨⟩—SO$_2$N(CH$_3$)$_2$ | 61 | 3320, 1650, 1530 | 2.45 (6H), 5.15 (s,1H), 6.75 (d,2H), 7.25 (d,2H), 7.75 (q,4H), 8.30 (s,1H) |
| (au) | HO—⟨⟩— | —NH—⟨⟩(CONH$_2$)(OH) | 37 | 3340, 1655, 1610, 1535 | 5.15 (s,1H), 6.85 (d,1H), 7.30 (d,2H), 7.55 (m,1H), 8.0 (d,1H), 8.1 (s,1H) |
| (av) | HO—⟨⟩— | —NH—⟨⟩(OH)(CONH$_2$) | 44 | 3360, 1655, 1605, 1535 | 5.10 (s,1H), 6.75 (d,2H), 7.25 (m,3H), 7.7 (m,2H), 8.35 (s,1H) |
| (aw) | HO—⟨⟩— | —NH—⟨⟩(OH)(SO$_2$NH$_2$) | 56.5 | 3320, 1650, 1540 | 5.15 (s,1H), 6.80 (d,2H), 7.30 (m,3H), 8.0 (m,2H), 8.35 (s,1H) |
| (ax) | HO—⟨⟩— | —NH—⟨⟩—SOCH$_3$ | 49.5 | 3330, 1660, 1530 | 2.7 (s,3H), 5.15 (s,1H), 6.75 (d,2H), 7.2–8.1 (m,6H) 8.35 (s,1H) |

TABLE II-continued

| A | R | Yield % | IR-spectrum cm⁻¹ | NMR-spectrum Signals at ppm (DMSO + CD₃OD) |
|---|---|---|---|---|
| (ay) 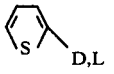 HO—⟨⟩— | NHCOCH₃ | 48 | 3330, 1655, 1580 | 2.3 (s,3H), 5.1 (s,1H), 6.8 (d,2H), 7.35 (d,2H), 8.25 (s,1H) |

(az)
D-α-(2-p-Aminosulfonylanilino-4-hydroxy-5-pyrimidinyl)-ureido-p-hydroxy-phenyl-acetic acid 1.405 gm (0.005 mol) of 5-amino-2-p-aminosulfonyl-anilino-4-hydroxy-pyrimidine were suspended in 50 ml of dry tetrahydrofuran and refluxed with 4 gm of trimethylsilyl diethylamine until the reaction mixture was completely dissolved (10–30 minutes). The solution was evaporated to dryness in vacuo, again taken up in 50 ml of tetrahydrofuran, and added dropwise to a solution of 530 mgm of phosgene in 35 ml of dry tetrahydrofuran while cooling with ice. After stirring for 10 minutes at room temperature, the reaction mixture was evaporated to dryness in vacuo. The residual solid product was admixed with 30 ml of methanol while cooling with ice, whereby a solution was obtained. After a short time pure 7-p-aminosulfonyl-anilino-2-hydroxy-oxazolo[5,4-d]pyrimidine precipitated, which was suction-filtered off and dried.

1.3 gm of the thus isolated intermediate product were added in portions, while cooling with ice, to a solution of 700 mgm (4.5 mmols) of p-hydroxyphenyl-glycine prepared with 4.5 ml of 1 N sodium hydroxide in 50 ml of 80% tetrahydrofuran. The pH-value was maintained at about 7.5. The further reaction was carried out analogous to Example 1(t).

Yield: 1.36 gm (76%).

IR-spectrum: 3300 (broad), 1640, 1530, 1155 cm⁻¹, NMR-spectrum (DMSO+CD₃OD) signals at ppm: 5.15 (s,1H), 6.77 (d,2H), 7.22 (d,2H), 7.80 (q,4H), 8.31 (s,1H).

The following compounds of the formula IV shown in the following table were prepared in analogous manner.

TABLE III

| | A | R | Yield % | IR-spectrum cm⁻¹ | NMR-spectrum Signals at ppm (DMSO + CD₃OD) |
|---|---|---|---|---|---|
| (ba) | 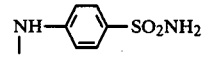 S, D,L | NH—⟨⟩—SO₂NH₂ | 81.5 | 3320, 1645, 1535 | 5.50 (s,1H), 7.05 (m,2H), 7.45 (m,1H), 7.8 (q,4H), 8.35 (s,1H) |
| (bb) | 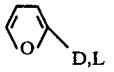 O, D,L | NH—⟨⟩—SO₂NH₂ | 68 | 3300, 1650, 1540 | 5.4 (s,1H), 6.45 (m,2H), 7.6 (s,1H), 7.8 (q,4H), 8.35 (s,1H) |
| (bc) | 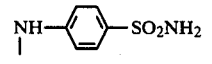 HO, HO—⟨⟩—D,L | NH—⟨⟩—SO₂NH₂ | 54 | 3320, 1655, 1545 | 5.15 (s,1H), 6.75 (m,2H), 7.3 (m,1H), 7.8 (q,4H), 8.35 (s,1H) |
| (bd) | 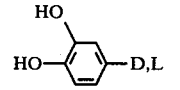 ⟨⟩— | NH—⟨⟩—SO₂NH₂ | 62 | 3340, 1660, 1545 | 2.50 (m,4H), 4.90 (1H), 5.30 (m,3H), 7.8 (q,4H), 8.35 (s,1H) |
| (be) | 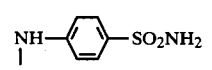 HO—⟨⟩— | NH—⟨⟩—SO₂NHCH₃ | 73 | 3330, 1655, 1550 | 2.45 (s,3H), 5.15 (s,1H), 6.80 (d,2H), 7.30 (d,2H), 7.75 (q,4H), 8.35 (s,1H) |
| (bf) |  S | NH—⟨⟩—SO₂NH₂ | 79 | 3300, 1660, 1555 | 2.45 (s,3H), 5.50 (s,1H), 7.05 (m,2H), 7.40 (m,1H), 7.80 (q,2H), 8.35 (s,1H) |
| (bg) | 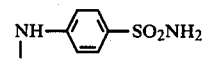 ⟨⟩— | NH—⟨⟩—SO₂NH₂ | 71 | 3300, 1650, 1550 | 5.15 (s,1H), 7.45 (m,5H), 7.80 q,4H), 8.35 (s,1H) |

Preparation of end products of the formula I

EXAMPLE 2

Sodium 7-{D-α-[(2-cyclopropyl-4-hydroxy-5-pyrimidinyl)-ureido]-p-hydroxy-phenylacetamido}-3-acetoxymethyl-ceph-3-em-4-carboxylate 1.72 gm (0.005 mol) of the ureidocarboxylic acid of Example 1a) together with 2.1 gm of 7-amino-3-acetoxymethyl-ceph-3-em-4-carboxylic acid benzhydryl ester (0.005 mol) were dissolved in methylene chloride. 1.15 gm (0.0055 mol) of dicyclohexylcarbodiimide were added while cooling with ice, and the solution was stirred for 5 hours at 5° C. After filtering off the urea, the filtrate was evaporated to dryness in vacuo. The obtained residue was purified by chromatography on a silicagel column (eluant:methylene chloride:methanol 12:1).

Yield of benzhydryl ester: 3.2 gm (82%).

The product thus obtained was suspended in a little methylene chloride and, while cooling with ice, was stirred for 30 minutes with 2 ml of anisol and 10 ml of trifluoroacetic acid. Subsequently, 50 ml of toluene were added twice, and the mixture was after each addition evaporated to dryness in vacuo. The product thus obtained was admixed with ether and isolated by suction filtration. By addition of the calculated amount of sodium ethyl hexanoate in methanol and of ether, the sodium salt was precipitated, suction-filtered and dried in vacuo.

Yield of sodium salt: 2.23 gm (91%).

IR-spectrum: 1760, 1660, 1615, 1550 cm$^{-1}$, NMR-spectrum (DMSO+CD$_3$OD) signals at ppm: 1.20 (m,4H), 1.95 (m,1H), 2.1 (s,3H), 3.45 (q,2H), 4.85 (q,2H), 4.90 (d,1H), 5.55 (s,1H), 5.60 (d,1H), 6.75 (d,2H), 7.3 (d,2H), 8.50 (s,1H).

EXAMPLE 3

Sodium 7-{D-α-[(2-cyclopropyl-4-hydroxy-5-pyrimidinyl)-ureido]-p-hydroxy-phenylacetamido}-3-[(1-methyl-tetrazol-5-yl)-thiomethyl]-ceph-3-em-4-carboxylate 3.44 gm (0.01 mol) of the ureidocarboxylic acid of Example 1a) were reacted analogous to Example 2 with 4.94 gm (0.01 mol) of 7-amino-3-[(1-methyl-tetrazol-5-yl)-thiomethyl]-ceph-3-em-4-carboxylic acid benzhydryl ester. After splitting off the protective group, 4.52 gm (65%) of the sodium salt were obtained.

IR spectrum: 1760, 1660, 1610, 1540 cm$^{-1}$, NMR-spectrum (DMSO+CD$_3$OD) signals at ppm: 1.25 (m,4H), 1.90 (m,1h), 3.50 (q,2H), 3.90 (s,3H), 4.30 (q,2H, partly covered by LM), 4.80 (d,1H) 5.50 (s,1H), 5.70 (d,1H), 6.75 (d,2H), 7.35 (d,2H), 8.45 (s,1H).

EXAMPLE 4

Sodium 7-{D-α-[(2-cyclopropyl-4-hydroxy-5-pyrimidinyl)-ureido]-p-hydroxy-phenylacetamido}-3-[(2-methyl-1,3,4-thiadiazol-5-yl)-thiomethyl]-ceph-3-em-4-carboxylate This compound was prepared analogous to Example 2, starting from 700 mgm (0.002 mol) of the ureidocarboxylic acid of Example 1a) and 1.02 gm (0.002 mol) of 7-amino-3-[(2-methyl-thiadiazol-5-yl)-thiomethyl]-ceph-3-em-4-carboxylic acid benzhydryl ester. After splitting off the protective group, 540 mgm (39%) of the sodium salt were obtained.

IR-spectrum: 1760, 1655, 1615, 1540 cm$^{-1}$, NMR-spectrum (DMSO+CD$_3$OD) signals at ppm: 1.0 (m,4H), 1.9 (m,1H), 2.7 (s,3H), 3.50 (q,2H), 4.45 (q,2H), 4.90 (d,1H), 5.50 (s,1H), 5.65 (d,1H), 6.75 (d,2H), 7.3 (d,2H), 8.45 (s,1H).

EXAMPLE 5

Sodium 7-{D,L-α-[(2-cyclopropyl-4-hydroxy-5-pyrimidinyl)-ureido]-2-thienylacetamido}-3-[(1-methyl-tetrazol-5-yl)-thiomethyl]-ceph-3-em-4-carboxylate This cephalosporin was prepared starting from 1.0 gm (0.0029 mol) of the ureidocarboxylic acid of Example 1b) and 1.5 gm (0.003 mol) of the benzhydryl ester used in Example 3, and carrying out the reaction analogous to Example 2. After splitting off the protective group, 930 mgm (48%) of the sodium salt were obtained.

IR-spectrum: 1760, 1660, 1610, 1540 cm$^{-1}$, NMR-spectrum (DMSO+CD$_3$OD) signals at ppm: 1.0 (m,4H), 1.9 (m,1H), 3.55 (q,2H), 3.90 (s,3H), 4.35 (q,2H), 4.90 (dd,1H), 5.5 (dd,1H), 5.75 (d,1H), 6.9 (m,2H), 7.35 (d,1H), 8.40 (s,1H).

EXAMPLE 6

Sodium 7-{D-α-[(2-p-aminosulfonylanilino-4-hydroxy-5-pyrimidinyl)-ureido]-p-hydroxy-phenylacetamido}-3-[(2-methyl-1,3,4-thiadiazol-5-yl)-thiomethyl]-ceph-3-em-4-carboxylate This cephalosporin was prepared from 950 mgm (0.2 mmol) of the ureidocarboxylic acid of Example 1 az) and 900 mgm of the diphenylmethyl ester of 7-amino-3-[(2-methyl-1,3,4-thiadiazol-5-yl)-thiomethyl]cephalosporanic acid according to the method of Example 2. The solvent was a mixture of methylene chloride and dimethylformamide (2:1). After splitting off the protective group, 821 mgm (54%) of the sodium salt were obtained.

IR-spectrum: 1760, 1660, 1600, 1150 cm$^{-1}$, NMR-spectrum (DMSO+CD$_3$OD) signals at ppm: 2.7 (s,3H), 3.50 (q,2H), 4.45 (q,2H), 4.90 (d,1H), 5.50 (s,1H), 5.65 (d,1H), 6.75 (d,2H), 7.35 (d,2H), 7.7 (d,2H), 8.0 (d,2H), 8.37 (s,1H).

EXAMPLE 7

Sodium 7{D-α-[4-hydroxy-2-isopropylamino-5-pyrimidinyl)-ureido]-p-hydroxy-phenylacetamido}-3-[(1-methyl-tetrazol-5-yl)-thiomethyl]-ceph-3-em-4-carboxylate This compound was prepared analogous to Example 2 from 3.55 gm (0.01 mol) of the ureidocarboxylic acid of Example 1e) and 4.94 gm (0.01 mol) of the cephalosporin derivative used in Example 3.

Yield after splitting off the protective group: 3.65 gm of the sodium salt (51%).

IR-spectrum: 1760, 1655, 1610, 1545 cm$^{-1}$, NMR-spectrum (DMSO+CD$_3$OD) signals at ppm: 1.15 (d,6H), 3.55 (q,2H), 3.90 (s,3H+m,1H), 4.30 (q,2H), 4.95 (d,1H), 5.4 (s,1H), 5.6 (d,1H), 6.8 (d,2H), 7.35 (d,2H), 8.05 (s,1H).

EXAMPLE 8

Sodium 7-{D-α-[(4-hydroxy-2-isopropylamino-5-pyrimidinyl)-ureido]-p-hydroxy-phenylaceamido}-3-[(2-methyl-1,3,4-thiadiazol-5-yl)-thiomethyl]-ceph-3-em-4-carboxylate This compound was prepared analogous to Example 2 from 500 mgm (0.0014 mol) of the ureidocarboxylic acid of Example 1e) and 720 mgm (0.0014 mol) of the cephalosporin used in Example 4.

Yield after splitting off the benzhydryl group: 460 mgm (45%) of the sodium salt.

IR-spectrum: 1760, 1660, 1610, 1550 cm$^{-1}$, NMR-spectrum (DMSO+CD$_3$OD) signals at ppm: 1.15 (d,6H), 2.75 (s,3H), 3.55 (q,2H), 3.95 (m,1H), 4.25 (q,2H, partly covered by LM), 5.0 (d,1H), 5.45 (s,1H), 5.65 (d,1H), 6.85 (d,2H) 7.35 (d,2H), 8.05 (s,1H).

EXAMPLE 9

Sodium 7-{D,L-α-[(4-hydroxy-2-propylamino-5-pyrimidinylureido]-2-furylacetamido}-3-[(1-methyl-tetrazol-5-yl)-thiomethyl]-ceph-3-em-4-carboxylate This compound was prepared analogous to Example 2 from 670 mgm of the ureidocarboxylic acid of Example 1f) (0.002 mol) and 1.0 gm (0.0021 mol) of the cephalosporin benzylhydryl ester used in Example 3.

After splitting off the benzylhydryl protective group, 680 mgm (50%) of the sodium salt were obtained.

IR-spectrum: 1760, 1655, 1615, 1545 cm$^{-1}$, NMR-spectrum (DMSO+CD$_3$OD) signals at ppm: 1.0 (t,3H), 1.6 (q,2H), 3.2 (t,2H), 3.55 (q,2H), 3.90 (s,3H), 4.35 (q,2H), 4.95 (dd,1H), 5.45 (dd,1H), 5.75 (d,1H), 6.4 (m,2H), 7.6 (s,1H), 8.05 (s,1H).

EXAMPLE 10

Sodium 7-{D-α-[(4-hydroxy-2-(2'-methylallylamino)-5-pyrimidinyl)-ureido]-p-hydroxy-phenylacetamido}-3-[(1-methyl-tetrazol-5-yl)-thiomethyl]-ceph-3-em-4-carboxylate This compound was prepared analogous to Example 2 370 from mgm (0.001 mol) of the ureidocarboxylic acid of Example 1l) and 500 mgm (0.001 mol) of the benzhydryl ester used in Example 3.

After splitting off the benzhydryl protective group, 385 mgm (53.5%) of the sodium salt were obtained.

IR-spectrum: 1760, 1655, 1615, 1540 cm$^{-1}$, NMR-spectrum (DMSO+CD$_3$OD) signals at ppm: 1.8 (s,3H), 3.4 (q,2H), 3.85 (broad s,2H), 4.35 (q,2H), 4.85 (m,2+1H), 5.40 (s,1H), 5.55 (d,1H), 6.7 (d,2H), 7.35 (d,2H), 8.0 (s,1H).

EXAMPLE 11

Sodium 7-{D,L-α-[(4-hydroxy-2-(4'-hydroxycyclohexylamino)-5-pyrimidinyl)-ureido]-2-thienylacetamido}-3-[(2-methylthiadiazol-5-yl)-thiomethyl]-ceph-3-em-4-carboxylate This compound was prepared analogous to Example 2 from 815 mgm (0.002 mol) of the ureidocarboxylic acid of Example 1v) and the benzhydryl ester of 7-amino-3-[(2-methyl-thiadiazol-5-yl)-thiomethyl]-ceph-3-em-4-carboxylic acid (0.002 mol).

After splitting off the protective group 640 mgm (42.5%) of the sodium salt were obtained.

IR-spectrum: 1760, 1660, 1615, 1540 cm$^{-1}$, NMR-spectrum (DMSO+CD$_3$OD) signals at ppm: 1.8 (m,8H), 2.7 (s, 3H), 3.45 (q, 2H), 3.5–4.1 (m,1+1H), 4.40 (q, 2H), 4.95 (dd, 1H), 5.45 (dd,1H), 5.70 (d, 1H), 6.9 (m,2H), 7.3 (d,1H), 8.05 (s,1H).

EXAMPLE 12

Sodium 7-{D,L-α-[(4-hydroxy-2-p-hydroxyanilino)-5-pyrimidinyl)-ureido]-2-thienylacetamido}-3-[1-methyl-tetrazol-5-yl)-thiomethyl]-ceph-3-em-4-carboxylate This compound was prepared analogous to Example 2 from 400 mgm (0.001 mol) of the ureidocarboxylic acid of Example 1 ah) and 500 mgm of the benzhydryl ester used in Example 3 (0.001 mol). After splitting off the protective group, 220 mgm of the sodium salt were obtained (29.5%).

IR-spectrum: 1760, 1655, 1615, 1540 cm$^{-1}$, NMR spectrum (DMSO+CD$_3$OD) signals at ppm: 3.45 (q, 2H), 3.90 (s, 3H), 4.30 (q, 2H, partly covered by LM), 4.95 (dd, 1H), 5.50 (dd, 1H), 5.65 (d, 1H), 7.0 (m, 2H), 7.5 (m, 5H), 8.25 (s,1H).

EXAMPLE 13

Sodium 7-{D-α-[(2-acetylamino-4-hydroxy-5-pyrimidinyl)-ureido]-p-hydroxy-phenylacetamido}-3-[(2-methyl-thiadiazol-5-yl)-thiomethyl]-ceph-3-em-4-carboxylate This compound was synthesized analogous to Example 2, starting from 1.0 gm of the ureidocarboxylic acid of Example 1 (ay) (0.0028 mol) and 1.53 gm (0.003 mol) of 7-amino-3-[-(2-methyl-thiadiazol-5-yl)-thiomethyl]-ceph-3-em-4-carboxylic acid benzhydryl ester.

Yield of sodium salt: 750 mgm (36%),

IR-spectrum: 1760, 1660, 1610, 1545 cm$^{-1}$, NMR-spectrum (DMSO+CD$_3$OD) signals at ppm: 2.3 (s, 3H), 2.75 (s,3H), 3.45 (q, 2H), 4.45 (q, 2H), 4.95 (d,1H), 5.40 (s, 1H), 5.60 (d, 2H), 6.85 (d,2H), 7.35 (d, 2H), 8.05 (s, 1H).

The following compounds were prepared in analogous manner:

Sodium 7-{D-α-[(2-p-chloroanilino-4-hydroxy-5-pyrimidinyl)-ureido]-p-hydroxy-phenylacetamido}-3-acetoxymethyl-ceph-3-em-4-carboxylate;

Sodium 7-{-D-α-[2-p-chloroanilino-4-hydroxy-5-pyrimidinyl)-ureido]-p-hydroxy-phenylacetamido}-3-[(2-methyl-thiadiazol-5-yl)-thiomethyl]-ceph-3-em-4-carboxylate;

Sodium 7-{D-α-[(2-cyclohexylamino-4-hydroxy-5-pyrimidinyl)-ureido]-p-hydroxy-phenylacetamido}-3-acetoxymethyl-ceph-3-em-4-carboxylate;

Sodium 7-{D-α-[(4-hydroxy-2-(4'-hydroxy-cyclohexylamino)-5-pyrimidinyl)-ureido]-p-hydroxy-phenylacetamido}-3-[(2-methyl-thiadiazol-5-yl)-thiomethyl]-ceph-3-em-4-carboxylate; and Sodium 7-{D-α-[(2-sec-butyl-amino-4-hydroxy-5-pyrimidinyl)-ureido]-p-hydroxy-phenylacetamido}-3-[(1,2,4-thiadiazol-5-yl)-thiomethyl]-ceph-3-em-4-carboxylate.

EXAMPLE 14

Sodium 7-{D-α-[(2-(3'-aminosulfonylpropylamino)-4-hydroxy-5-pyrimidinyl)-ureido]-p-hydroxy-phenylacetamido}-3-[(1-methyltetrazol-5-yl)-thiomethyl]-ceph-3-em-4-carboxylate This compound was synthesized analogous to Example 6, starting from 600 mgm (1.36 mmols) of the ureidocarboxylic acid of Example 1 ab) and 680 mgm of the cephalosporin of Example 3 (1.36 mmols).

After splitting off the protective group, 460 mgm of sodium salt were obtained (42%).

IR-spectrum: 1760, 1655, 1610, 1550 cm$^{-1}$, NMR-spectrum (DMSO+CD$_3$OD) signals at ppm: 2.0 (m, 2H), 2.75 (m, 2H), 3.35 (m, 2H), 3.5 (m, 2H), 3.95 (s, 3H), 4.35 (m, 2H), 4.90 (d, 1H), 5.4 (s, 1H), 5.6 (d, 2H), 6.75 (d, 2H), 7.3 (d, 2H), 8.10 (s, 1H).

EXAMPLE 15

Sodium 7-{D-α-[2-(3'-aminosulfonylpropylamino)-4-hydroxy-5-pyrimidinyl)-ureido]-p-hydroxy-phenylacetamido}-3-acetoxy-methyl-ceph-3-em-4-carboxylate This compound was synthesized analogous to Examples 6 or 14, but starting from the cephalosporin derivative of Example 2.

Yield: 47.5%.

IR-spectrum: 1760, 1650, 1615, 1550 cm$^{-1}$, NMR-spectrum (DMSO+CD$_3$OD) signals at ppm: 2.0 (m, 2H), 2.1 (s, 3H), 2.75 (m, 2H), 3.35 (m, 2H), 3.45 (m,2H), 4.80 (q, 2H+d, 1H), 5.45 (s, 1H), 5.60 (d,2H), 6.75 (d, 2H), 7.3 (d, 2H), 8.10 (s, 1H).

EXAMPLE 16

Sodium 7-{D-α-[(2-(3'-aminocarbonylpropylamino)-4-hydroxy-5-pyrimidinyl)-ureido]-p-hydroxy-phenylacetamido}-3-[(1-methyl-tetrazol-5-yl)-thiomethyl]-ceph-3-em-4-carboxylate This compound was synthesized analogous to Example 6, starting from 800 mgm (1.9 mmol) of the ureido carboxylic acid of Example 1 ac) and 950 mgm of the cephalosporin derivative of Example 3.

After splitting off the protective group, 602 mgm (40.5%) of the sodium salt were obtained.

IR-spectrum: 1760, 1655, 1610, 1555 cm$^{-1}$, NMR-spectrum (DMSO+CD$_3$OD) signals at ppm: 1.9 (t, 2H), 2.45 (m, 2H), 3.4–3.5 (m, 4H), 3.95 (s, 3H), 4.40 (m, 2H), 4.95 (d, 1H), 5.5 (s, 1H), 5.65 (d, 1H), 6.75 (d, 2H), 7.3 (d, 2H), 8.10 (s, 1H).

EXAMPLE 17

Sodium 7-{D-α-[(2-(2'-acetylaminoethylamino)-4-hydroxy-5-pyrimidinyl)-ureido]-p-hydroxy-phenylacetamido}-3-[(1-methyl-tetrazol-5-yl)-thiomethyl]-ceph-3-em-4-carboxylate This compound was synthesized analogous to Example 6, starting from 425 mgm of the ureidocarboxylic acid of Example 1 ae) (1.0 mmol) and 500 mgm of the cephalosporin derivative of Example 3.

Yield: 355 mgm of the sodium salt (46.5%), NMR-spectrum: (DMSO+CD$_3$OD) signals at ppm: 2.2 (d, 3H), 2.7 (m, 2H), 3.2–3.5 (m, 4H), 3.95 (s, 3H), 4.4 (q, 2H), 4.90 (d, 1H), 5.45 (s, 1H), 5.60 (d, 1H), 6.85 (d, 2H), 7.35 (d, 2H), 8.10 (s, 1H).

EXAMPLE 18

Sodium 7-{D-α-[(2-p-aminosulfonylbenzylamino-4-hydroxy-5-pyrimidinyl)-ureido]-p-hydroxy-phenylacetamido}-3-[(1-methyl-tetrazol-5-yl)-thiomethyl]-ceph-3-em-4-carboxylate This compound was synthesized analogous to Example 6, starting from 1.0 gm (2.05 mmols) of the ureido carboxylic acid of Example 1 ak) and 1.1 gm of the cephalosporin derivative of Example 3 (2.2 mmols).

Yield: 950 mgm (54.8%) of the sodium salt.

IR-spectrum: 1760, 1655, 1615, 1550 cm$^{-1}$, NMR-spectrum (DMSO+CD$_3$OD) signals at ppm: 3.5 (m, 2H), 3.95 (s, 3H), 4.3 (m, 2H), 4.55 (s, broad, 2H), 4.9 (d, 1H), 5.4 (s, 1H), 5.6 (d, 1H), 6.75 (d, 2H), 7.3 (d, 2H), 7.5 (d, 2H), 7.85 (d, 2H), 8.1 (s, 1H).

EXAMPLE 19

Sodium 7-{D-α-[2-p-aminosulfonylbenzylamino-4-hydroxy-5-pyrimidinyl)-ureido]-p-hydroxy-phenylacetamido}-3-acetoxymethyl-ceph-3-em-4-carboxylate This compound was synthesized analogous to Example 6, starting from 700 mgm (1.43 mmols) of the ureidocarboxylic acid of Example 1 ak) and 600 mgm of the cephalosporin derivative of Example 2.

Yield: 535 mgm (47%) of the sodium salt.

NMR-spectrum (DMSO+CD$_3$OD) signals at ppm: 2.05 (s, 3H), 3.45 (q, 2H), 4.55 (s, 2H), 4.9 (m, 2+1H), 5.5 (s, 1H), 5.6 (d, 1H), 6.75 (d, 2H), 7.3 (d, 2H), 8.1 (s, 1H).

EXAMPLE 20

Sodium 7-{D-α-[(2-p-aminosulfonylanilino-4-hydroxy-5-pyrimidinyl)-ureido]-p-hydroxy-phenylacetamido}-3-[(1-methyltetrazol-5-yl)-thiomethyl]-ceph-3-em-4-carboxylate 1.2 gm (2.53 mmols) of the ureidocarboxylic acid of Example 1 az) were dissolved in 30 ml of dry dimethylformamide, and the solution was admixed with a solution of 1.36 gm (2.75 mmols) of 7-amino-3-(1-methyl-tetrazol-5-yl) thiomethyl-cephalosporan-carboxylic acid diphenylmethyl ester in 50 ml of dry methylene chloride. After adding a solution of 0.57 gm of dicyclohexylcarbodiimide in 30 ml of dry methylene chloride while cooling with ice, the mixture was stirred for 8 hours at this temperature. The methylene chloride was then removed in a water aspirator vacuum, and the precipitated dicyclohexylurea was filtered off. The filtrate was evaporated to dryness in a high vacuum, and the residue was stirred twice with 40 ml each of methanol and once with methylene chloride. The residual solid product was suction-filtered off. According to thinlayer chromatographic analysis (eluant: methanol/methylene chloride 1:5), the product was uniform.

The splitting off of the diphenylmethyl ester group was carried out analogous to Example 2. The preparation of the sodium salt was carried out in dimethylformamide with sodium hexanoate.

Yield: 1.24 gm (61%) of the sodium salt (according to the NMR-spectrum, it contained about 1 mol of dimethylformamide).

NMR-spectrum: (DMSO+CD$_3$OD) signals at ppm: 3.45 (m, 2H), 3.92 (s, 3H), 4.35 (m, 2H, partly covered by LM), 4.88 (d, 1H), 5.45 (s, 1H), 5.55 (d, 1H), 6.72 (d, 2H), 7.30 (d, 2H), 7.7 (d, 2H), 8.0 (d, 2H), 8.38 (s, 1H), IR-spectrum 1760, 1660, 1605, 1150 cm$^{-1}$.

The following cephalosporins were synthesized in analogous manner, starting from 7-amino-3-(1-methyl-tetrazol-5-yl)-thiomethyl-cephalosporan-carboxylic acid diphenylmethyl ester or from 7-amino-3-acetoxymethyl-cephalosporan-carboxylic acid diphenyl methyl ester and the corresponding ureidocarboxylic acid:

TABLE IV

Structure:
A—CH(NH—CO—NH—[pyrimidine with OH, N, N, R])—CONH—[β-lactam]—CH₂—S—C(=C(COONa))—CH₂D

| Example No. | A | R | D | with the ureido carboxylic acid of Example | Yield % | IR-spectrum cm⁻¹ | NMR-spectrum (DMSO + CD₃OD) signals at ppm |
|---|---|---|---|---|---|---|---|
| 21 | HO—C₆H₄— | NH—C₆H₄—SO₂NH₂ | —OCOCH₃ | 1 (az) | 56 | 1760, 1660, 1600, 1150 | 2.05 (s,3H), 3.4 (q,2H), 5.0 (m,2 + 1H), 5.5 (s,1H), 5.65 (d,1H), 6.8 (d,2H), 7.35 (d,2H) 7.7 (d,2H), 8.0 (d,2H) 8.36 (s,1H) |
| 22 | thienyl D,L | NH—C₆H₄—SO₂NH₂ | —S—C(=N—N=N—NH) (tetrazole) | 1 (ba) | 64.5 | 1760, 1655, 1600, 1150 | 3.45 (m,2H), 3.95 (s,3H), 4.3 q,2H), 5.0 (dd,1H), 5.6 (dd,1H), 5.75 (d,1H), 6.8–7.2 (m,2H), 7.35 (m,1H), 7.7 (d,2H) 8.0 (d,2H), 8.35 (s,1H) |
| 23 | thienyl D,L | NH—C₆H₄—SO₂NH₂ | —OCOCH₃ | 1 (ba) | 59.5 | 1760, 1655, 1605, 1150 | 2.05 (s,3H), 3.45 (m,2H), 5.0 (m,2 + 1H), 5.45 (dd,1H), 5.75 (d,1H), 6.8–7.2 (m,2H), 7.30 (m,1H), 7.7 (d,2H), 8.0 (d,2H), 8.35 (s,1H) |
| 24 | C₆H₅— | NH—C₆H₄—SO₂NH₂ | —S—C(=N—N=N—N—CH₃) | 1 (bg) | 49 | 1760, 1650, 1600, 1150 | 3.4 (q,2H), 3.95 (s,3H), 4.35 (m,2H), 4.90 (d,1H), 5.50 (s,1H), 5.60 (d,1H), 7.2–7.7 (m,7H), 8.0 (d,2H), 8.35 (s,1H) |
| 25 | furyl D,L | NH—C₆H₄—SO₂NH₂ | —S—C(=N—N=N—N—CH₃) | 1 (bb) | 62 | 1760, 1605, 1150 | 3.45 (q,2H), 3.95 (s,3H), 4.35 (m,2H), 4.95 (dd,1H), 5.45 (dd,1H), 5.70 (d,1H), 6.4 (broad, 2H), 7.7 (m,3H), 8.0 (d,2H), 8.37 (s,1H) |

TABLE IV-continued

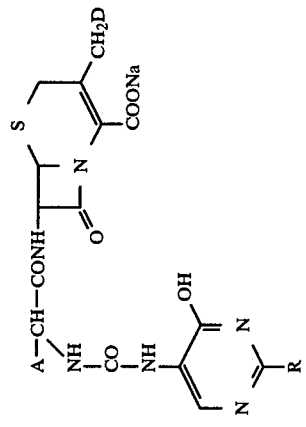

| Example No. | A | R | D | with the ureido carboxylic acid of Example | Yield % | IR-spectrum cm$^{-1}$ | NMR-spectrum (DMSO + CD$_3$OD) signals at ppm |
|---|---|---|---|---|---|---|---|
| 26 | furan-2-yl D,L | NH—⌬—SO$_2$NH$_2$ | —OCOCH$_3$ | 1 (bb) | 57 | 1760, 1655, 1600, 1150 | 2.05 (s,3H), 3.4 (m,2H), 4.9 (m,2 + 1H), 5.40 (dd,1H), 5.70 (d,1H), 6.45 (broad 2H), 7.6 (broad, 1H), 7.7 (d,2H), 8.0 (d,2H), 8.35 (s,1H) |
| 27 | 2,4-dihydroxyphenyl D,L | NH—⌬—SO$_2$NH$_2$ | N—N=N / CH$_3$ on S | 1 (bc) | 44 | 1760, 1660, 1600, 1150 | 3.40 (q,2H), 3.95 (s,3H), 4.4 (m,2H), 4.90 (d,1H), 5.50 (s,1H), 5.60 (d,1H), 6.75 (m,2H), 7.4 (m,1H), 7.7 (d,2H, 8.0 (d,2H), 8.35 (s,1H) |
| 28 | phenyl | NH—⌬—SO$_2$NH$_2$ | N—N=N / CH$_3$ on S | 1 (bd) | 46 | 1760, 1650, 1660, 1150 | 2.50 (m,4H), 3.45 (m,2H), 3.90 (s,3H), 4.4 (m,2H), 4.90 (d,1H), 5.2–5.6 (m,5H), 7.7 (d,2H), 8.0 (d,2H), 8.35 (s,1H) |
| 29 | 4-hydroxyphenyl | NH—⌬—SO$_2$NHCH$_3$ | OCOCH$_3$ | 1 (be) | 72 | 1760, 1660, 1605, 1150 | 2.05 (s,3H), 2.50 (s,3H), 3.45 (m,2H), 4.9 (m,2 + 1H), 5.45 (s,1H), 5.60 (d,1H), 6.75 (d,2H), 7.35 (d,2H), 7.85 (q,4H), 8.35 (s,1H) |
| 30 | 4-hydroxyphenyl | NH—⌬—SOCH$_3$ | N—N=N / CH$_3$ | 1 (ax) | 44 | 1760, 1655, 1600 | 2.7 (s,3H), 3.45 (q,2H), 3.95 (s,3H), 4.35 (q,2H), 4.05 (d,1H), 5.50 (s,1H), 5.60 (d,1H), 6.75 (d,2H), 7.2–7.95 (m,6H), 8.30 (s,1H) |

TABLE IV-continued $$\text{A—CH—CONH} \underset{\underset{\text{CO}}{|}}{\overset{\underset{|}{\text{NH}}}{|}} \text{—(β-lactam with } S, N, \text{CH}_2D, \text{COONa)}$$

$$R = \text{NH—} \underset{\text{N}}{\overset{\text{N}}{\diagdown}} \text{—R (pyridine with OH)}$$

| Example No. | A | R | D | with the ureido carboxylic acid of Example | Yield % | IR-spectrum cm$^{-1}$ | NMR-spectrum (DMSO + CD$_3$OD) signals at ppm |
|---|---|---|---|---|---|---|---|
| 31 | HO—⟨⟩— | NH—⟨⟩(OH)(SO$_2$NH$_2$) | N=N, N—CH$_3$ (triazole) | 1 (aw) | 40.5 | 1760, 1660, 1600, 1150 | 3.40 (q,2H), 3.95 (s,3H), 4.30 (q,2H), 4.90 (d,1H), 5.45 (s,1H), 5.55 (d,1H), 6.80 (d,2H), 7.30 (m,3H), 7.9 (m,2H), 8.35 (s,1H) |
| 32 | HO—⟨⟩— | NH—⟨⟩(OH)(CONH$_2$) | N=N, N—CH$_3$ (triazole) | 1 (av) | 46.5 | 1760, 1660, 1600 | 3.45 (q,2H), 3.95 (s,3H), 4.35 (q,2H), 4.95 (d,1H), 5.50 (s,1H), 5.60 (d,1H), 6.75 (d,2H), 7.25 (m,3H), 7.7 (m,2H), 8.30 (s,1H) |
| 33 | HO—⟨⟩— | NH—⟨⟩(CONH$_2$)(OH) | N=N, N—CH$_3$ (triazole) | 1 (au) | 51 | 1760, 1650, 1605 | 3.45 (q,2H), 3.95 (s,3H), 4.4 (m,2H), 4.90 (d,1H), 5.45 (s,1H), 5.55 (d,1H), 6.75 (d,2H), 6.85 (d,1H), 7.30 (d,2H), 7.55 (m,1H), 8.0 (d,1H), 8.15 (s,1H) |
| 34 | HO—⟨⟩— | NH—⟨⟩—SO$_2$N(CH$_3$)$_2$ | N=N, N—CH$_3$, S (thiadiazole) | 1 (at) | 68 | 1760, 1660, 1600, 1150 | 2.45 (d,6H), 3.45 (q,2H), 3.95 (s,3H), 4.35 (q,2H), 4.90 (d,1H), 5.45 (s,1H), 5.60 (d,1H), 6.75 (d,2H), 7.25 (d,2H), 7.75 (q,4H), 8.35 (s,1H) |
| 35 | HO—⟨⟩— | NH—⟨⟩—CONH$_2$ | OCOCH$_3$ | 1 (as) | 63 | 1760, 1640–60, 1600 | 2.05 (s,3H), 3.4 (m,2H), 4.90 (m,2 + 1H), 5.45 (s,1H), 5.60 (d,1H), 6.75 (d,2H), 7.35 (d,2H), 7.75 (dd,4H), 8.38 (s,1H) |

TABLE IV-continued

[Structure shown at top of table:]

A—CH—CONH—[β-lactam-cephem core]—CH₂D, COONa
     |
     NH
     |
     CO
     |
     NH—[pyrimidine with OH, N, R]

| Example No. | A | R | D | with the ureido carboxylic acid of Example | Yield % | IR-spectrum cm⁻¹ | NMR-spectrum (DMSO + CD₃OD) signals at ppm |
|---|---|---|---|---|---|---|---|
| 36 | HO–⟨phenyl⟩– | –NH–⟨phenyl⟩–CONH₂ | $\begin{array}{c}N=N\\ \|\quad \| \\ N\quad N-CH_3\\ \diagdown\diagup\\ S-\end{array}$ | 1 (as) | 69 | 1760, 1650, 1600 | 3.45 (q,2H), 3.95 (s,3H), 4.35 (m,2H), 4.95 (d,1H), 5.45 (s,1H), 5.55 (d,1H), 6.75 (d,2H), 7.35 (d,2H), 7.5–7.9 (m,4H), 8.37 (s,1H) |
| 37 | HO–⟨phenyl⟩– | –NH–⟨phenyl⟩–NHCONH₂ | same | 1 (aq) | 54.5 | 1760, 1660, 1605 | 3.40 (m,2H), 3.90 (s,3H), 4.40 (q,2H), 4.90 (d,1H), 5.50 (s,1H), 5.60 (d,1H), 6.75 (d,2H), 7.3 (d,2H), 7.40 (d,2H), 7.60 (d,2H), 8.2 (s,1H) |
| 38 | HO–⟨phenyl⟩– | –NH–⟨phenyl⟩–NO₂ | same | 1 (an) | 44 | 1760, 1655, 1600 | 3.45 (q,2H), 3.95 (s,3H), 4.40 (q,2H), 4.95 (d,1H), 5.45 (s,1H), 5.60 (d,1H), 6.75 (d,2H), 7.35 (d,2H), 7.6 (d,2H), 7.95 (d,2H), 8.40 (s,1H) |
| 39 | HO–⟨phenyl⟩– | –NH–⟨phenyl⟩–NHCOCH₃ | same | 1 (ap) | 50.5 | 1760, 1660, 1610–1600 | 2.1 (s,3H), 3.40 (q,2H), 3.95 (s,3H), 4.35 (q,2H), 4.95 (d,1H), 5.50 (s,1H), 5.60 (d,1H), 6.75 (d,2H), 7.3 (d,2H), 7.4 (d,2H), 7.7 (d,2H), 8.3 (s,1H) |
| 40 | HO–⟨phenyl⟩– | –NH–⟨phenyl⟩–COCH₃ | same | 1 (ao) | 53 | 1760, 1650–70, 1610 | 2.15 (s,3H), 3.45 (q,2H), 3.95 (s,3H), 4.4 (q,2H), 4.95 (d,1H), 5.50 (s,1H), 5.60 (d,1H), 6.75 (d,2H), 7.40 (m,4H), 7.7 (d,2H), 8.25 (s,1H) |

TABLE IV-continued $$\text{A—CH—CONH} \begin{array}{c} \text{NH} \\ | \\ \text{CO} \\ | \\ \text{NH} \end{array} \underset{\underset{N}{\parallel}}{\overset{OH}{\bigcirc}} R \quad / \!\!\!\!\!\! \begin{array}{c} S \\ \diagup \\ N \end{array} \!\!\!\! \begin{array}{c} CH_2D \\ \diagdown \\ COONa \end{array}$$

| Example No. | A | R | D | with the ureido carboxylic acid of Example | Yield % | IR-spectrum cm$^{-1}$ | NMR-spectrum (DMSO + CD$_3$OD) signals at ppm |
|---|---|---|---|---|---|---|---|
| 41 | HO—⌬— | —NHCH$_2$—⌬—OH | ⌬N—N⌬C(SCH$_3$)N—CH$_3$ | 1 (aj) | 69 | 1760, 1660, 1600 | 3.40 (q,2H), 3.95 (s,3H), 4.25 (broad signal, 2H), 4.40 (m,2H), 4.95 (d,1H), 5.50 (s,1H), 5.60 (d,1H), 6.65 (m,4H), 7.15 (m,4H), 8.05 (s,1H) |
| 42 | ⌬S (D,L) | —NH(CH$_2$)$_3$SO$_2$NH$_2$ | ⌬N—N⌬C(SCH$_3$)N—CH$_3$ | 1 (ad) | 61.5 | 1760, 1660, 1600, 1150 | 1.95 (m,2H), 2.8 (m,2H), 3.35 (m,4H), 3.95 (s,3H), 4.4 (m,2H), 4.95 (dd,1H), 5.45 (dd,1H), 5.7 (d,1H), 7.0 (m,2H), 7.4 (d,1H), 8.05 (s,1H) |
| 43 | HO—⌬— | —NH(CH$_2$)$_3$OH | ⌬N—N⌬C(SCH$_3$)N—CH$_3$ | 1 (z) | 59.5 | 1760, 1660, 1605 | 1.85 (m,2H), 3.3–3.5 (m,4H), 3.65 (m,2H), 3.95 (s,3H), 4.35 (q,2H), 4.95 (d,1H), 5.5 (s,1H), 5.6 (d,1H), 6.75 (d,2H), 7.35 (d,2H), 8.05 (s,1H) |

EXAMPLE 44

Sodium 7-{D-α-[(4-hydroxy-2-propylamino-5-pyrimidinyl)-ureido]-p-hydroxy-phenylacetamido}-3-acetoxymethyl-ceph-3-em-4-carboxylate 1.01 gm (0.01 mol) of N-methyl-morpholine were added to a solution of 3.35 gm (0.01 mol) of the ureidocarboxylic acid of Example 1 d) in 30 ml of anhydrous methylene chloride and 10 ml of dimethylformamide. After cooling this solution to $-15°$ C., a solution of 1.1 gm (0.01 mol) of ethyl chloroformate in 5 ml of methylene chloride was added dropwise at this temperature, and the resulting mixture was kept for 45 minutes at this temperature. 3 gm of N,O-bis-trimethylsilyl-acetamide were added to a suspension of 2.72 gm (0.01 mol) of 7-aminocephalosporanic acid in 80 ml of anhydrous acetonitrile. The resulting solution was cooled to $-20°$ C. and was added dropwise to the above prepared solution. After reacting this mixture at $-10°$ C. for 60 minutes and at 10° C. for 60 minutes, 5 ml of methanol were added, and the insoluble matter was filtered off. After removing the solvent from the filtrate in vacuo, the residue was taken up in 100 ml of water, and the solution was adjusted to pH 7.5. At this pH the solution was extracted twice with ethyl acetate, and the organic phase was discarded. After adjusting the aqueous phase to pH 2.9 with dilute hydrochloric acid while cooling with ice, the precipitated product was suction-filtered off, washed with a little water and dried in vacuo. The aqueous solution was extracted twice with ethyl acetate, the ethyl acetate phase was dried and the solvent was distilled off in vacuo. A second product batch was obtained, which, according to thin-layer chromatographic analysis, was identical with the previously precipitated product.

The two product batches were combined and dissolved in 80 ml of dried methanol with the calculated amount of sodium ethyl hexanoate. After filtering off some insoluble product, ether was added until complete precipitation was achieved. The precipitated product was suction-filtered off and dried.

Yield: 3.18 gm (53%) of the sodium salt,
IR-spectrum: 1760, 1655, 1615, 1545 cm$^{-1}$, NMR-spectrum (DMSO+CD$_3$OD) signals at ppm: 1.0 (t, 3H), 1.65 (q, 2H), 2.05 (s, 3H), 3.2 (q, 3H), 3.45 (q, 2H), 4.80 (q, 2H+d, 1H), 5.50 (s, 1H), 5.65 (d, 1H), 6.75 (d, 2H), 7.30 (d, 2H), 8.05 (s, 1H).

EXAMPLE 45

Sodium 7-{D-α-[(4-hydroxy-2-(4'-hydroxycyclohexylamino)-5-pyrimidinyl)-ureido]-p-hydroxy-phenylacetamido}-3-carbamoyloxymethyl-ceph-3-em-4-carboxylate This compound was prepared analogous to Example 44, starting from 1.32 gm (0.005 mol) of 7-amino-3-carbamoyloxymethyl-ceph-3-em-4-carboxylic acid and 2.02 (0.005 mol) of the ureidocarboxylic acid of Example 1 t).

Yield of the sodium salt: 1.47 gm (41%).
IR-spectrum: 1760, 1660, 1610, 1540 cm$^{-1}$, NMR-spectrum (DMSO+CD$_3$OD) signals at ppm: 1.8 (m, 8H), 3.55 (q, 2H), 3.6–4.1 (m, 1H+1H), 4.8 (broad, 2H+1H), 5.45 (s, 1H), 5.65 (d, 1H), 6.85 (d,2H), 7.35 (d, 2H), 8.0 (s, 1H).

EXAMPLE 46

Sodium 7-{D,L-α-[(2-cyclopropyl-4-hydroxy-5-pyrimidinyl)-ureido]-2-furylacetamido}-3-[(1-methyl-tetrazol-5-yl)-thiomethyl]-ceph-3-em-4-carboxylate This compound was prepared analogous to Example 44, starting from 310 mgm (0.001 mol) of the ureidocarboxylic acid of Example 1 (c) and 330 mgm (0.001 mol) of 7-amino-3-[(1-methyl-tetrazol-5-yl)-thiomethyl]-ceph-3-em-4-carboxylic acid.

Yield: 345 mgm (53.5%) of the sodium salt.
IR-spectrum: 1760, 1655, 1610, 1540 cm$^{-1}$, NMR-spectrum (DMSO+CD$_3$OD) signals at ppm: 1.0 (m, 4H), 1.95 (m, 1H), 3.50 (q, 2H), 3.95 (s, 3H), 4.35 (q, 2H), 4.95 (dd, 1H), 5.45 (dd, 1H), 5.70 (d, 1H), 6.4 (broad d, 2H), 7.6 (s, 1H), 8.45 (s, 1H).

EXAMPLE 47

Sodium 7-{D-α-[4-hydroxy-2-isopropylamino-5-pyrimidinyl)-ureido]-p-hydroxyphenylacetamido}-3-[(2-methylaminothiadiazol-5-yl)-thiomethyl]-ceph-3-em-4-carboxylate This compound was prepared analogous to Example 44, starting from 670 mgm (0.002 mol) of the ureidocarboxylic acid of Example 1 (e) and 720 mgm (0.002 mol) of 7-amino-3-[(2-methylamino-thiadiazol-5-yl)-thiomethyl]-ceph-3-em-4-carboxylic acid.

Yield of the sodium salt: 870 mgm (62%).
IR-spectrum: 1760, 1665, 1615, 1545 cm$^{-1}$, NMR-spectrum (DMSO+CD$_3$OD) signals at ppm: 1.15 (d, 6H), 3.0 (s, 3H), 3.65 (q, 2H), 3.95 (m, 1H), 4.16 (m, partly covered by LM=2H), 5.0 (d, 1H), 5.55 (s, 1H), 5.70 (d, 1H), 6.85 (d, 2H), 7.35 (d, 2H), 8.05 (s, 1H).

EXAMPLE 48

Sodium 7-{D-α-[(2-dimethylamino-4-hydroxy-5-pyrimidinyl)-ureido]-p-hydroxy-phenylacetamido}-3-[(1-methyl-tetrazol-5-yl)-thiomethyl]-ceph-3-em-4-carboxylate This compound was prepared analogous to Example 44, starting from 1.0 gm (0.0031 mol) of the ureidocarboxylic acid of Example 1 (i) and 1.0 gm (0.0031 mol) of the cephalosporin derivative used in Example 3.

Yield of the sodium salt: 1.08 gm (55%).
IR-spectrum: 1760, 1660, 1615, 1545 cm$^{-1}$, NMR-spectrum (DMSO+CD$_3$OD) signals at ppm: 3.0 (d, 6H), 3.5 (q, 2H), 3.95 (s, 3H), 4.35 (q, 2H), 4.85 (d, 1H), 5.45 (s, 1H), 5.65 (d, 1H), 6.70 (d, 2H), 7.3 (d, 2H), 8.05 (s, 1H).

Sodium 7-{D,L-α-[(2-diethylamino-4-hydroxy-5-pyrimidinyl)-ureido]-2-furylacetamido}-3-[(tetrazol-5-yl)-thiomethyl]-ceph-3-em-4-carboxylate was synthesized in analogous manner.

EXAMPLE 49

Sodium 7-{D-α-[(4-hydroxy-2-isobutylamino-5-pyrimidinyl)-ureido]-p-hydroxy-phenylacetamido}-3-[(2-acetylamino-thiadiazol-5-yl)-thiomethyl]-ceph-3-em-4-carboxylate This compound was prepared analogous to Example 44, starting from 370 mgm (0.0011 mol) of the ureidocarboxylic acid of Example 1 (j) and 390 mgm (0.001 mol) of 7-amino-3-[2-acetylamino-thiadiazol-5-yl)-thiomethyl]-ceph-3-em-4-carboxylic acid.

Yield of the sodium salt: 275 mgm (36%).

IR-spectrum: 1760, 1655, 1610, 1540 cm$^{-1}$, NMR-spectrum (DMSO+CD$_3$OD) signals at ppm: 0.9 (d, 6H), 1.8 (m, 1H), 2.3 (s, 3H), 3.1 (m, 2H), 3.70 (q, 2H), 4.25 (q, 2H), 5.0 (d, 1H), 5.5 (s, 1H), 5.65 (d, 1H), 6.85 (d, 2H), 7.4 (d, 2H), 8.0 (s, 1H).

EXAMPLE 50

Sodium 7-{D-α-[(4-hydroxy-2-isobutylamino-5-pyrimidinyl)-ureido]-p-hydroxy-phenylacetamido}-3-[1-methyl-tetrazol-5-yl)-thiomethyl]-ceph-3-em-4-carboxylate This compound was prepared analogous to Example 44, starting from 1.11 gm (0.003 mol) of the ureidocarboxylic acid of Example 1 (j) and 1 gm (0.003 mol) of the cephalosporin derivative used in Example 46.

Yield of the sodium salt: 1.02 gm (52%).

NMR-spectrum (DMSO+CD$_3$OD) signals at ppm: 0.9 (d, 6H), 1.85 (m, 1H), 3.1 (m, 2H), 3.5 (q, 2H), 3.90 (s, 3H), 4.35 (q, 2H), 4.90 (d, 1 H), 5.45 (s, 1H), 5.65 (d, 1H), 6.75 (d, 2H), 7.35 (d, 2H), 8.05 (s, 1H).

Sodium 7-{D-α-[(4-hydroxy-2-isobutylamino-5-pyrimidinyl)-ureido]-p-hydroxy-phenylacetamido}-3-[(tetrazol-5-yl)-thiomethyl]-ceph-3-em-4-carboxylate was synthesized in analogous manner.

EXAMPLE 51

Sodium 7-{D-α-[(2-(3'-methylallylamino)-4-hydroxy-5-pyrimidinyl)-ureido]-p-hydroxy-phenylacetamido}-3-[(1-methyltetrazol-5-yl)-thiomethyl]-ceph-3-em-4-carboxylate This compound was prepared analogous to Example 44, starting from 3.67 gm (0.01 mol) of the ureidocarboxylic acid of Example 1 (k) and 3.3 gm of the cephalosporin derivative used in Example 3.

Yield of the sodium salt: 3.4 g (49%).

IR-spectrum: 1760, 1670, 1610, 1550 cm$^{-1}$, NMR-spectrum (DMSO+CD$_3$OD) signals at ppm): 1.7 (d, 3H), 3.5 (q, 2H), 3.8 (broad signal, 2H), 3.90 (s, 3H), 4.35 (overlapped by LM), 4.85 (d, 1H), 5.4 (s, 2H), 5.55 (m, 2+1H), 6.7 (d, 2H), 7.25 (d, 2H), 8.0 (s, 1H).

The following compounds were synthesized in analogous manner:

Sodium 7-{D,L-α-[(2-(3'methylallylamino)-4-hydroxy-5-pyrimidinyl)-ureido]-2-furylacetamido}-3-[(1-methyltetrazol-5-yl)-thiomethyl]-ceph-3-em-4-carboxylate;

Sodium 7-{D-α-[(2-(3'-methylallylamino)-4-hydroxy-5-pyrimidinyl)-ureido]-p-hydroxy-phenylacetamido}-3-carbamoyloxymethyl-ceph-3-em-4-carboxylate; and Sodium 7-{D,L-α-[(4-hydroxy-2-(2'-methylallylamino)-5-pyrimidinyl)-ureido]-m,p-dihydroxy-phenylacetamido}-3-[(1-methyltetrazol-5-yl)-thiomethyl]-ceph-3-em-4-carboxylate.

EXAMPLE 52

Sodium 7-{D-α-[(2-cyclopentylamino-4-hydroxy-5-pyrimidinyl)-ureido]-p-hydroxy-phenylacetamido}-3-[1-methyl-tetrazol-5-yl)-thiomethyl]-ceph-3-em-4-carboxylate This compound was prepared analogous to Example 44, starting from 383 mgm (0.01 mol) of the ureidocarboxylic acid of Example 1 (n) and 328 mgm (0.001 mol) of the cephalosporin derivative used in Example 46.

Yield of the sodium salt: 425 mgm (59%).

IR-spectrum: 1760, 1655, 1610, 1540 cm$^{-1}$, NMR-spectrum (DMSO+CD$_3$OD) signals at ppm: 1.6 (m, 8H), b 3.5 (q, 2H) 3.95 (s, 3H), 4.1 (m, 1H covered by LM), 4.40 (q, 2H), 4.95 (d, 1H), 5.45 (s, 1H), 5.55 (d, 1H), 6.75 (d, 2H), 7.30 (d, 2H), 8.0 (s, 1H).

Sodium 7-{D-α-[(2-cyclopentylamino-4-hydroxy-5-pyrimidinyl)-ureido]-p-hydroxy-phenylacetamido}-3-[(2-methyl-thiadiazol-5-yl)-thiomethyl]-ceph-3-em-4-carboxylate was prepared in analogous manner.

EXAMPLE 53

Sodium 7-{D,L-α-[(2-cyclopentylamino-4-hydroxy-5-pyrimidinyl)-ureido]-2-thienyl-acetamido}-3-[(1-methyltetrazol-5-yl)-thiomethyl]-ceph-3-em-4-carboxylate This compound was prepared analogous to Example 44, starting from 760 mgm (0.002 mol) of the ureidocarboxylic acid of Example 1 n) and 655 mgm (0.002 mol) of the cephalosporin derivative used in Example 46.

Yield of the sodium salt: 650 mgm (46%).

IR-spectrum: 1760, 1665, 1620, 1550 cm$^{-1}$, NMR-spectrum (DMSO+CD$_3$OD) signals at ppm: 1.65 (m, 8H), 3.45 (q, 2H), 3.95 (s, 3H), 4.05 (m, 1H), 4.35 (q, 2H), 4.90 (dd, 1H), 5.50 (dd, 1H), 5.7 (d, 1H), 6.9 (broad, 2H), 7.30 (d, 1H) 8.05 (s, 1H).

The following compounds were prepared in analogous manner:

Sodium 7-{D,L-α-[(2-cyclopentylamino-4-hydroxy-5-pyrimidinyl)-ureido]-3-thienyl-acetamido}-3-[(1-methyltetrazol-5-yl)-thiomethyl]-ceph-3-em-4-carboxylate; and Sodium 7-{D,L-α-[(4-hydroxy-2-(4'-hydroxycyclohexylamino)-5-pyrimidinyl)-ureido]-2-furylacetamido}-3-[(1-methyl-tetrazol-5-yl)-thiomethyl]-ceph-3-em-4-carboxylate.

EXAMPLE 54

Sodium 7-{D-α-[(2-(2'-ethylmercaptoethylamino)-4-hydroxy-5-pyrimidinyl)-ureido]-p-hydroxy-phenylacetamido}-3-[(1-methyl-tetrazol-5-yl)-thiomethyl]-ceph-3-em-4-carboxylate This compound was prepared analogous to Example 44, starting from 400 mgm (0.001 mol) of the ureidocarboxylic acid of Example 1 (w) and 328 mgm (0.001 mol) of 7-amino-[(1-methyl-tetrazole-5-yl)-thiomethyl]-ceph-3-em-4-carboxylic acid.

Yield of the sodium salt: 260 mgm (35.5%).

IR-spectrum: 1760, 1655, 1610, 1550 cm$^{-1}$, NMR-spectrum (DMSO+CD$_3$OD) signals at ppm: 1.3 (d, 3H), 2.7 (m, 4H), 3.5 (q, 2H+m, 2H), 3.9 (s, 3H), 4.40 (q, 2H), 4.85 (d, 1H), 5.45 (s, 1H), 5.65 (d, 1H), 6.85 (d, 2H), 7.35 (d, 2H), 8.0 (s, 1H).

EXAMPLE 55

Sodium 7-{D,L-α-[(4-hydroxy-3-(3'-hydroxypropylamino)-5-pyrimidinyl)-ureido]-2-furyl-acetamido}-3-[(1-methyltetrazol-5-yl)-thiomethyl]-ceph-3-em-4-carboxylate This compound was prepared starting from 1.68 gm (0.005 mol) of the ureidocarboxylic acid of Example 1 (y) and 1.64 gm (0.005 mol) of the cephalosporin derivative used in Example 54.

Yield of the sodium salt: 1.49 gm (44%).
IR-spectrum: 1760, 1660, 1610, 1545 cm$^{-1}$, NMR-spectrum (DMSO+CD$_3$OD) signals at ppm: 1.85 (m, 2H), 3.3 (m, 2H), 3.45 (q, 2H), 3.6 (m, 2H), 3.95 (s, 3H), 4.35 (q, 2H), 4.95 (dd, 1H), 5.45 (dd, 1H), 5.70 (d, 1H), 6.4 (broad, 2H), 7.6 (s, 1H), 8.0 (s, 1H).

The following compounds were prepared in analogous manner:
Sodium 7-{D,L-α-[(4-hydroxy-2-(3'-hydroxy-propylamino)-5-pyrimidinyl)-ureido]-2-thienyl-acetamino}-3-[(1-methyl-tetrazol-5-yl)-thiomethyl]-ceph-3-em-4-carboxylate; and
Sodium 7-{D,L-α-[(4-hydroxy-2-(3'-hydroxy-propylamino)-5-pyrimidinyl)-ureido]-3-thienyl-acetamido}-3-[(1-methyl-tetrazol-5-yl)-thiomethyl]-ceph-3-em-4-carboxylate.

EXAMPLE 56
Sodium 7-{D-α-[(2-p-chloroanilino-4-hydroxy-5-pyrimidinyl)-ureido]-p-hydroxy-phenylacetamido}-3-[(1-methyl-tetrazol-5-yl))-thiomethyl]-ceph-3-em-4-carboxylate This compound was prepared analogous to Example 44, starting from 410 mgm (0.001 mol) of the ureido-carboxylic acid of Example 1 (af) and 328 mgm (0.001 mol) of the cephalosporin derivative used in Example 54.
Yield of the sodium salt: 360 mgm (48%).
IR-spectrum: 1760, 1655, 1620, 1550 cm$^{-1}$, NMR-spectrum (DMSO+CD$_3$OD) signals at ppm: 3.50 (q, 2H), 3.95 (s, 3H), 4.35 (q, 2H), 4.85 (d, 1H), 5.45 (s, 1H), 5.65 (d, 1H), 6.85 (d, 2H), 7.35 (d, 2H), 8.30 (s, 1H).

The following compounds were synthesized in analogous manner:
Sodium 7-{D,L-α-[(2-p-chloroanilino-4-hydroxy-5-pyrimidinyl)-ureido]-2-furylacetamido}-3-[(1-methyl-tetrazol-5-yl)-thiomethyl]-ceph-3-em-4-carboxylate;
Sodium 7-{D-α-[(4-hydroxy-2-p-hydroxyanilino-5-pyrimidinyl)-ureido]-p-hydroxy-phenylacetamido}-3-carbamoyloxymethyl-ceph-3-em-4-carboxylate; and
Sodium 7-{D-α-[(2-cyclopropyl-4-hydroxy-5-pyrimidinyl)-ureido]-p-hydroxy-phenylacetamido}-3-methyl-ceph-3-em-4-carboxylate.

EXAMPLE 57
Sodium 7-{D-α-[(2-p-aminosulfonylanilino-4-hydroxy-5-pyrimidinyl)-ureido]-p-hydroxy-phenylacetamido}-3-[(1-methyl-tetrazol-5-yl)-thiomethyl]-ceph-3-em-4-carboxylate This compound was synthesized analogous to Example 44, starting from 1.0 gm (2.05 mols) of the ureidocarboxylic acid of Example 1 (az) which was activated by means of ethyl chloroformate and triethylamine. The reaction mixture was subsequently reacted with an equimolar amount of silylated 7-amino-3-[(1-methyl-tetrazol-5-yl)-thiomethyl]-ceph-3-em-4-carboxylic acid.
The further processing was carried out analogous to Example 44.
According to thin-layer chromatographic analysis and its spectroscopic properties, the product obtained was identical to the product obtained in Example 20.
Yield: 57%.
The cephalosporins of the formula

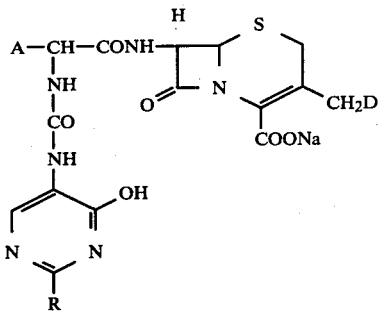

shown in the following table were synthesized in a manner analogous to Example 44:

TABLE V

| Example No. | A | R | D | with the ureido carboxylic acid of Example | Yield | IR-spectrum cm$^{-1}$ | NMR-spectrum (DMSO + CD$_3$OD) signals at ppm |
|---|---|---|---|---|---|---|---|
| 58 | HO—⌬— | NH(CH$_2$)$_3$SO$_2$NH$_2$ | N—N / S S CH$_3$ | (1 ab) | 47.5 | 1760, 1660, 1610, 1150 | 2.0 (m, 2H), 2.7 (m, 2H), 2.75 (s, 3H), 3.50 (m, 4H), 4.45 (q, 2H), 4.90 (d, 1H), 5.50 (s, 1H), 5.65 (d, 1H), 6.75 (d, 2H), 7.35 (d, 2H), 8.05 (s, 1H) |
| 59 | HO—⌬— | NH(OH$_2$)$_3$CONH$_2$ | OCOCH$_3$ | (1 ac) | 42 | 1760, 1655, 1600 | 1.9 (t, 2H), 2.05 (s, 3H), 2.5 (m, 2H), 3.45 (m, 4H), 4.9 (m, 2 + 1H), 5.5 (s, 1H), 5.6 (d, 1H), 6.8 (d, 2H), 7.3 (d, 2H), 8.05 (s, 1H) |
| 60 | HO—⌬— | NH—⌬—OH | N—N / S S CH$_3$ | (1 al) | 51 | 1760, 1660, 1605 | 2.75 (s, 3H), 3.50 (q, 2H), 4.45 (q, 2H), 4.90 (d, 1H), 5.55 (s, 2H), 5.65 (d, 1H), 6.75 (d, 2H), 7.35 (d, 2H), 7.45 (d, 2H), 7.85 (d, 2H), 8.30 (s, 1H) |

TABLE V-continued
| | | | | | | | |
|---|---|---|---|---|---|---|---|
| 61 |  | 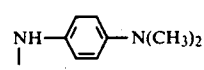 | 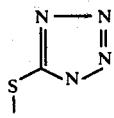 | (1 am) | 34.5 | 1760, 1655, 1595 | 2.95 (d, 6H), 3.45 (q, 2H), 4.35 (q, 2H), 4.95 (d, 1H), 5.5 (s, 1H), 5.6 (d, 1H), 6.80 (d, 2H), 7.3 (d, 2H), 7.4 (d, 2H), 7.7 (d, 2H) 8.25 (a, 1H) |
| 62 |  | 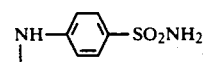 | 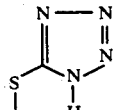 | (1 az) | 68 | 1760, 1660, 1600, 1150 | 3.40 (m, 2H), 4.4 (q, 2H), 4.95 (d, 1H), 5.45 (s, 1H), 5.55 (d, 1H), 6.80 (d, 2H), 7.35 (d, 2H), 7.7 (d, 2H), 8.0 (d, 2H) 8.35 (s, 1H) |
| 63 |  | 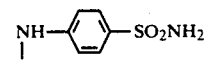 | 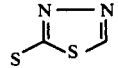 | (1 az) | 60.5 | 1760, 1660, 1605, 1150 | 3.50 (q, 2H), 4.45 (q, 2H), 4.90 (d, 1H), 5.50 (s, 1H), 5.65 (d, 1H), 6.75 (d, 2H), 7.35 (d, 2H), 7.7 (d, 2H), 8.0 (d, 2H), 8.37 (s, 1H), 9.25 (s, 1H) |
| 64 |  | 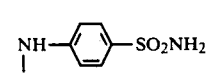 | —OCONH$_2$ | (1 az) | 54 | 1760, 1660, 1610, 1145 | 3.45 (q, 2H), 4.8 (m, 2 + 1H), 5.50 (s, 1H), 5.60 (d, 1H), 6.75 (d, 2H), 7.30 (d, 2H), 7.7 (d, 2H), 8.0 (d, 2H), 8.35 (s, 1H) |
| 65 | 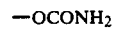 |  | 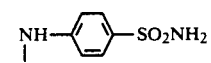 | (1 az) | 69 | 1760, 1650, 1600, 1150 | 2.85 (s, 3H), 3.4 (m, 2H), 4.35 (q, 2H), 4.95 (d, 1H), 5.5 (s, 1H) 5.6 (d, 1H), 6.75 (d, 2H), 7.3 (d, 2H), 7.65 (d, 2H), 7.95 (d, 2H), 8.35 (s, 1H), 8.38 (s, 1H) |
| 66 | 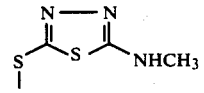 |  | 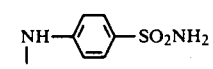 | (1 az) | 46.5 | 1760, 1660, 1600, 1150 | 2.45 (s, 3H), 3.6 (q, 2H), 4.2 (q, 2H, partly covered by LM), 4.90 (d, 1H), 5.45 (s, 1H), 5.55 (d, 1H), 6.75 (d, 2H), 7.35 (d, 2H), 7.65 (d, 2H), 8.0 (d, 2H), 8.35 (s, 1H) |
| 67 | 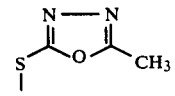 |  | 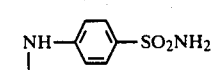 | (1 az) | 53.5 | 1760, 1655, 1600, 1150 | 3.4 (q, 2H), 4.4 (q, 2H), 4. (d, 1H), 5.5 (s, 1H), 5.6 (d, 1H), 6.75 (d, 2H), 7.35 (d, 2H), 7.65 (d, 2H), 8.0 (d, 2H), 8.35 (s, 1H), 8.36 (s, 1H) |
| 68 | 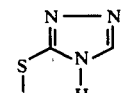 |  | OCONH$_2$ | (1 ba) | 51.5 | 1760, 1660, 1605, 1150 | 3.45 (q, 2H), 4.8 (m, 2 + 1H), 5.55 (dd, 1H), 5.7 (d, 1H), 6.8–7.2 (m, 2H), 7.35 (m, 1H), 7.7 (d, 2H), 8.0 (d, 2H) 8.38 (s, 1H) |
| 69 | 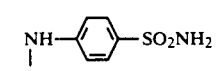 |  |  | (1 ba) | 54 | 1760, 1655, 1610, 1150 | 2.7 (s, 1H), 3.50 (q, 2H), 4.45 (q, 2H), 4.9 (dd, 1H), 5.55 (dd, 1H), 5.7 (d, 1H), 6.8–7 (m, 2H), 7.35 (m, 1H), 7.7 (d, 2H), 8.0 (d, 2H), 8.37 (s, 1H) |
| 70 | 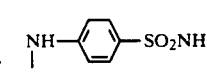 | 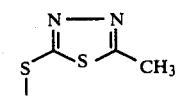 |  | (1 be) | 71 | 1760, 1660, 1600, 1150 | 2.40 (s, 3H), 3.40 (m, 2H), 3.95 (s, 3H), 4.35 (q, 2H), 4.95 (d, 1H), 5.55 (s, 1H), 5.60 (d, 1H), 6.75 (d, 2H), 7.3 (d, 2H), 7.80 (q, 4H), 8.35 (s, 1H) |
with the ureido car- TABLE V-continued

| Example No. | A | R | R | boxylic acid of example | Yield | IR-spectrum cm$^{-1}$ | NMR-spectrum (DMSO + CD$_3$OD) signals at ppm |
|---|---|---|---|---|---|---|---|
| 71 | thiophene-D,L | NH—⟨⟩—SO$_2$NHCH$_3$ | tetrazole-S-CH$_3$ | (1 be) | 66 | 1760, 1660, 1600, 1145 | 2.42 (s, 3H), 3.40 (m, 2H), 3.95 (s, 3H), 4.4 (q, 2H), 4.9 (dd, 1H), 5.55 (dd, 1H), 5.75 (d, 1H), 7.05 (m, 2H), 7.45 (m, 1H), 7.80 (q, 2H), 8.35 (s, 1H) |
| 72 | HO—⟨⟩— | NH—⟨⟩—SO$_2$NHC$_2$H$_5$ | tetrazole-S-CH$_3$ | (1 ar) | 73.5 | 1760, 1665, 1600, 1155 | 1.25 (t, 3H), 3.3 (m, 4H), 3.95 (s, 3H), 4.4 (q, 2H), 4.95 (d, 1H), 5.50 (s, 1H), 5.60 (d, 1H), 6.75 (d, 2H), 7.35 (d, 2H), 7.8 (q, 4H), 8.35 (s, 1H) |
| 73 | thiophene-D,L | NH—⟨⟩—OH | tetrazole-S-CH$_3$ | (1 v) | 66 | 1760, 1660, 1605, | 1.80 (m, 8H), 3.35 (m, 2H), 3.5–4.0 (m, 1 + 1H, s, 3H), 4.35 (q, 2H), 4.9 (dd, 1H), 5.50 (dd, 1H), 5.75 (d, 1H), 7.0 (m, 2H), 7.4 (m, 1H), 8.05 (s, 1H) |

EXAMPLE 74

Sodium 7-β-{D-α-[(2-cyclopropyl-4-hydroxy-5-pyrimidinyl)-ureido]-p-hydroxy-phenylacetamido}-7-α-methoxy-3-[(1-methyltetrazol-5-yl)-thiomethyl]-ceph-3-em-4-carboxylate 220 mgm of dicyclohexyl-carbodiimide were added to a solution of 340 mgm (0.001 mol) of the ureidocarboxylic acid of Example 1 (a) and 525 mgm (0.001 mol) of 7-β-amino-7-α-methoxy-3-[(1-methyl-tetrazol-5-yl)-thiomethyl]-ceph-3-em-4-carboxylic acid diphenylmethyl ester in 20 ml of anhydrous methylene chloride and 10 ml of dimethylformamide. After stirring for 2 hours while cooling with ice and for 4 hours at room temperature, almost no starting material could be detected by thin-layer chromatogram. The precipitated dicyclohexyl-urea was filtered off, and the filtrate was evaporated to dryness. The residue was purified by chromatography on a silicagel column (eluant: methylene chloride/methanol 12:1). The benzhydryl ester thus obtained was split with trifluoroacetic acid anisole analogous to Example 2, and subsequently the sodium salt was prepared.

Yield of the sodium salt: 295 mgm (42.5%).

IR spectrum: 1760, 1650, 1610, 1540 cm$^{-1}$, NMR spectrum (DMSO+CD$_3$OD) signals at ppm: 0.9 (m, 4H), 1.9 (m, 1H), 3.45 (m, 2H), 3.46 (s, 3H), 3.9 (s, 3H), 4.95 (s, 1H), 5.45 (s, 1H), 6.85 (d, 2H), 7.35 (d, 2H), 8.40 (s, 1H).

EXAMPLE 75

Sodium 7-β-{D-α-[(2-p-aminosulfonylanilino-4-hydroxy-5-pyrimidinyl)-ureido]-p-hydroxy-phenylacetamido}-7-α-methoxy-3-[(1-methyl-tetrazol-5-yl)-thiomethyl]-ceph-3-em-4-carboxylate 2.37 gm (0.005 mol) of the ureidocarboxylic acid of Example 1 (az) were dissolved in a mixture of 40 ml of anhydrous methylene chloride and 30 ml of anhydrous dimethylformamide. After adding 525 mgm of N-methyl morpholine, the reaction mixture was cooled to −20° C. At this temperature a solution of 575 mgm of ethyl chloroformate in 5 ml of anhydrous methylene chloride was added dropwise over a period of 5 minutes, and the mixture was stirred for 60 minutes at −15° C. After adding a solution of 2.62 gm of 7-β-amino-7-α-methoxy-3-[(1-methyl-tetrazol-5-yl)-thiomethyl]-ceph-3-em-4-carboxylic acid diphenylmethyl ester (0.005 mol) in methylene chloride, the reaction mixture was reacted for 60 minutes at −10° C. and for 120 minutes at +10° C. The reaction mixture was evaporated to dryness in vacuo and admixed with 30 ml of water. The remaining solid product was washed, while stirring, first with 100 ml of methylene chloride, then with 50 ml of methanol and subsequently with ether. A pale yellow powder was obtained, which was purified by chromatography on a silicagel column (eluant: methylene chloride/methanol 6:1). The principal ester component was split with trifluoroacetic acid/anisole and converted into the sodium salt.

IR spectrum: 1765, 1660, 1600, 1150 cm$^{-1}$, NMR spectrum (DSMO+CD$_3$OD) signals at ppm: 3.40 (m, 2H), 3.47 (s, 3H), 3.9 (s, 3H), 4.95 (s, 1H), 5.50 (s, 1H), 6.85 (d, 2H), 7.35 (d, 2H), 7.65 (d, 2H), 8.0 (d, 2H), 8.40 (s, 1H).

Using a procedure analogous to that described in Example 75 and starting from 7-β-amino-7-α-methoxy-3-[(1-methyl-tetrazol-5-yl)-thiomethyl]-ceph-3-em-4-carboxylic acid diphenylmethyl ester, the cephalosporins named in the following examples were prepared by reaction with the indicated ureidocarboxylic acid.

EXAMPLE 76

Sodium 7-β-{D-α-[(4-hydroxy-2-propylamino-5-pyrimidinyl)-ureido]-p-hydroxy-phenylacetamido}-7-α-methoxy-3-[(1-methyltetrazol-5-yl)-thiomethyl]-ceph-3-em-4-carboxylate With the ureidocarboxylic acid of Example 1 (d). Yield: 38.5%.

IR spectrum: 1770, 1670, 1620, 1540 cm$^{-1}$, NMR spectrum (DMSO+CD$_3$OD) signals at ppm. 1.0 (t, 3H), 1.6 (q, 2H), 3.2 (t, 2H), 3.50 (q, 2H), 3.50 (s, 3H), 3.95 (s, 3H), 4.35 (q, 2H), 4.95 (s, 1H), 5.50 (s, 1H), 6.85 (d, 2H), 7.3 (d, 2H), 8.0 (s, 1H).

EXAMPLE 77

Sodium 7-β-{D-α-[(4-hydroxy-2-isopropylamino-5-pyrimidinyl)-ureido]-p-hydroxy-phenylacetamido}-7-α-methoxy-3-[(1-methyltetrazol-5-yl)-thiomethyl]-ceph-3-em-4-carboxylate With the ureidocarboxylic acid of Example 1 (e). Yield: 46%.

IR spectrum: 1765, 1660, 1610, 1550 cm$^{-1}$, NMR spectrum (DMSO+CD$_3$OD) signals at ppm: 1.15 (d, 6H), 3.50 (q, 2H), 3.45 (s, 3H), 3.9 (m, 1H+s, 3H) 4.35 (q, 2H), 4.90 (s, 1H), 5.50 (s, 1H), 6.85 (d, 2H), 7.35 (d, 2H), 8.0 (s, 1H).

EXAMPLE 78

Sodium 7-β-{D,L-α-[(4-hydroxy-2-propylamino-5-pyrimidinyl)-ureido]-2-thienyl-acetamido}-7-α-methoxy-3-[(1-methyl-tetrazol-5-yl)-thiomethyl]-ceph-3-em-4-carboxylate With the ureidocarboxylic acid of Example 1 (h). Yield: 47%.

IR spectrum: 1765, 1655, 1610, 1545 cm$^{-1}$, NMR spectrum (DMSO+CD$_3$OD) signals at ppm: 1.0 (t, 3H), 1.65 (q, 2H), 3.2 (m, 2H), 3.50 (q, 2H), 3.50 (s, 3H), 3.90 (s, 3H), 4.30 (q, 2H), 4.90 (s, 1H), 5.75 (s, 1H), 6.9 (broad, 2H), 7.30 (d, 1H), 8.0 (s, 1H).

EXAMPLE 79

Sodium 7-β-{D-α-[(2-cyclopentylamino-4-hydroxy-5-pyrimidinyl)-ureido]-p-hydroxy-phenylacetamido}-7-α-methoxy-3-[(1-methyl-tetrazol-5-yl)-thiomethyl]-ceph-3-em-4-carboxylate With the ureidocarboxylic acid of Example 1 (n). Yield: 52%.

IR-spectrum: 1765, 1665, 1620, 1550 cm$^{-1}$, NMR-spectrum (DMSO+CD$_3$OD) signals at ppm: 1.65 (m, 8H), 3.5 (q, 2H), 3.45 (s, 3H), 3.9 (s, 3H), 4.05 (m, covered by LM), 4.4 (q, 2H), 4.85 (s, 1H), 5.45 (s, 1H), 6.85 (d, 2H), 7.35 (d, 2H), 8.0 (s, 1H).

EXAMPLE 80

Sodium 7-β-{D-α-[(4-hydroxy-2-(4'-hydroxy-cyclohexylamino)-5-pyrimidinyl)-ureido]-p-hydroxy-phenylacetamido}-7-α-methoxy-3-[(1-methyl-tetrazol-5-yl)-thiomethyl]-ceph-3-em-4-carboxylate With the ureidocarboxylic acid of Example 1 (t). Yield: 47%.

IR-spectrum: 1765, 1660, 1615, 1540 cm$^{-1}$, NMR-spectrum (DMSO+CD$_3$OD) signals at ppm: 1.75 (m, 8H), 3.45 (q, 2H), 3.6–4.0 (broad, m, 1H+1H), 3.50 (s, 3H), 3.95 (s, 3H), 4.35 (q, 2H), 4.85 (s, 1H), 5.45 (s, 1H), 6.85 (d, 2H), 7.35 (d, 2H), 8.05 (s, 1H).

Starting from the corresponding cephalosporin derivative, the 7-α-methoxy cephalosporins of the formula

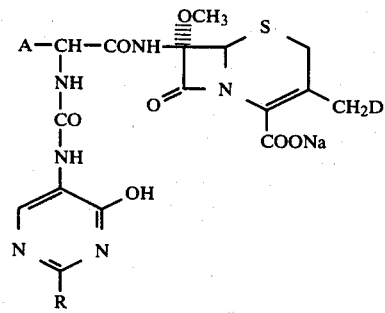

shown in the following table were synthesized analogous to Example 75:

TABLE VI

| Example No. | A | R | D | with the ureido carboxylic acid of Example | Yield | IR-spectrum cm$^{-1}$ | NMR-spectrum (DMSO + CD$_3$OD) signals at ppm |
|---|---|---|---|---|---|---|---|
| 81 | HO—⟨phenyl⟩— | NH(CH$_2$)$_3$OH | N—N, ║N, S—⟨⟩—N—CH$_3$ | 1 (z) | 44.5 | 1765, 1660, 1600 | 1.85 (m, 2H), 3.2–3.6 (m, 3H), 3.45 (s, 3H), 3.95 (s, 3H), 4.4 (q, 2H), 4.95 (s, 1H), 5.5 (s, 1H), 6.75 (d, 2H), 7.35 (d, 2H), 8.05 (s, 1H) |
| 82 | HO—⟨phenyl⟩— | NH(CH$_2$)$_3$SO$_2$NH$_2$ | N—N, ║N, S—⟨⟩—N—CH$_3$ | 1 (ab) | 57 | 1765, 1660, 1600, 1150 | 1.95 (m, 2H), 2.75 (m, 2H), 3.35 (m, 4H), 3.50 (s, 3H), 3.95 (s, 3H), 4.40 (q, 2H), 4.95 (s, 1H), 5.55 (s, 1H), 6.85 (d, 2H), 7.35 (d, 2H), 8.05 (s, 1H) |
| 83 | ⟨thienyl⟩—D,L | NH(CH$_2$)$_3$SO$_2$NH$_2$ | N—N, ║N, S—⟨⟩—N—CH$_3$ | 1 (ad) | 38 | 1765, 1655, 1605, 1145 | 1.9 (m, 2H), 2.8 (m, 2H), 3.4 (m, 4H), 3.45 (s, 3H), 3.93 (s, 3H), 4.35 (q, 2H), 5.00 (d, 1H), 5.75 (d, 1H), 7.0 (m, 2H), 7.4 (d, 1H), 8.05 (s, 1H) |
| 84 | HO—⟨phenyl⟩— | NH(CH$_2$)$_3$CONH$_2$ | N—N, ║N, S—⟨⟩—N—CH$_3$ | 1 (ac) | 46.5 | 1765, 1650, 1600 | 1.9 (t, 2H), 2.5 (m, 2H), 3.45 (m, 4H + s, 3H), 3.90 (s, 3H), 4.3 (m, 2H), 4.95 (s, 1H), 5.55 (d, 1H), 6.80 (d, 2H), 7.35 (d, 2H), 8.05 (s, 1H) |

TABLE VI-continued

| Example No. | A | R | D | with the ureido carboxylic acid of Example | Yield | IR-spectrum cm$^{-1}$ | NMR-spectrum (DMSO + CD$_3$OD) signals at ppm |
|---|---|---|---|---|---|---|---|
| 85 | thiophene-2-yl (D,L) | NH—C$_6$H$_4$—SO$_2$NHCH$_3$ | N—N=N—N(CH$_3$)—C(=S)— (1-methyl-tetrazol-5-yl-thio) | 1 (be) | 51.5 | 1765, 1660, 1600, 1150 | 2.4 (s, 3H), 3.45 (m, 2H + s, 3H), 3.95 (s, 3H), 4.35 (q, 2H), 4.95 (d, 1H), 5.7 (d, 1H), 6.85 (d, 2H), 7.35 (d, 2H), 7.85 (q, 4H), 8.37 (s, 1H) |
| 86 | HO—C$_6$H$_4$— | NH—C$_6$H$_4$—OH | N—N=N—N(CH$_3$)—C(=S)— | 1 (al) | 41 | 1765, 1660, 1610 | 3.35 (m, 2H), 3.50 (s, 3H), 3.95 (s, 3H), 4.35 (q, 2H), 4.95 (s, 1H), 5.50 (s, 1H), 6.75 (d, 2H), 7.35 (d, 2H), 7.45 (d, 2H), 7.8 (d, 2H), 8.30 (s, 1H) |
| 87 | thiophene-2-yl (D,L) | NH—C$_6$H$_4$—SO$_2$NH$_2$ | N—N=N—N(CH$_3$)—C(=S)— | 1 (ba) | 49.5 | 1765, 1655, 1605, 1155 | 3.45 (q, 2H), 3.50 (s, 3H), 3.95 (s, 3H), 4.4 (q, 2H), 5.0 (d, 1H), 5.75 (d, 1H), 7.0 (m, 2H), 7.4 (d, 1H), 7.7 (d, 2H), 8.0 (d, 2H), 8.38 (s, 1H) |
| 88 | thiophene-2-yl (D,L) | NH—C$_6$H$_4$—SO$_2$NH$_2$ | OCONH$_2$ | 1 (ba) | 50 | 1765, 1660, 1610 | 3.45 (s, 3H), 3.50 (q, 2H), 4.8 (m, 2 + 1H), 5.70 (d, 1H), 7.0 (m, 2H), 7.4 (d, 1H), 7.7 (d, 2H), 8.0 (d, 2H), 8.36 (s, 1H) |
| 89 | HO—C$_6$H$_4$— | NH—C$_6$H$_4$—SO$_2$NH$_2$ | OCOCH$_3$ | 1 (az) | 61.5 | 1765, 1655, 1600 | 2.05 (s, 3H), 3.35 (q, 2H), 3.45 (s, 3H), 4.85 (q, 1H + s, 1H), 5.50 (1, 1H), 6.85 (d, 2H), 7.35 (d, 2H), 7.7 (d, 2H), 8.0 (d, 2H), 8.36 (s, 1H) |
| 90 | HO—C$_6$H$_4$— | NH—C$_6$H$_4$—SO$_2$NH$_2$ | OCONH$_2$ | 1 (az) | 44 | 1765, 1660, 1610 | 3.45 (s, 3H), 3.50 (q, 2H), 4.8 (m, 2 + 1H), 5.50 (s, 1H), 6.85 (d, 2H), 7.35 (d, 2H), 7.7 (d, 2H), 7.95 (d, 2H), 8.37 (s, 1H) |
| 91 | HO—C$_6$H$_4$— | NH—C$_6$H$_4$—CONH$_2$ | N—N=N—N(CH$_3$)—C(=S)— | 1 (as) | 56 | 1765, 1670, 1600 | 3.4 (m, 2 + 3H), 3.95 (s, 3H), 4.35 (q, 2H), 5.50 (s, 1H), 6.85 (d, 2H), 7.7 (dd, 1H), 8.32 (s, 1H) |

EXAMPLE 92

Sodium 7-β-{D-α-[(4-hydroxy-2-p-methylaminosulfonylanilino-5-pyrimidinyl)-ureido]-p-hydroxyphenylacetamido}-7-α-methoxy-3-[(1-methyl-tetrazol-5-yl)-thiomethyl]-ceph-3-em-4-carboxylate 965 mgm pf diphenylmethyl 7-β-{D-α-[(4-hydroxy-2-p-methylaminosulfonylanilino-5-pyrimidinyl)-ureido]-p-hydroxyphenylacetamido}-3-[(1-methyl-tetrazol-5-yl)-thiomethyl]-ceph-3-em-4-carboxylate (intermediate of Example 70) were dissolved in a mixture of 40 ml of anhydrous methanol and 40 ml of anhydrous chloroform. The solution was cooled to −70° C., and 5 ml of a methanolic solution of lithium methoxide (1.5 mmols/ml) were added. After stirring for 3 minutes at −70° C., 0.18 ml of tert. butyl hypochlorite were added, and after stirring for another 20 minutes first 0.3 ml of acetic acid and then 0.1 ml of triethylphosphite were added. The temperature was allowed to rise to 20° C., whereupon the solution was evaporated to dryness, the residue was stirred briefly with water at pH 7, and the mixture was suction-filtered. The filter cake was purified by column chromatography on a Merck column (silicagel, methylene chloride/methanol 7:1).

480 mgm of the diphenylmethyl ester of the desired compound were obtained which, analogous to the preceding examples was split with trifluoroacetic acid/anisole and converted into the sodium salt.

IR-spectrum: 1765, 1660, 1605 cm$^{-1}$. NMR-spectrum (DMSO+CD$_3$OD) signals at ppm: 2.45 (s,3H), 3.25-3.50 (m, 2H+s, 3H), 3.95 (s, 3H), 4.30 (q, 2H), 4.95 (s, 1H), 5.45 (s, 1H), 6.75 (d, 2H), 7.30 (d, 2H), 7.80 (q, 4H), 8.35 (s, 1H).

EXAMPLE 93

Separation of the diastereoisomers of the cephalosporin of Example 22, Sodium 7-{D,L-α-[(2-p-aminosulfonylanilino-4-hydroxy-5-pyrimidinyl)-ureido]-2-thienylacetamido}-3-[(1-methyl-tetrazol-5-yl)-thiomethyl]-ceph-3-em-4-carboxylate.

The D,L-compound obtained in Example 22 was separated into the D and L form by preparative liquid chromatography (HPLC), using a 10 μm reversed phase-C 8-column (Lichrosorb RP 18, Merck). A solution of 6 gm of diammonium phosphate in 800 ml of water and 400 ml of methanol was used as eluant. The eluate was analyzed at 269 nm (UV).

The separated solutions were further processed as follows:

The methanol was removed in vacuo, and the remaining aqueous solution was adjusted to pH 3.0 with dilute hydrochloric acid. The precipitated solid product was suction-filtered off and dried.

Diastereoisomer I: NMR-spectrum (DMSO+CD$_3$OD) signals at ppm: 3.4 (m, 2H), 3.95 (s, 3H), 4.4 (m, 2H), 5.0 (d, 1H), 5.6 (d, 1H), 5.75 (s, 1H), 7.0 (m, 2H), 7.4 (d, 1H), 7.7 (d, 2H), 8.0 (d, 2H), 8.37 (s, 1H).

Diastereoisomer II: NMR-spectrum (DMSO+CD$_3$OD) signals at ppm: 3.4 (m, 2H), 3.95 (s, 3H), 4.45 (m, 2H), 5.05 (d, 1H), 5.65 (d, 1H), 5.80 (s, 1H), 7.0 (m, 2H), 7.35 (d, 1H), 7.7 (d, 2H), 8.0 (d, 2H), 8.37 (s, 1H).

Analogous to this example, the following D,L compounds were also separated into their D and L isomers:

Sodium 7-{D,L-α-[(2-cyclopropyl-4-hydroxy-5-pyrimidinyl)-ureido]-2-thienylacetamido}-3-[(1-methyltetrazol-5-yl)l-thiomethyl]-ceph-3-em-4-carboxylate;

Sodium 7-{D,L-α-[(4-hydroxy-2-(4'-hydroxy-cyclohexylamino)-5-pyrimidinyl)-ureido]-2-thienylacetamido}-3-[(1-methyl-tetrazol-5-yl)-thiomethyl]-ceph-3-em-4-carboxylate;

Sodium 7-β-{D,L-α-[(4-hydroxy-2-propylamino-5-pyrimidinyl)-ureido]-2-thienyl-acetamido}-7-α-methoxy-3-[(1-methyl-tetrazol-5-yl)-thiomethyl]-ceph-3-em-4-carboxylate;

Sodium 7-{D,L-α-[(2-(3'-aminosulfonylpropylamino)-4-hydroxy-5-pyrimidinyl)-ureido]-2-thienyl-acetamido}-3-[(1-methyl-tetrazol-5-yl)-thiomethyl]-ceph-3-em-4-carboxylate;

Sodium 7-β-{D,L-α-[(2-p-aminosulfonylanilino-4-hydroxy-5-pyrimidinyl)-ureido]-2-thienylacetamido}-7-α-methoxy-3-[(1-methyl-tetrazol-5-yl)-thiomethyl]-ceph-3-em-4-carboxylate;

Sodium 7-β-{D,L-α-[(2-p-aminosulfonylanilino-4-hydroxy-5-pyrimidinyl)-ureido]-2-thienyl-acetamido}-7-α-methoxy-3-amino-carbonyloxymethyl-ceph-3-em-4-carboxylate; and Sodium 7-{D,L-α-[(2-p-aminosulfonylanilino-4-hydroxy-5-pyrimidinyl)-ureido]-2-furylacetamido}-3-[(1-methyltetrazol-5-yl)-thiomethyl]-ceph-3-em-4-carboxylate.

EXAMPLE 94

Sodium 7-{D-α-[(4-hydroxy-5-pyrimidinyl)-ureido]-phenylacetamido}-3-methyl-ceph-3-em-4-carboxylate A suspension of 2.66 gm (0.0073 mol) of cephalexin monohydrate in 80 ml of tetrahydrofuran and 20 ml of water was caused to form a solution by adding triethylamine while cooling with ice.

800 mgm (0.0073 mol) of 5-amino-4-hydroxy-pyrimidine were dissolved in tetrahydrofuran, the solution was admixed with 1 ml of triethylamine, and the mixture was added dropwise, while cooling with ice, to a solution of 750 mgm of phosgene in 18 ml of tetrahydrofuran. The resulting mixture was evaporated in vacuo to 40 ml and was added dropwise, while cooling with ice, to the above prepared cephalexin solution, while keeping the pH at 7.5 with triethylamine. After stirring the resulting solution for one hour at 5° C. and for another hour at room temperature, the tetrahydrofuran was removed in vacuo, and the residue was diluted with 20 ml of water and extracted twice with ethyl acetate. Subsequently, the aqueous phase was covered with ethyl acetate, and a pH of 2.5 was slowly adjusted while cooling and stirring. The ethyl acetate layer was separated, the aqueous phase was again extracted with ethyl acetate, the two organic phases were combined, and the solvent was distilled off in vacuo.

The sodium salt was prepared in conventional manner.

Yield: 2.49 gm (68%).

IR-spectrum: 1760, 1655, 1610, 1540 cm$^{-1}$, NMR-spectrum (DMSO+CD$_3$OD) signals at ppm: 2.0 (s, 3H), 3.40 (q, 2H), 5.05 (d, 1H), 5.45 (s, 1H), 5.65 (d, 1H), 7.45 (m, 5H), 8.1 (s, 1H) 8.50 (s, 1H).

Using a procedure analogous to that described in Example 94, the cephalosporin salts named in Examples 95–97 were prepared from cephalexin monohydrate and the reaction product of the indicated pyrimidine derivative with phosgene.

EXAMPLE 95

Sodium 7{D-α-[(2-cyclopropyl-4-hydroxy-5-pyrimidinyl)-ureido] phenyl-acetamido}-3-methyl-ceph-3-em-4-carboxylate With the above reaction product of 5-amino-2-cyclopropyl-4-hydroxy-pyrimidine and phosgene:

Yield: 81%.

IR-spectrum: 1760, 1660, 1610, 1540 cm$^{-1}$, NMR-spectrum (DMSO+CD$_3$OD) signals at ppm: 1.0 (m, 4H), 1.9 (m, 1H), 2.0 (s, 3H), 3.4 (q, 2H), 4.95 (d, 1H), 5.45 (s, 1H), 5.60 (d, 1H), 7.4 (s, 5H), 8.4 (s, 1H).

EXAMPLE 96

Sodium 7-{D-α-[(4-hydroxy-2-(4'-hydroxy-cyclohexylamino)-5-pyrimidinyl)-ureido] phenyl-acetamido}-3-methyl-ceph-3-em-4-carboxylate With the reaction product of 5-amino-(4'-hydroxycyclohexylamino)-pyrimidine and phosgene (after silylation).

Yield: 64%.

IR-spectrum: 1760, 1660, 1610, 1550 cm$^{-1}$, NMR-spectrum (DMSO+CD$_3$OD) signals at ppm: 1.8 (m, 8H), 2.05 (s, 3H), 3.4 (q, 2H), 3.6-4.0 (broad m, 1H+1H), 4.95 (d, 1H), 5.45 (s, 1H), 5.65 (d, 1H), 7.4 (s, 5H), 8.05 (s, 1H).

EXAMPLE 97

Sodium 7-{D-α-[(2-p-chlorobenzylamino-4-hydroxy-5-pyrimidinyl)-ureido]phenyl-acetamido}-3-methyl-ceph-3-em-4-carboxylate With the reaction product of 5-amino-2-p-chlorobenzylamino-4-hydroxy-pyrimidine and phosgene.

Yield: 71%.

IR-spectrum: 1760, 1655, 1610, 1545 cm$^{-1}$, NMR-spectrum (DMSO+CD$_3$OD) signals at ppm: 2.0 (s, 3H), 3.35 (q, 2H), 4.95 (d, 1H), 5.4 (s, 1H), 5.65 (d, 1H), 6.8 (d, 2H), 7.4 (m, 7H), 8.0 (s, 1H).

EXAMPLE 98

Sodium 7-{D-α-[(2,4-dihydroxy-5-pyrimidinyl)-ureido]-p-hydroxyphenyl-acetamido}-3-acetoxymethyl-ceph-3-em-4-carboxylate 635 mgm (0.005 mol) of 5-amino-2,4-dihydroxypyrimidine were suspended in 50 ml of tetrahydrofuran and the suspension was treated with trimethylsilyl diethylamine until a solution was obtained. After distilling off the tetrahydrofuran in vacuo the residue was dissolved in 30 ml of tetrahydrofuran, and the mixture was added dropwise to a solution of 500 mgm of phosgene in tetrahydrofuran, while cooling with ice. Subsequently, nitrogen was blown through the solution to remove unreacted phosgene.

The further reaction was carried out analogous to Example 94 with 7-[D-α-amino-p-hydroxy-phenylacetamido]-3-acetoxymethyl-ceph-3-em-4-carboxylic acid.

Yield of the sodium salt: 830 mgm (29%).

IR-spectrum: 1760, 1665, 1505, 1545 cm$^{-1}$, NMR-spectrum (DMSO+CD$_3$OD) signals at ppm: 2.05 (s, 3H), 3.55 (q, 2H), 4.8 (m, 2+1H), 5.45 (s, 1H), 5.65 (d, 2H), 6.75 (d, 2H), 7.3 (d, 2H), 8.15 (s, 1H).

EXAMPLE 99

Sodium 7-{D-α-[(2-amino-4-hydroxy-5-pyrimidinyl)-ureido]-phenyl-acetamido}-3-methyl-ceph-3-em-4-carboxylate This compound was prepared from the phosgene adduct of 2,5-diamino-4-hydroxy-pyrimidine (after silylation, as described in Example 98) and cephalexin monohydrate. The cephalosporin thus obtained was precipitated from water at pH 3.0, suction-filtered, dried and converted into the sodium salt as described above.

Yield: 26%.

IR-spectrum: 1760, 1665, 1615, 1545 cm$^{-1}$, NMR-spectrum (DMSO+CD$_3$OD) signals at ppm: 2.0 (s, 3H), 3.45 (q, 2H), 4.90 (d, 1H), 5.40 (s, 1H), 5.60 (d, 2H), 7.4 (m, 5H), 8.0 (s, 1H).

EXAMPLE 100

Sodium 7-{D-α-[(4-hydroxy-2-methylamino-5-pyrimidinyl)-ureido]-p-hydroxy-phenyl-acetamido}-3-[(1-methyl-tetrazol-5-yl)-thiomethyl]-ceph-3-em-4-carboxylate This compound was prepared analogous to Example 98, starting from 405 mgm (0.001 mol) of 7-[D-α-amino-(p-hydroxyphenyl-acetamido)]-3-[(1-methyl-tetrazol-5-yl)-thiomethyl]-ceph-3-em-4-carboxylic acid and the reaction product of phosgene with 140 mgm (0.001 mol) of 5-amino-4-hydroxy-2-methylamino-pyrimidine. The cephalosporin thus obtained was precipitated from water at pH 2.8, suction-filtered, dried and converted into the sodium salt in the usual manner.

Yield: 315 mgm (31.5%).

IR-spectrum: 1760, 1655, 1610, 1540 cm$^{-1}$, NMR-spectrum (DMSO+CD$_3$OD) signals at ppm: 2.85 (s, 3H), 3.5 (q, 2H), 3.9 (s, 3H), 4.35 (q, 2H), 4.85 (d, 1H), 5.45 (s, 1H), 5.65 (d, 1H), 6.85 (d, 2H), 7.35 (d, 2H), 8.05 (s, 1H).

EXAMPLE 101

Sodium 7-{D-α-[(4-hydroxy-2-methoxy-5-pyrimidinyl)-ureido]-p-hydroxy-phenylacetamido}-3-[(1-methyl-tetrazol-5-yl)-thiomethyl]-ceph-3-em-4-carboxylate This compound was prepared analogous to Example 94, starting from the reaction product of 280 mgm (0.002 mol) of 5-amino-4-hydroxy-2-methoxy-pyrimidine with phosgene, and 920 mgm (0.002 mol) of 7-[D-α-amino-p-hydroxy-phenylacetamido]-3-[(1-methyl-tetrazol-5-yl)-thiomethyl]-ceph-3-em-4-carboxylate.

Yield of the sodium salt: 735 mgm (53%).

IR-spectrum (DMSO+CD$_3$OD) signals at ppm: 3.5 (q, 2H), 3.85 (s, 3H), 3.95 (s, 3H), 4.35 (q, 2H), 4.85 (d, 1H), 5.45 (s, 1H), 5.65 (d, 1H), 6.85 (d, 2H), 7.35 (d, 2H), 8.1 (s, 1H).

EXAMPLE 102

Sodium 7-{D-α-[(4-hydroxy-2-propylamino-5-pyrimidinyl)-ureido]-p-hydroxyphenylacetamido}-3-[(1-methyl-tetrazol-5-yl)-thiomethyl]-ceph-3-em-4-carboxylate This compound was prepared analogous to Example 33, starting from the reaction product of 1.70 gm (0.01 mol) of 5-amino-4-hydroxy-2-propylamino-pyrimidine with phosgene, and 4.61 gm (0.01 mol) of the cephalosporin used in Example 101. The further processing was carried out analogous to Example 99.

Yield of the sodium salt: 4.0 gm (61%).

IR-spectrum: 1760, 1660, 1610, 1540 cm$^{-1}$, NMR-spectrum (DMSO+CD$_3$OD) signals at ppm: 1.0 (t, 3H), 1.65 (q, 2H), 3.2 (t, 2H), 3.50 (q, 2H), 3.9 (s, 3H), 4.35 (q, 2H), 4.85 (d, 1H), 5.50 (s, 1H), 5.65 (d, 1H), 6.85 (d, 2H), 7.35 (d, 2H), 8.0 (s, 1H).

EXAMPLE 103

Sodium 7-{D-α-[(4-hydroxy-2-isopropylamino-5-pyrimidinyl)-ureido]-p-hydroxy-phenylacetamido}-3-acetoxymethyl-ceph-3-em-4-carboxylate This compound was prepared analogous to Example 98, starting from the reaction product of 505 mgm (0.003 mol) of 5-amino-4-hydroxy-2-isopropylamino-pyrimidine with trimethylsilyl diethylamine and phosgene, and 1.22 gm (0.003 mol) of the cephalosporin derivative of Example 98.

The further reaction was carried out analogous to Example 99.

Yield of the sodium salt: 980 mgm (61%).

IR-spectrum: 1760, 1660, 1615, 1535 cm$^{-1}$, NMR-spectrum (DMSO+CD$_3$OD) signals at ppm: 1.15 (d, 6H), 2.05 (s, 3H), 3.55 (q, 2H), 3.90 (broad, 1H), 4.80 (m, 2+1H), 5.45 (s, 1H), 5.65 (d, 1H), 6.85 (d, 2H), 7.3 (d, 2H), 8.0 (s, 1H).

EXAMPLE 104

Sodium 7-{D,L-α-[(4-hydroxy-2-propylamino-5-pyrimidinyl)-ureido]-2-thienyl-acetamido}-3-[(1-methyl-tetrazol-5-yl)-thiomethyl]-ceph-3-em-4-carboxylate 1 ml of bis-trimethyl-silylacetamide was added to a suspension of 435 mgm (0.00093 mol) of 7-(D,L-α-amino-2-thienyl-acetamido)-3-[(1-methyl-tetrazol-5-yl)-thiomethyl]-ceph-3-em-4-carboxylic acid in 10 ml of dry acetonitrile. After a homogeneous solution had been formed, a solution of the reaction product of 160 mgm (0.00095 mol) of 5-amino-4-hydroxy-2-propylamino-pyrimidine with trimethylsilyldiethylamine and 950 mgm of phosgene in tetrahydrofuran was added dropwise.

The further reaction was carried out analogous to Example 99.

Sodium 7-{D-α-[(2-ethylamino-4-hydroxy-5-pyrimidinyl)-ureido]-p-hydroxy-phenylacetamido}-3-[(2-methylaminothiadiazol-5-yl)-thiomethyl]-ceph-3-em-4-carboxylate was prepared in analogous manner.

EXAMPLE 105

Sodium 7-{D-α-[(2-allylamino-4-hydroxy-5-pyrimidinyl)-ureido]-phenyl-acetamido}-3-acetoxymethyl-ceph-3-em-4-carboxylate This compound was prepared analogous to Example 94, starting from the reaction product of 332 mgm (0.002 mol) of 5-amino-2-allylamino-4-hydroxy-pyrimidine with 200 mgm of phosgene, and 850 mgm (0.002 mol) of cephaloglycin dihydrate. The further processing was carried out analogous to Example 98.

Yield of the sodium salt: 680 mgm (56.6%).

IR-spectrum: 1760, 1660, 1610, 1540 cm$^{-1}$, NMR-spectrum (DMSO+CD$_3$OD) signals at ppm: 2.05 (s, 3H), 3.4 (q, 2H), 3.9 (broad signal, 2H), 4.85 (m, 2H+d, 1H), 5.0-5.5 (m, 3H), 5.45 (s, 1H), 5.65 (d, 1H), 6.0 (m, 1H), 7.45 (5H), 8.05 (s, 1H).

EXAMPLE 106

Sodium 7-{D-α-[(2-allylamino-4-hydroxy-5-pyrimidinyl)-ureido]-phenylacetamido}-3-[(1-methyl-tetrazol-5-yl)-thiomethyl]-ceph-3-em-4-carboxylate This compound was prepared analogous to Example 94, starting from 3.2 gm (0.005 mol) of the corresponding cephalosporin derivative and the reaction product of 0.83 gm (0.005 mol) of 5-amino-2-allylamino-4-hydroxypyrimidine with 500 mgm of phosgene.

Yield of the sodium salt: 1.52 gm (48%).

IR-spectrum: 1760, 1660, 1615, 1545 cm$^{-1}$, NMR-spectrum (DMSO+CD$_3$OD) signals at ppm: 3.5 (q, 2H), 3.95 (s,3H+broad signal 2H), 4.4 (q, 2H), 4.85 (d, 1H), 5.0-5.5 (m, 4H), 5.65 (d, 1H), 5.95 (m, 1H), 7.45 (m, 5H), 8.0 (s, 1H).

The following compounds were prepared in analogous manner:

Sodium 7-{D-α-[(2-(3'-methylallylamino)-4-hydroxy-5-pyrimidinyl)-ureido]-p-hydroxy-phenylacetamido}-3-[(1,2,4-thiadiazol-5-yl)-thiomethyl]-ceph-3-em-4-carboxylate;

Sodium 7-{D-α-[(4-hydroxy-2-propargylamino-5-pyrimidinyl)-ureido]-p-hydroxy-phenylacetamido}-3-[(2-dimethylamino-thiadiazol-5-yl)-thiomethyl]-ceph-3-em-4-carboxylate;

Sodium 7-{D-α-[(2-cyclopropylamino-4-hydroxy-5-pyrimidinyl)-ureido]-p-hydroxy-phenylacetamido}-3-[(1-methyl-tetrazol-5-yl)-thiomethyl]-ceph-3-em-4-carboxylate;

Sodium 7-{D-α-[(2-cyclopropylmethylamino-4-hydroxy-5-pyrimidinyl)-ureido]-p-hydroxy-phenylacetamido}-3-[(1-methyl-tetrazol-5-yl)-thiomethyl]-ceph-3-em-4-carboxylate;

Sodium 7-{D-α-[(2-cyclohexylamino-4-hydroxy-5-pyrimidinyl)-ureido]-p-hydroxy-phenylacetamino}-3-[(1-methyl-tetrazol-5-yl)-thiomethyl]-ceph-3-em-4-carboxylate; and Sodium 7-{D-α-[(2-cyclohexylamino-4-hydroxy-5-pyrimidinyl)-ureido]-p-hydroxyphenylacetamido}-3-[(1,2,4-thiadiazol-5-yl)-thiomethyl]-ceph-3-em-4-carboxylate.

EXAMPLE 107

Sodium 7-{D-α-[(4-hydroxy-2-(4'-hydroxy-cyclohexylamino)-5-pyrimidinyl)-ureido]-p-hydroxy-phenylacetamido}-3-acetoxy-methyl-ceph-3-em-4-carboxylate This compound was prepared analogous to Example 98, starting from 810 mgm (0.002 mol) of 7-(D-α-amino-p-hydroxy-phenylacetamido)-3-acetoxymethyl-ceph-3-em-4-carboxylate and the reaction product of 450 mgm (0.002 mol) of 5-amino-4-hydroxy-2-(4'-hydroxy-cyclohexylamino)-pyrimidine with trimethylsilyl-diethylamine and 200 mgm of phosgene.

The further processing was carried out analogous to Example 99.

Yield of the sodium salt: 615 mgm (44.5%).

IR-spectrum: 1760, 1660, 1540 cm$^{-1}$, NMR-spectrum (DMSO+CD$_3$OD) signals at ppm: 1.75 (m, 8H), 2.05 (s, 3H), 3.35 (q, 2H), 3.5-4.0 (m, 1+1H), 4.80 (m, 2+1H), 5.45 (s, 1H), 5.65 (d, 1H), 6.8 (d, 2H), 7.35 (d, 2H), 8.0 (s, 1H).

EXAMPLE 108

Sodium 7-{D-α-[(4-hydroxy-2-(2'-methoxy-ethylamino)-5-pyrimidinyl)-ureido]-p-hydroxy-phenylacetamido}-3-[(1-methyl-tetrazol-5-yl)-thiomethyl]-ceph-3-em-4-carboxylate This compound was prepared analogous to Example 94, starting from 550 mgm (0.00123 mol) of the cephalosporin of Example 3 and 220 mgm (0.0012 mol) of 5-amino-4-hydroxy-2-(2'-methoxy-ethylamino)-pyrimidine.

The further processing was carried out analogous to Example 99.

Yield of the sodium salt: 450 mgm (59%).

IR-spectrum: 1760, 1660, 1610, 1540 cm$^{-1}$, NMR-spectrum (DMSO+CD$_3$OD) signals at ppm: 3.0-3.5 (m, 2+2+2H), 3.55 (s, 3H), 3.9 (s, 3H), 4.35 (q, 2H), 4.85 (d, 1H), 5.45 (s, 1H), 5.65 (d, 1H), 6.8 (d, 2H), 7.35 (d, 2H), 8.0 (s, 1H).

Sodium 7-}D-α-[(4-hydroxy-2-(2'-methoxy-ethylamino)-5-pyrimidinyl)-ureido]-p-hydroxy-phenylacetamido}-3-[(1,3,4-thiadiazol-5-yl)-thiomethyl]-ceph-3-em-4-carboxylate was prepared in analogous manner.

EXAMPLE 109

Sodium 7-{D-α-[(4-hydroxy-2-(3'-hydroxypropylamino)-5-pyrimidinyl)-ureido]-p-hydroxyphenylacetamido}-3-acetoxy-methyl-ceph-3-em-4-carboxylate This compound was prepared analogously to Example 98, starting from 1.84 gm (0.01 mol) of the reaction product of 5-amino-2-(3'-hydroxy-propylamino)-4-hydroxy-5-pyrimidine with trimethylsilyl-diethylamine and 1 gm of phosgene, and 4.05 gm (0.01 mol) of 7-D-α-amino-p-hydroxy-phenylacetamido-3-acetoxymethyl-ceph-3-em-4-carboxylic acid.

Yield of the sodium salt: 3.65 gm (50%).

IR-spectrum: 1760, 1670, 1620, 1550 cm$^{-1}$, NMR-spectrum (DMSO+CD$_3$OD) signals at ppm: 1.85 (m, 2H), 2.05 (s, 3H), 3.0-3.7 (m, 2+2+2H), 4.85 (m, 2+1H), 5.40 (s, 1H), 5.55 (d, 1H), 6.85 (d, 2H), 7.3 (d, 2H), 8.05 (s, 1H).

The following compounds were prepared in analogous manner, starting from the same cephalosporin derivative:

Sodium 7-}D-α-[(2-p-hydroxybenzylamino-4-hydroxy-5-pyrimidinyl)-ureido]-p-hydroxy-phenylacetamido}-3-acetoxymethyl-ceph-3-em-4-carboxylate;

Sodium 7-{D-α-[(4-hydroxy-2-m,p-dioxymethylenebenzylamino-5-pyrimidinyl)-ureido]-p-hydroxy-phenylacetamido}-3-acetoxymethyl-ceph-3-em-4-carboxylate; and Sodium 7-{D-α-[(2-p-dimethylamino-anilino-4-hydroxy-5-pyrimidinyl)-ureido]-p-hydroxy-phenylacetamido}-3-acetoxymethyl-ceph-3-em-4-carboxylate.

EXAMPLE 110

Sodium 7-{D-α-[(4-hydroxy-2-p-hydroxy-anilino-5-pyrimidinyl)-ureido]-p-hydroxy-phenylacetamido}-3-[(1-methyl-tetrazol-5-yl)-thiomethyl]-ceph-3-em-4-carboxylate This compound was prepared analogous to Example 98, starting from 218 mgm (0.001 mol) of 5-amino-4-hydroxy-2-p-hydroxy-anilino-pyrimidine which, after reaction with trimethylsilyl-diethylamine and phosgene, was reacted with 460 mgm (0.001 mol) of the corresponding cephalosporin derivative of Example 108.

Yield of the sodium salt: 280 mgm (38.5%).

IR-spectrum: 1760, 1660, 1610, 1540 cm$^{-1}$, NMR-spectrum (DMSO+CD$_3$OD) signals at ppm: 3.5 (q, 2H), 3.9 (s, 3H), 4.35 (q, 2H), 4.85 (d, 1H), 5.40 (s, 1H), 5.60 (d, 2H), 6.8 (d, 2H), 7.4 (m, 4H), 7.7 (d, 2H), 8.30 (s, 1H).

Using a procedure analogous to that described in Example 98 or 99, the cephalosporins of the formula

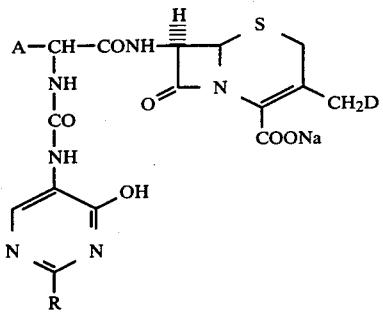

shown in the following table were also prepared:

TABLE VII

| Example No. | A | R | D | Yield % | IR-spectrum cm$^{-1}$ | NMR-spectrum (DMSO + CD$_3$OD) |
|---|---|---|---|---|---|---|
| 111 | HO—⌬— | NHCH$_2$—⌬ | OCOCH$_3$ | 62 | 1760, 1660, 1605 | 2.05 (s, 3H), 3.40 (q, 2H), 4.2 (bs, 2H), 4.8 (m, 2H), 4.9 (d, 1H), 5.5 (s, 1H), 5.6 (d, 1H), 6.80 (d, 2H), 7.4 (m, 7H), 8.05 (s, 1H) |
| 112 | HO—⌬— | NHCH$_2$—⌬—SOCH$_3$ | tetrazole-S-CH$_3$ | 49.5 | 1760, 1655, 1600, 1150 | 2.7 (s, 3H), 3.4 (q, 2H), 3.95 (s, 3H), 4.4 (m, 2 + 2H), 4.95 (d, 1H), 5.5 (s, 2H), 5.65 (d, 1H), 6.85 (d, 2H), 7.35 (m, 4H), 7.7 (d, 2H), 8.05 (s, 1H) |
| 113 | HO—⌬— | NH—⌬—SO$_2$NH$_2$ | tetrazole-S-CH$_3$ | 57 | 1760, 1650, 1600, 1150 | 3.35 (q, 2H), 3.95 (s, 3H), 4.3 (q, 2H), 5.0 (d, 1H), 5.55 (s, 1H), 5.65 (d, 1H), 6.85-7.0 (m, 3H) 7.3 (m, 3H), 8.31 (s, 1H) 8.75 (s, 1H) |
| 114 | HO—⌬— | NH—⌬ | OCOCH$_3$ | 56 | 1760, 1660, 1600 | 2.05 (s, 3H), 3.4 (q, 2H), 4.8 (m, 2 + 1H), 5.50 (s, 1H), 5.60 d, 1H), 6.85 (d, 2H), 7.3-7.7 (m, 7H), 8.30 (s, 1H) |
| 115 | HO—⌬— | NH—⌬—NHCOCH$_3$ | OCOCH$_3$ | 64.5 | 1760, 1655, 1599 | 2.05 (s, 3H), 2.1 (s, 3H), 3.4 (q, 2H), 4.7-5.0 (m, 2 + 1H) 5.5 (s, 1H), 5.65 (d, 1H), 6.75 (d, 2H), 7.3-7.5 (m, 4H), 7.7 (d, 2H), 8.3 (s, 1H) |

TABLE VII-continued

| Example No. | A | R | D | Yield % | IR-spectrum cm$^{-1}$ | NMR-spectrum (DMSO + CD$_3$OD) |
|---|---|---|---|---|---|---|
| 116 | HO—⟨⟩— | NH—⟨⟩—SOCH$_3$ | OCOCH$_3$ | 47 | 1760, 1665, 1610 | 2.05 (s, 3H), 2.75 (s, 3H), 3.4 (q, 2H), 4.7–5.0 (m, 2 + 1H), 5.60 (d, 1H), 6.75 (d, 2H), 7.2–8.0 (m, 6H), 8.35 (s, 1H) |
| 117 | ⟨S⟩—D,L | NH—⟨⟩—CONH$_2$ | N——N ∥ N—N(CH$_3$) | 62 | 1760, 1660, 1600 | 3.35 (m, 2H), 3.95 (s, 3H), 4.3 (q, 2H), 5.05 (dd, 1H), 5.60 (dd, 1H), 5.70 (d, 1H), 7.0 (m, 2H), 7.4 (m, 1H), 7.75 (m, 4H), 8.35 (s, 1H) |
| 118 | HO—⟨⟩— | NH—⟨⟩—NHCONH$_2$ | OCOCH$_3$ | 60 | 1760, 1665, 1610 | 2.05 (s, 3H), 3.4 (q, 2H), 4.8 (m, 2H + 1H), 5.5 (s, 1H), 5.6 (d, 1H), 6.80 (d, 2H), 7.35 (dd, 4H), 7.6 (d, 2H), 8.2 (s, 1H) |
| 119 | HO—⟨⟩— | NHCOCH$_3$ | OCOCH$_3$ | 49 | 1760, 1650, 1600 | 2.05 (s, 3H), 2.25 (s, 3H), 3.45 q, 2H), 4.8 (m, 2H), 5.0 (d, 1H), 5.5 (s, 1H), 5.6 (d, 1H), 6.85 (d, 2H), 7.35 (d, 2H), 8.25 (s, 1H) |
| 120 | ⟨⟩— | NH—⟨⟩—SO$_2$NH$_2$ | CH$_3$ | 71 | 1760, 1660, 1610, 1150 | 2.0 (s, 3H), 3.4 (q, 2H), 4.95 (d, 1H), 5.45 (s, 1H), 5.60 (d, 1H), 7.4 (broad s, 5H), 7.7 (d, 2H), 8.0 (d, 2H), 8.37 (s, 1H) |

EXAMPLE 121

Sodium 7-{D-α-[(4-hydroxy-2-isopropylamino-5-pyrimidinyl)-ureido]-p-hydroxy-phenylacetamido}-3-[(2-methyl-oxadiazol-5-yl)-thiomethyl]-ceph-3-em-4-carboxylate 360 mgm of the cephalosporin derivative obtained in Example 103 were dissolved in 10 ml of a phosphoric acid buffer solution of pH 6.3. After adding 70 mgm of 5-methyl-2-mercapto-1,3,4-oxadiazole thereto, the reaction mixture was heated for 6 hours at 70° C. in an atmosphere of nitrogen, while keeping the pH at 6.0–6.5. After cooling the reaction mixture and extracting it twice with ethyl acetate, the pH was adjusted to 2.9 by addition of 2 N hydrochloric acid while cooling. The precipitated product was suction-filtered off, washed with a little water and dried. The residue was converted into the sodium salt in conventional manner.

Yield: 235 mgm (61%).

IR-spectrum: 1760, 1660, 1615, 1545 cm$^{-1}$, NMR-spectrum (DMSO+CD$_3$OD) signals at ppm: 1.15 (d, 6H), 2.45 (s, 3H), 3.6 (q, 2H), 3.9 (m, broad 1H), 4.2 (q, 2H, partly covered by LM), 4.95 (d, 1H), 5.45 (s, 1H), 5.60 (d, 1H), 6.8 (d, 2H), 7.35 (d, 2H), 8.0 (s, 1H).

Sodium 7-{D-α-[(4-hydroxy-2-isopropylamino-5-pyrimidinyl)-ureido]-p-hydroxy-phenylacetamido}-3-[(1,2,3-triazol-4-yl)-thiomethyl]-ceph-3-em-4-carboxylate was prepared analogously from the same cephalosporin derivative with 4-mercapto-1,2,3-triazol.

Yield: 56%.

EXAMPLE 122

Sodium 7-{D-α-[(4-hydroxy-2-(4'-hydroxy-cyclohexylamino)-5pyrimidinyl)-ureido]-p-hydroxy-phenylacetamido}-3-[(1-methyl-tetrazol-5-yl)-thiomethyl]-ceph-3-em-4-carboxylate This compound was prepared analogous to Example 121, starting from 680 mgm of the cephalosporin derivative obtained in Example 107 by reacting it with 135 mgm of 5-mercapto-1-methyl-tetrazol.

Yield of the sodium salt: 410 mgm (58%).

IR-spectrum: 1760, 1660, 1610, 1535 cm$^{-1}$, NMR-spectrum (DMSO+CD$_3$OD) signals at ppm: 1.8 (m, 8H), 3.5 (q, 2H), 3.6–4.0 (broad m, 1+1H), 3.95 (s, 3H), 4.35 (q, 2H), 4.85 (d, 1H), 5.40 (s, 1H), 5.60 (d, 1H), 6.8 (d, 2H), 7.3 (d, 2H), 8.0 (s, 1H).

The following cephalosporins were prepared, starting from the cephalosporin derivative obtained in Example 107:

EXAMPLE 123

Sodium 7-{D-α-[(4-hydroxy-2-(4'-hydroxy-cyclohexylamino)-5-pyrimidinyl)-ureido]-p-hydroxy-phenylacetamido}-3-[(1,3,4-thiadiazol-5-yl)-thiomethyl]-ceph-3-em-4-carboxylate By reaction with 2-mercapto-1,3,4-thiadiazol.
Yield: 68.5%.

EXAMPLE 124

Sodium 7-{D-α-[(4-hydroxy-2-(4'-hydroxy-cyclohexylamino)-5-pyrimidinyl)-ureido]-p-hydroxy-phenylacetamido}-3-[(tetrazol-5-yl)-thiomethyl]-ceph-3-em-4-carboxylate By reaction with 5-mercapto-tetrazol.
Yield: 56%.

EXAMPLE 125

Sodium 7-{D-α-[(4-hydroxy-2-(3'-hydroxypropylamino)-5-pyrimidinyl)-ureido]-p-hydroxy-phenylacetamido}-3-[(2-methyl-1,3,4-oxadiazol-5-yl)-thiomethyl]-ceph-3-em-4-carboxylate This compound was prepared analogous to Example 121, starting from 640 mgm (0.001 mol) of the cephalosporin derivative obtained in Example 109 and reacting it with 180 mgm of 5-mercapto-2-methyl-1,3,4-oxadiazole.

Yield of the sodium salt: 455 mgm (65%).

IR-spectrum: 1760, 1670, 1615, 1550 cm$^{-1}$, NMR-spectrum (DMSO+CD$_3$OD) signals at ppm: 1.80 (m, 2H), 2.45 (s, 3H), 3.0-3.7 (m, 2+2+2H), 4.2 (q, 2H, partly covered by LM), 4.95 (d, 1H), 5.45 (s, 1H), 5.65 (d, 1H), 6.85 (d, 2H), 7.35 (d, 2H), 8.05 (s, 1H).

When the 3-acetoxymethylcephalosporin derivative obtained in Example 109 was used, the following cephalosporin derivatives were obtained:

EXAMPLE 126

Sodium 7-{D-α-[(4-hydroxy-2-(3'-hydroxypropylamino)-5-pyrimidinyl)-ureido]-p-hydroxy-phenylacetamido}-3-[(2-formylamino-thiadiazol-5-yl)-thiomethyl]-ceph-3-em-4-carboxylate By reaction with 2-formylamino-5-mercapto-thiadiazole.
Yield: 44%.

EXAMPLE 127

Sodium 7-{D-α-[(4-hydroxy-2-(3'-hydroxypropylamino)-5-pyrimidinyl)-ureido]-p-hydroxy-phenylacetamido}-3-[(1,2,4-thiadiazol-5-yl)-thiomethyl]-ceph-3-em-4-carboxylate By reaction with 5-mercapto-1,2,4-thiadiazole.
Yield 53%.

EXAMPLE 128

Sodium 7-{D-α-[(4-hydroxy-2-(3'-hydroxypropylamino)-5-pyrimidinyl)-ureido]-p-hydroxy-phenylacetamido}-3-(4-aminocarbonyl-pyridinium)-ceph-3-em-4-carboxylate By reaction with 4-aminocarbonyl-pyridine.
Yield: 38.5%.

EXAMPLE 129

Sodium 7-{D-α-[(4-hydroxy-2-(3'-hydroxypropylamino)-5-pyrimidinyl)-ureido]-p-hydroxy-phenylacetamido}-3-[(2-methylamino-thiadiazol-5-yl)-thiomethyl]-ceph-3-em-4-carboxylate By reaction with 2-methylamino-5-mercapto-1,3,4-thiadiazol.
Yield: 61%.

The following compounds were synthesized in analogous manner:

Sodium 7-{D-α-[(2-m,p-dioxymethylene-benzylamino-4-hydroxy-5-pyrimidinyl)-ureido]-p-hydroxy-phenylacetamido}-3-[(1-methyl-tetrazol-5-yl)-thiomethyl]-ceph-3-em-4-carboxylate;

Sodium 7-{D-α-[(p-dimethylamino-anilino-4-hydroxy-5-pyrimidinyl)-ureido]-p-hydroxy-phenylacetamido}-3-[(1-methyl-tetrazol-5-yl)-thiomethyl]-ceph-3-em-4-carboxylate;

Sodium 7-{D-α-[(p-dimethylamino-anilino-4-hydroxy-5-pyrimidinyl)-ureido]-p-hydroxy-phenylacetamido}-3-[(2-formylamino-1,3,4-thiadiazol-5-yl)-thiomethyl]-ceph-3-em-4-carboxylate;

Sodium 7-{D-α-[(p-dimethylamino-anilino-4-hydroxy-5-pyrimidinyl)-ureido]-p-hydroxy-phenylacetamido}-3-[(2-methyl-1,3,4-oxadiazol-5-yl)-thiomethyl]-ceph-3-em-4-carboxylate; and Sodium 7-{D-α-[(2-acetylamino-4-hydroxy-5-pyrimidinyl)-ureido]-p-hydroxy-phenylacetamido}-3-[(1-methyl-tetrazol-5-yl)-thiomethyl]-ceph-3-em-4-carboxylate.

EXAMPLE 130

7-{D-α-[(2-p-aminosulfonylanilino-4-hydroxy-5-pyrimidinyl)-ureido]-p-hydroxy-phenylacetamido}-3-[(4'-aminocarbonylpyridino)-methyl]-ceph-3-em-4-carboxylate A mixture of 2 mmols of the compound of Example 21, 3 mmols of 4-pyridine carboxamide, 4 gm of potassium thiocyanate and 5 ml of water was heated at 50° C. for 8 hours. The resulting solution was chromatographed on a column filled with the ion exchange resin Amberlite XAD-2, which was first washed with one liter of water. Subsequently, the desired compound was eluted with a mixture of water and methanol (7:3). The methanol was distilled out of the eluate, and the residual solution was freeze-dried. NMR-spectrum (D$_2$O): 3.6 (m, 2H), 5.1 (d, 1H), ~5.4 (q, 2H), 5.7 (s, 1H), 5.8 (d, 1H), 7.7 (d, 2H), 8.0 (d, 2H), 8.3 (d, 2H), 8.38 (s, 1H), 9.1 (d, 2H).

EXAMPLE 131

When pyridine was used in the procedure of Example 130 instead of 4-pyridine carboxamide, 7-{D-α-[(2-p-aminosulfonylanilino-4-hydroxy-5-pyrimidinyl)ureido]-p-hydroxy-phenylacetamido}-3-(pyridinomethyl)-ceph-3-em-4-carboxylate was obtained.

NMR-spectrum (D$_2$O): 3.65 (m, 2H), 5.1 (d, 1H), 5.45 (q, 2H), 5.7 (s, 1H), 5.8 (d, 1H), 7.7 (d, 2H), 8.05 (d, 2H), 8.1, 8.5, 8.9 (m, 5H), 8.38 (s, 1H).

EXAMPLE 132

7-{D-α-[(4-hydroxy-2-(3'-hydroxypropylamino)-5-pyrimidinyl)-ureido]-p-hydroxy-phenylacetamido}-3-[(4'-aminocarbonylpyridino)-methyl]-ceph-3-em-4-carboxylate This compound was prepared by reaction of the cephalosporin of Example 109 with 4-aminocarbonyl pyridine.

Yield: 38.5%.

Using a procedure analogous to that described in Example 121, the cephalosporin of the formula

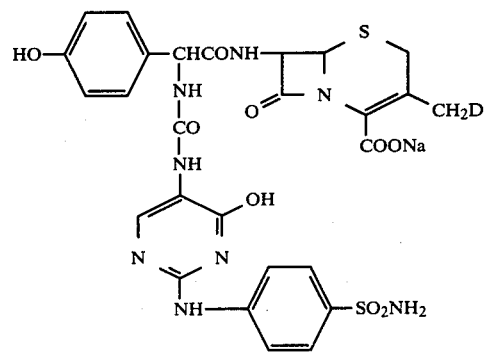

shown in the following table were prepared, starting from the cephalosporin of Example 21:

TABLE VIII

| Example No. | D | Yield % | IR-spectrum cm$^{-1}$ | NMR-spectrum |
|---|---|---|---|---|
| 133 | -S-C(=N-N=CH-)- (pyrazolyl-thio) | 46 | 1760, 1660, 1600, 1145 | 3.3 (q, 2H), 4.4 (q, 2H), 5.0 (d, 1H), 5.55 (s, 1H), 5.65 (d, 1H), 6.75 (d, 2H), 7.3 (d, 2H), 7.7 (d, 2H), 8.0 (d, 2H + 1, 1H) 8.37 (s, 1H) |
| 134 | -S-C(=N-N=C(N(CH$_3$)$_2$)-S-)- | 55 | 1765, 1665, 1610, 1150 | 2.90 (d, 6H), 3.4 (m, 2H), 4.35 ((q, 2H), 4.95 (d, 1H), 5.55 ((s, 1H), 5.65 (s, 1H), 6.75 (d, 2H), 7.3 (d, 2H), 7.65 (d, 2H), 7.95 (d, 2H), 8.38 (s, 1H) |
| 135 | -S-C(=N-N=C(NHCHO)-S-)- | 34.5 | 1760, 1660, 1630, 1610, 1150 | 3.3 (m, 2H), 4.3 (m, 2H), 5.0 (d, 1H), 5.55 (s, 1H), 5.65 (d, 1H), 6.75 (d, 2H), 7.35 (d, 2H), 7.7 (d, 2H), 8.0 (d, 2H), 8.37 (s, 1H) |
| 136 | -S-C(=N-N=C(NHCOCH$_3$)-S-)- | 41 | 1760, 1660, 1635, 1600, 1150 | 2.3 (s, 3H), 3.15 (m, 2H), 4.3 (q, 2H), 5.0 (d, 1H, 5.50 (s, 1H), 5.65 (d, 1H), 6.75 (d, 2H), 7.35 (d, 2H), 7.7 (d, 2H), 8.0 (d, 2H), 8.35 (s, 1H) |
| 137 | -S-C(=N-CH=N-S-)- | 72 | 1760, 1660, 1600, 1150 | 3.3 (m, 2H), 4.25 (q, 2H), 5.05 (d, 1H), 5.55 (s, 1H), 5.65 (d, 1H), 6.75 (d, 2H), 7.35 (d, 2H), 7.7 (d, 2H), 8.0 (d, 2H), 8.37 (s, 1H) |
| 138 | -S-C(=N-C(CH$_3$)=N-S-)- | 68 | 1760, 1655, 1595, 1145 | 2.5 (s, 3H), 3.3 (m, 2H), 4.25 ((q, 2H), 5.05 (d, 1H), 5.55 (s, 1H), 5.65 (d, 1H), 6.75 (d, 2H), 7.35 (d, 2H), 7.7 (d, 2H), 8.0 (d, 2H), 8.3 (s, 1H), 8.36 (s, 1H) |

Sodium 7-{D-α-[(2-anilino-4-hydroxy-5-pyrimidinyl)-ureido]-p-hydroxy-phenylacetamido}-3-[(1-methyl-tetrazol-5-yl)-thiomethyl]-ceph-3-em-4-carboxylate was prepared from the corresponding 3-acetoxymethyl compound in analogous manner.

EXAMPLE 139

Pivaloyloxymethyl 7-{D-α-[(2-cyclopropyl-4-hydroxy-5-pyrimidinyl)-ureido]-p-hydroxy-phenylacetamido}-3-[(1-methyl-tetrazol-5-yl)-thiomethyl]-ceph-3-em-4-carboxylate A solution of 900 mgm (0.0013 mol) of the sodium salt of Example 3 and 325 mgm of pivoloyloxymethyl iodide in 15 ml of dimethylformamide was stirred for one hour at room temperature. Subsequently, 50 ml of ethyl acetate and 50 ml of a 0.1 M sodium bicarbonate solution were added. The layer of ethyl acetate was then successively washed with water, dilute hydrochloric acid, water and a saturated sodium chloride solution, dried over magnesium sulfate and evaporated in vacuo to dryness. The residue was stirred with anhydrous ether and suction-filtered off.

Yield 670 mgm (66%).

IR-spectrum: 1770, 1735 cm$^{-1}$, NMR-spectrum (CDCl$_3$+CC$_3$OD) signals at ppm: 0.9 (m, 4H), 1.10 (s, 9H), 1.95 (m, 1H), 3.6 (m, 2H), 4.0 (s, 3H), 4.5 (m, 2H), 4.95 (d, 1H), 5.5 (s, 1H), 5.75 (d, 1H), 5.85 (dd, 2H), 6.9 (d, 2H), 7.4 (d, 2H), 8.4 (s, 1H).

The following esters were prepared in analogous manner:

Pivaloyloxymethyl 7-{D-α-[(4-hydroxy-2-isopropylamino-5-pyrimidinyl-ureido]-p-hydroxy-phenylacetamido}-3-[(1-methyl-tetrazol-5-yl)-thiomethyl]-ceph-3-em-4-carboxylate;

Acetyloxymethyl 7-{D-α-[(4-hydroxy-2-(4'-hydroxycyclohexylamino-5-pyrimidinyl)-ureido]-p-hydroxy-phenylacetamido}-3-[(1-methyl-tetrazol-5-yl)-thiomethyl]-ceph-3-em-4-carboxylate; and Pivaloyloxymethyl 7-{D-α-[(4-hydroxy-2-(3'-hydroxypropylamino-5-pyrimidinyl)-ureido]-p-hydroxy-phenylacetamido}-3-[(1-methyl-tetrazol-5-yl)-thiomethyl]-ceph-3-em-4-carboxylate.

EXAMPLE 140

Pivaloyloxymethyl 7-{D-α-[(4-hydroxy-2-(3'-methylallylamino-5-pyrimidinyl)-ureido]-p-hydroxy-phenylacetamido}-3-[(1-methyl-tetrazol-5-yl)-thiomethyl]-ceph-3-em-4-carboxylate This compound was prepared analogous to Example 139, starting from 3.4 gm of the sodium salt of Example 51, which was reacted with 1.2 gm of pivaloyloxymethyl iodide.

Yield: 2.62 gm (68%).

IR-spectrum: 1770, 1740 cm$^{-1}$, NMR-spectrum (CDCl$_3$+CD$_3$OD) signals at ppm: 1.10 (s, 9H), 1.75 (d, 3H), 3.55 (q, 2H), 3.85 (broad, 2H), 3.95 (s, 3H), 4.45 (m, 2H), 4.95 (d, 1H), 5.55 (s, 1H), 5.65 (m, 2+1H), 5.8 (dd, 2H), 5.75 (d, 2H), 7.35 (d, 2H), 8.0 (s, 1H).

EXAMPLE 141

Pivaloyloxymethyl 7-{D-α-[(2-p-aminosulfonylanilino-4-hydroxy-5-pyrimidinyl)-ureido]-p-hydroxy-phenylacetamido}-3-[(1-methyl-tetrazol-5-yl)-thiomethyl]-ceph-3-em-4-carboxylate This compound was prepared analogous to Example 139, starting from the sodium salt synthesized in Example 20, and reacting it with pivaloyloxymethyl iodide. Yield 64%.

IR-spectrum: 1770, 1730 cm$^{-1}$, NMR-spectrum (CDCH$_3$+CD$_3$OD) signals at ppm: 1.10 (s, 9H), 3.50 (q, 2H), 3.95 (s, 3H), 4.40 (q, 2H), 5.0 (d, 1H), 5.60 (s, 1H), 5.65 (d, 1H), 5.80 (dd, 2H), 6.75 (d, 2H), 7.3 (d, 2H), 7.7 (d, 2H), 8.0 (d, 2H), 8.38 (s, 1H).

EXAMPLE 142

Sodium 7-{D-α-[(4-hydroxy-2-p-methylsulfonylanilino-5-pyrimidinyl)-ureido]-p-hydroxy-phenylacetamido}-3-[(1-methyl-tetrazol-5-yl)-thiomethyl]-ceph-3-em-4-carboxylate This compound was prepared analogous to Example 44, starting from 1.0 gm (2.47 mmols) of 7-[D-α-amino(p-hydroxy-phenylacetamido)]-3-[(1-methyl-tetrazol-5-yl)-thiomethyl]-ceph-3-em-4-carboxylic acid and the reaction product of 690 mgm of 5-amino-4-hydroxy-2-p-methylsulfonylanilino-pyrimidine with trimethylsilyl diethylamine and phosgene. Yield of the sodium salt: 940 mgm (52%).

IR-spectrum: 1765, 1650, 1600, 1150 cm$^{-1}$, NMR-spectrum (DMSO+CD$_3$OD) signals at ppm: 3.1 (s, 3H), 3.45 (q, 2H), 3.95 (s, 3H), 4.25 (m, 2H), 4.95 (d, 1H), 5.5 (s, 1H), 5.60 (d, 1H), 6.80 (d, 2H), 7.35 (d, 2H), 7.85 (dd, 4H), 8.30 (s, 1H), The compounds of the present invention, that is, those embraced by formulas I and I' and their nontoxic, pharmacologically acceptable salts, have useful pharmacodynamic properties. More particularly, they exhibit very effective antibacterial activity in warm-blooded animals, such as mice.

Cephalosporin antibiotics are widely used for the treatment of diseases which are caused by pathogenic bacteria in humans and in animals. Particularly, they can be used for the treatment of diseases caused by bacteria which are resistant against other antibiotics such as penicillin compounds, as well as for the treatment of penicillin-sensitive patients. In numerous cases it is desired to use a cephalosporin antibiotic which has a good activity against gram-positive and against gram-negative microorganisms. For that reason wide-ranging research has been performed with a view toward development of various types of cephalosporin antibiotics with a wide activity spectrum.

In these tests it has been found that it is difficult to find cephalosporin antibiotics which, besides a broad activity spectrum, also possess a good activity against various strains of *pseudomonas aeruginosa*. Analogous to investigations in the field of penicillins, it has been tried to obtain pseudomonas-active cephalosporins by acylation of α-aminobenzyl cephalosporins, but it has been found that such compounds are usually not sufficiently active. Therefore, there is a further need to search for new cephalosporins which possess an increased activity against various strains of *pseudomonas aeruginosa* besides a broad activity spectrum.

As already mentioned, while intensive research work has been done with regard to acyl derivatives of α-aminobenzyl derivatives, only little has become known about derivatives where a heterocyclic system is bonded to the α-benzyl hydrogen atom of α-aminobenzyl cephalosporins via a ureido bridge (—NH-CONH—). Only in German Offenlegungsschriften Nos. 2,710,979 and 2,650,826 cephalosporins are described, where pyridines or condensed pyridines are bonded to the cephalosporin nucleus in the way mentioned above.

These compounds, however, exhibit an insufficient activity against pseudomonas.

We have discovered that the compounds according to the present invention, with regard to their antibiotic activity, exhibit a broad activity spectrum together with an unusually good activity against pseudomonas strains. The high activity extends to numerous β-lactamase-forming gram-negative strains, as these compounds possess a high stability against β-lactamases which are formed from a series of gram-negative organisms.

Furthermore, the compounds according to the present invention are very well compatible. Therefore, they are useful for the prophylaxis and chemotherapy of local and systemic infections in both human and veterinary medicine.

Thus, for example, these compounds are useful for the treatment of diseases of the respiratory tract, the pharingeal cavity and urinary tract, particularly pharyngitis, pneumonia, peritonitis, pyelonephritis, otitis, cystitis, endocarditis, bronchitis, arthritis and general systemic infections. Moreover, these compounds are useful as preservatives for inorganic or organic materials, especially for organic materials such as polymers, lubricants, dyes, fibers, leather, paper and wood, as well as foodstuffs.

Many local and/or systemic bacterial diseases can be treated and/or prevented by use of these cephalosporin derivatives of the present invention. Examples of such diseases include but are not limited to those caused by the following microorganisms:

Micrococcaceae, such as *staphylococci*;
Lactobacteriaceae, such as *streptococci*;
Neisseriaceae, such as *neisseria*;
Corynebacteriaceae, such as *corynebacteria*;
Enterobacteriaceae, such as escherichiae bacteria of the coli group;
Klebsiella bacteria, such as *pneumoniae*;
Proteae bacteria of the proteus group, such as *proteus vulgaris*;
Salmonella bacteria, such as thyphimurium;
Shigella bacteria, such as *shigella dysenteriae*;
Pseudomonas bacteria, such as *pseudomonas aeruginosa*;
Aeromonas bacteria, such as *aeromonas lique faciens*;
Spirillaceae such as vibrio bacteria, such as *vibrio cholerae*;
Parvobacteriaeae or brucellaceae, such as pasteurella bacteria;
Brucella bacteria, such as *brucella abortus*;
Haemophilus bacteria, such as *haemophilus influenzae*;
Bordetella bacteria, such as *bordetella pertussis*;
Moraxella bacteria, such as *moraxella lacunata*;
Bacteroidaceae, such as bacteroides bacteria;
Fusiforme bacteria, such as *fusobacterium fusiforme*;
Sphaerophorus bacteria, such as *sphaerophorus necrophorus*;

Bacillaceae, such as aerobe spore formers, like *bacillus antracis;*
Anaerobe spore formers chlostridia, such as *chlostridium perfringens;*
Spirochaetaceae, such as *borrelia bacteria;*
Treponema bacteria, such as *treponema pallidum;* and
Leptospira bacteria, such as *leptospira interrogans.*

Specific examples of compounds of the present invention, which exhibit broad spectrum antibacterial activity against gram-positive and gram-negative bacteria as well as against pseudomonas are those of the formula

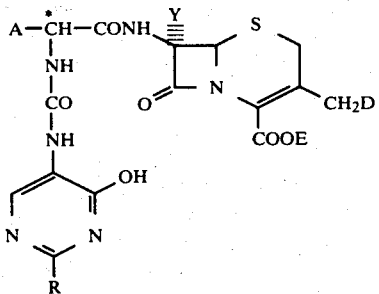

shown in the following table:

TABLE IX

| Compound No. | A | R | Y | D | E |
|---|---|---|---|---|---|
| 1 | Phenyl | H | H | H | H |
| 2 | Phenyl | CH₃ | H | H | H |
| 3 | Phenyl | cyclopropyl | H | H | H |
| 4 | p-HO—phenyl | cyclopropyl | H | H | H |
| 5 | p-HO—phenyl | cyclopropyl | H | OCOCH₃ | H |
| 6 | p-HO—phenyl | cyclopropyl | H | -S-(1-methyltetrazol-5-yl) | H |
| 7 | p-HO—phenyl | cyclopropyl | H | -S-(1-methyltetrazol-5-yl) | —CH₂OCOC(CH₃)₃ |
| 8 | p-HO—phenyl | cyclopropyl | H | -S-(5-methyl-1,3,4-thiadiazol-2-yl) | H |
| 9 | p-HO—phenyl | cyclopropyl | CH₃O | -S-(1-methyltetrazol-5-yl) | H |
| 10 | 2-thienyl | cyclopropyl | H | -S-(1-methyltetrazol-5-yl) | H |
| 11 | 2-furyl | cyclopropyl | H | -S-(1-methyltetrazol-5-yl) | H |
| 12 | p-HO—phenyl | HO | H | —OCOCH₃ | H |

TABLE IX-continued

| Compound No. | A | R | Y | D | E |
|---|---|---|---|---|---|
| 13 | p-HO—phenyl | CH$_3$O— | H | 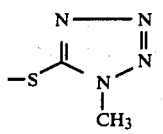 | H |
| 14 | p-HO—phenyl | (CH$_3$)$_2$N | H | 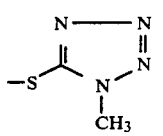 | H |
| 15 | Phenyl | NH$_2$ | H | H | H |
| 16 | p-HO—phenyl | —NHCH$_3$ | H | —OCOCH$_3$ | H |
| 17 | p-HO—phenyl | —NHC$_2$H$_5$ | H |  | H |
| 18 | p-HO—phenyl | —NHC$_3$H$_7$ | H | —OCOCH$_3$ | H |
| 19 | p-HO—phenyl | —NHC$_3$H$_7$ | H | 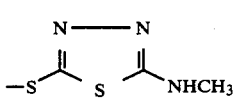 | H |
| 20 | p-HO—phenyl | —NHC$_3$H$_7$ | —OCH$_3$ |  | H |
| 21 | p-HO—phenyl | —NHC$_3$H$_7$ | H | 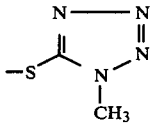 | — |
| 22 | p-HO—phenyl | —NHCH(CH$_3$)$_2$ | H | H | H |
| 23 | p-HO—phenyl | —NHCH(CH$_3$)$_2$ | H | —OCOCH$_3$ | H |
| 24 | p-HO—phenyl | —NHCH(CH$_3$)$_2$ | H | 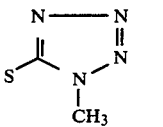 | H |
| 25 | p-HO—phenyl | —NHCH(CH$_3$)$_2$ | H | 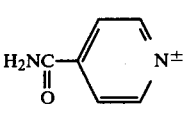 | H |
| 26 | p-HO—phenyl | —NHCH(CH$_3$)$_2$ | H | 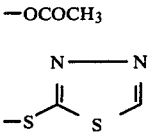 | H |
| 27 | p-HO—phenyl | —NHCH(CH$_3$)$_2$ | H | 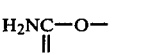 | H |
| 28 | p-HO—phenyl | —NHCH(CH$_3$)$_2$ | H | 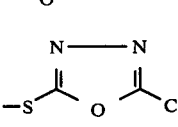 | H |
| 29 | p-HO—phenyl | —NHCH(CH$_3$)$_2$ | H |  | H |

TABLE IX-continued
| Compound No. | A | R | Y | D | E |
|---|---|---|---|---|---|
| 30 | p-HO—phenyl | —NHCH(CH₃)₂ | —OCH₃ | 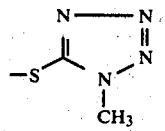 | H |
| 31 | p-HO—phenyl | —NHCH(CH₃)₂ | H | 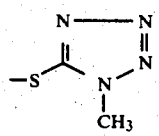 | —CH₂OCOC(CH₃)₃ |
| 32 | p-HO—phenyl | —NHCH(CH₃)₂ | H | 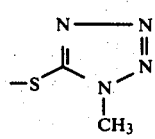 | 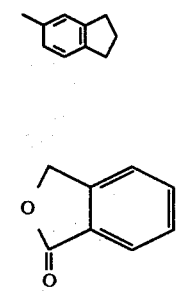 |
| 33 | p-HO—phenyl | —NHCH(CH₃)₂ | | 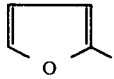 | 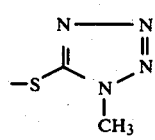 |
| 34 | 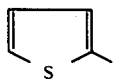 | —NHC₃H₇ | | 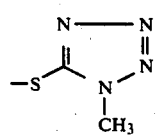 | H |
| 35 | 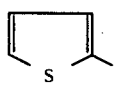 | —NHC₃H₇ | | 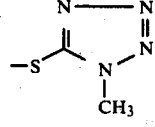 | H |
| 36 | 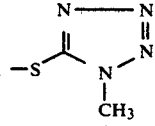 | —NHC₃H₇ | —OCH₃ | 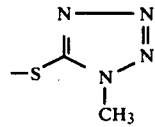 | H |
| 37 | p-HO—phenyl | —NHCH₂CH(CH₃)₂ | H | 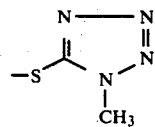 | H |
| 38 | p-HO—phenyl | —NHCH₂CH(CH₃)₂ | H | | H |
| 39 | p-HO—phenyl | —NHCH₂CH(CH₃)₂ | H | | H |
| 40 | p-HO—phenyl | —NHC₄H₉ | H | 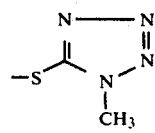 | H |

TABLE IX-continued

| Compound No. | A | R | Y | D | E |
|---|---|---|---|---|---|
| 41 | phenyl | —NHCH$_2$CH=CH$_2$ | H | OCOCH$_3$ | H |
| 42 | p-HO—phenyl | —NHCH$_2$CH=CH$_2$ | H | 1-methyl-tetrazol-5-yl-thio | H |
| 43 | p-HO—phenyl | —NHCH$_2$CH=CH$_2$ | —OCH$_3$ | 1-methyl-tetrazol-5-yl-thio | H |
| 44 | p-HO—phenyl | —NHCH$_2$CH=CH—CH$_3$ | —OCH$_3$ | 1-methyl-tetrazol-5-yl-thio | H |
| 45 | p-HO—phenyl | —NHCH$_2$CH=CH—CH$_3$ | H | 1-methyl-tetrazol-5-yl-thio | —CH$_2$OCOC(CH$_3$)$_3$ |
| 46 | 2-furyl | —NHCH$_2$CH=CH—CH$_3$ | H | 1-methyl-tetrazol-5-yl-thio | H |
| 47 | p-HO—phenyl | —NHCH$_2$CH=CH—CH$_3$ | H | 1,3,4-thiadiazol-2-yl-thio | H |
| 48 | p-HO—phenyl | —NHCH$_2$CH=CH—CH$_3$ | H | OCONH$_2$ | H |
| 49 | p-HO—phenyl | —NHCH$_2$C(CH$_3$)=CH$_2$ | H | 1-methyl-tetrazol-5-yl-thio | H |
| 50 | 3,4-diOH-phenyl | NHCH$_2$CH(CH$_3$)—CH$_2$ | H | 1-methyl-tetrazol-5-yl-thio | H |
| 51 | p-HO—phenyl | —NHC$_6$H$_{11}$ | H | 1-methyl-tetrazol-5-yl-thio | H |
| 52 | p-HO—phenyl | —NHCH$_2$C≡CH | H | 1-methyl-tetrazol-5-yl-thio | H |

TABLE IX-continued

| Compound No. | A | R | Y | D | E |
|---|---|---|---|---|---|
| 53 | HO—⟨phenyl⟩ | —NHCH₃C≡CH | H | tetrazole-S-C(=S)N(CH₃)₂ structure | H |
| 54 | HO—⟨phenyl⟩ | —NH-cyclopropyl | H | 1-methyltetrazole-5-thio | H |
| 55 | HO—⟨phenyl⟩ | —NH-cyclopentyl | H | 1-methyltetrazole-5-thio | H |
| 56 | HO—⟨phenyl⟩ | —NH-cyclopentyl | —OCH₃ | 1-methyltetrazole-5-thio | H |
| 57 | p-HO—phenyl | —NH-cyclopentyl | H | triazoline-thio structure | H |
| 58 | p-HO—phenyl | —NH-cyclopentyl | H | H₂NC(O)-pyridinium (4-carbamoyl-1-methylpyridinium) | — |
| 59 | p-HO—phenyl | —NH-cyclopentyl | H | —S—C(=N—N=C(CH₃))—S— structure | H |
| 60 | ⟨thienyl⟩ | —NH-cyclopentyl | H | 1-methyltetrazole-5-methylthio | H |
| 61 | ⟨thienyl⟩ | —NH-cyclopentyl | H | 1-methyltetrazole-5-thio | H |
| 62 | p-HO—phenyl | —NH-cyclohexyl | H | 1-methyltetrazole-5-thio | H |
| 63 | p-HO—phenyl | —NH-cyclohexyl | H | —OCOCH₃ | H |
| 64 | p-HO—phenyl | —NH-cyclohexyl | H | thiadiazole-thio | H |
| 65 | p-HO—phenyl | —NHCH₂-cyclopropyl | H | 1-methyltetrazole-5-thio | H |

TABLE IX-continued
| Compound No. | A | R | Y | D | E |
|---|---|---|---|---|---|
| 66 | p-HO—phenyl | 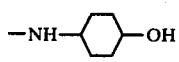 | H | H | H |
| 67 | p-HO—phenyl | 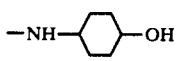 | H | —OCOCH$_3$ | H |
| 68 | p-HO—phenyl | 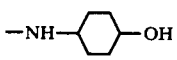 | H | 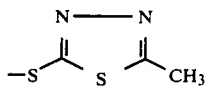 | H |
| 69 | p-HO—phenyl | 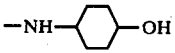 | H | 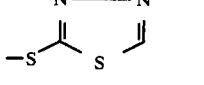 | H |
| 70 | p-HO—phenyl | 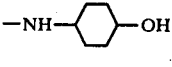 | H | 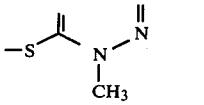 | H |
| 71 | p-HO—phenyl | 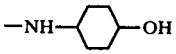 | OCH$_3$ | 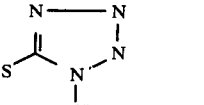 | H |
| 72 | p-HO—phenyl | 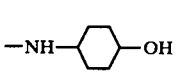 | H | 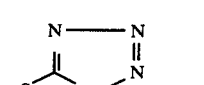 | —CH$_2$OCCH$_3$<br>‖<br>O |
| 73 | p-HO—phenyl | 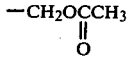 | H |  | 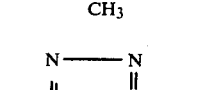 |
| 74 | p-HO—phenyl |  | H | —OCNH$_2$<br>‖<br>O | H |
| 75 | p-HO—phenyl |  | H | 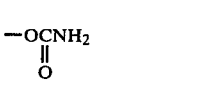 | H |
| 76 |  | 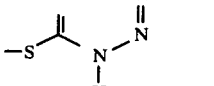 | H | 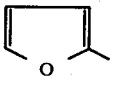 | H |
| 77 |  | 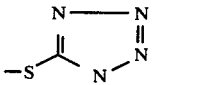 | H | 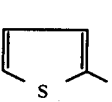 | H |
| 78 | p-HO—phenyl | NHCH$_2$CH$_2$SC$_2$H$_5$ | H |  | H |

TABLE IX-continued

| Compound No. | A | R | Y | D | E |
|---|---|---|---|---|---|
| 79 | p-HO—phenyl | —NHCH$_2$CH$_2$SC$_2$H$_5$ | H | -S-C(=N-N=)-S-C(CH$_3$) (1,3,4-thiadiazole-thio with acetyl) | H |
| 80 | p-HO—phenyl | —NHCH$_2$CH$_2$SC$_2$H$_5$ | H | pyridinium (N$^{\oplus}$—) | — |
| 81 | phenyl | —NHCH$_2$CH$_2$SC$_2$H$_5$ | H | -S-(1-methyltetrazol-5-yl) | H |
| 82 | p-HO—phenyl | —NHCH$_2$CH$_2$OCH$_3$ | H | -S-C(=N-N=CH-)-S- (1,3,4-thiadiazol-2-ylthio) | H |
| 83 | p-HO—phenyl | —NHCH$_2$CH$_2$OCH$_3$ | H | -S-(1-methyltetrazol-5-yl) | H |
| 84 | p-HO—phenyl | NH(CH$_2$)$_3$OH | H | -S-(1-methyltetrazol-5-yl) | H |
| 85 | p-HO—phenyl | NH(CH$_2$)$_3$OH | —OCH$_3$ | -S-(1-methyltetrazol-5-yl) | H |
| 86 | p-HO—phenyl | NH(CH$_2$)$_3$OH | H | -S-C(=N-N=)-O-C(CH$_3$) (1,3,4-oxadiazole) | H |
| 87 | p-HO—phenyl | NH(CH$_2$)$_3$OH | H | -S-C(=N-N=)-S-C(NHCHO) (1,3,4-thiadiazole with NHCHO) | H |
| 88 | p-HO—phenyl | —NH(CH$_2$)$_3$OH | H | -S-(1-methyltetrazol-5-yl) | —CH$_2$OCOC(CH$_3$)$_3$ |
| 89 | p-HO—phenyl | —NH(CH$_2$)$_3$OH | H | -S-(1-methyltetrazol-5-yl) | phthalidyl |
| 90 | furyl | —NH(CH$_2$)$_3$OH | H | -S-(1-methyltetrazol-5-yl) | H |

TABLE IX-continued

| Compound No. | A | R | Y | D | E |
|---|---|---|---|---|---|
| 91 |  | —NH(CH$_2$)$_3$ | H | 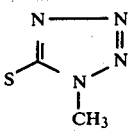 | H |
| 92 |  | —NH(CH$_2$)$_3$OH | H | 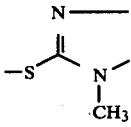 | H |
| 93 | p-HO—phenyl | —NH(CH$_2$)$_3$OH | H | 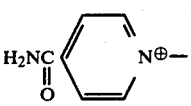 | — |
| 94 | p-HO—phenyl | —NH(CH$_2$)$_3$OH | H | 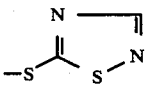 | H |
| 95 | p-HO—phenyl | —NH(CH$_2$)$_3$OH | H | 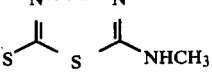 | H |
| 96 | p-HO—phenyl | —NH(CH$_2$)$_3$OH | H | 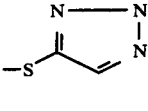 | H |
| 97 | p-HO—phenyl | —NH(CH$_2$)$_3$SH | H | 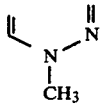 | H |
| 98 | p-HO—phenyl | —NH(CH$_2$)$_3$SO$_2$NH$_2$H | H | 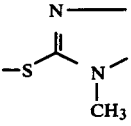 | H |
| 99 | p-HO—phenyl | —NH(CH$_2$)$_3$SO$_2$NH$_2$ | OCH$_3$ | 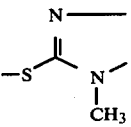 | H |
| 100 | p-HO—phenyl | —NH(CH$_2$)$_3$SO$_2$NH$_2$ | H | OCOCH$_3$ | H |
| 101 | p-HO—phenyl | —NH(CH$_2$)$_3$SO$_2$NH$_2$ | H | 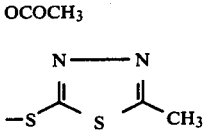 | H |
| 102 |  | —NH(CH$_2$)$_3$SO$_2$NH$_2$ | H | 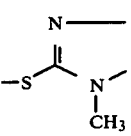 | H |
| 103 |  | —NH(CH$_2$)$_3$SO$_2$NH$_2$ | OCH$_3$ | 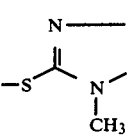 | H |

TABLE IX-continued

| Compound No. | A | R | Y | D | E |
|---|---|---|---|---|---|
| 104 | p-HO—phenyl | —NH(CH$_2$)$_3$CONH$_2$ | H | 1-methyl-tetrazol-5-yl-thio | H |
| 105 | p-HO—phenyl | —NH(CH$_2$)$_3$CONH$_2$ | H | OCOCH$_3$ | H |
| 106 | p-HO—phenyl | —NH(CH$_2$)$_3$CONH$_2$ | —OCH$_3$ | 1-methyl-tetrazol-5-yl-thio | H |
| 107 | p-HO—phenyl | —NH(CH$_2$)$_3$NHCONH$_2$ | H | 1-methyl-tetrazol-5-yl-thio | H |
| 108 | p-HO—phenyl | —NH(CH$_2$)$_2$NHCOCH$_3$ | H | 1-methyl-tetrazol-5-yl-thio | H |
| 109 | p-HO—phenyl | —NH(CH$_2$)$_2$NHCOCH$_3$ | H | OCOCH$_3$ | H |
| 110 | p-HO—phenyl | —NH(CH$_2$)$_3$NHSO$_2$CH$_3$ | H | 1-methyl-tetrazol-5-yl-thio | H |
| 111 | p-HO—phenyl | —NH(CH$_2$)$_3$NHSO$_2$CH$_3$ | H | OCOCH$_3$ | H |
| 112 | p-HO—phenyl | —NH(CH$_2$)$_3$OCOCH$_3$ | H | 1-methyl-tetrazol-5-yl-thio | H |
| 113 | p-HO—phenyl | —NH(CH$_2$)$_3$SOCH | H | 1-methyl-tetrazol-5-yl-thio | H |
| 114 | p-HO—phenyl | —NHCH$_2$—C$_6$H$_4$—OH | H | H | H |
| 115 | p-HO—phenyl | —NHCH$_2$—C$_6$H$_4$—OH | H | OCOCH$_3$ | H |
| 116 | p-HO—phenyl | —NHCH$_2$—C$_6$H$_4$—OH | —OCH$_3$ | 1-methyl-tetrazol-5-yl-thio | H |
| 117 | p-HO—phenyl | —NHCH$_2$—C$_6$H$_4$—OH | H | 1-methyl-tetrazol-5-yl-thio | H |

TABLE IX-continued

| Compound No. | A | R | Y | D | E |
|---|---|---|---|---|---|
| 118 | p-HO—phenyl | —NHCH₂—C₆H₄—OH | H | 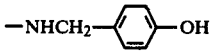 | H |
| 119 | 3,4-(HO)₂-phenyl | —NHCH₂—(3,4-methylenedioxyphenyl) | H | 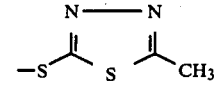 | H |
| 120 | p-HO—phenyl | —NHCH₂—(3,4-methylenedioxyphenyl) | H | 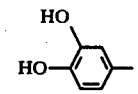 | H |
| 121 | p-HO—phenyl | —NHCH₂—(3,4-methylenedioxyphenyl) | H | —OCOCH₃ | H |
| 122 | p-HO—phenyl | —NHCH₂—(3,4-methylenedioxyphenyl) | H | 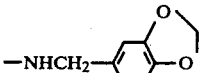 | H |
| 123 | p-HO—phenyl | —NHCH₂—C₆H₄—SO₂NH₂ | H | 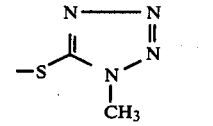 | H |
| 124 | p-HO—phenyl | —NHCH₂—C₆H₄—SO₂NH₂ | H | OCOCH₃ | H |
| 125 | p-HO—phenyl | —NHCH₂—C₆H₅ | H | OCOCH₃ | H |
| 126 | p-HO—phenyl | —NHCH₂—C₆H₄—SOCH₃ | H | 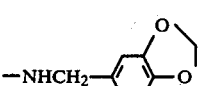 | H |
| 127 | p-HO—phenyl | —NH—C₆H₄—Cl | H | H | H |
| 128 | p-HO—phenyl | —NH—C₆H₄—Cl | H | —OCOCH₃ | H |
| 129 | p-HO—phenyl | —NH—C₆H₄—Cl | H | 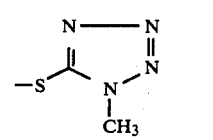 | H |
| 130 | p-HO—phenyl | —NH—C₆H₄—Cl | H | 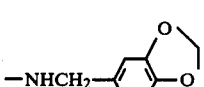 | —CH₂OCOC(CH₃)₃ |
| 131 | p-HO—phenyl | —NH—C₆H₄—Cl | H | 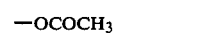 | H |

TABLE IX-continued

| Compound No. | A | R | Y | D | E |
|---|---|---|---|---|---|
| 132 | 2-methylfuran | —NH—C₆H₄—Cl (p) | H | -S-(1-methyl-tetrazol-5-yl) | H |
| 133 | p-HO—phenyl | —NH—C₆H₃—Cl₂ (3,4) | H | -S-(1-methyl-tetrazol-5-yl) | H |
| 134 | p-HO—phenyl | —NH—C₆H₄—Cl (p) | H | -S-(5-acetamido-1,3,4-thiadiazol-2-yl) | H |
| 135 | p-HO—phenyl | —NH—C₆H₄—OH (p) | H | -S-(5-methyl-1,3,4-thiadiazol-2-yl) | H |
| 136 | p-HO—phenyl | —NH—C₆H₄—OH (p) | H | -S-(1-methyl-tetrazol-5-yl) | H |
| 137 | p-HO—phenyl | —NH—C₆H₄—OH (p) | —OCH₃ | -S-(1-methyl-tetrazol-5-yl) | H |
| 138 | p-HO—phenyl | —NH—C₆H₄—OH (p) | H | -S-(1-methyl-tetrazol-5-yl) | —CH₂OCO(CH₃)₃ |
| 139 | 2-methylthiophene | —NH—C₆H₄—OH (p) | H | -S-(1-methyl-tetrazol-5-yl) | H |
| 140 | 2-methylfuran | —NH—C₆H₄—OH (p) | H | -S-(1-methyl-tetrazol-5-yl) | H |
| 141 | p-HO—phenyl | —NH—C₆H₄—OH (p) | H | —OCONH₂ | H |
| 142 | p-HO—phenyl | —NH—C₆H₄—OH (p) | H | 4-carbamoylpyridinium | — |
| 143 | p-HO—phenyl | —NH—C₆H₄—N(CH₃)₂ (p) | H | -S-(1-methyl-tetrazol-5-yl) | H |

TABLE IX-continued

| Compound No. | A | R | Y | D | E |
|---|---|---|---|---|---|
| 144 | p-HO—phenyl | —NH—C₆H₄—N(CH₃)₂ | H | 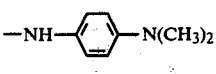 | H |
| 145 | p-HO—phenyl | —NH—C₆H₄—N(CH₃)₂ | H | —OCOCH₃ | H |
| 146 | p-HO—phenyl | —NH—C₆H₄—N(CH₃)₂ | H | 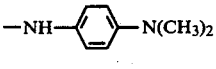 | H |
| 147 | p-HO—phenyl | —NH—C₆H₄—N(CH₃)₂ | H |  | H |
| 148 | p-HO—phenyl | —NH—C₆H₄—SO₂NH₂ | H | H | H |
| 149 | p-HO—phenyl | —NH—C₆H₄—SO₂NH₂ | H | —OCOCH₃ | H |
| 150 | p-HO—phenyl | —NH—C₆H₄—SO₂NH₂ | H |  | H |
| 151 | p-HO—phenyl | —NH—C₆H₄—SO₂NH₂ | H | 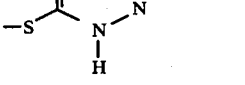 | H |
| 152 | p-HO—phenyl | —NH—C₆H₄—SO₂NH₂ | H | 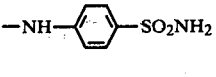 | H |
| 153 | p-HO—phenyl | —NH—C₆H₄—SO₂NH₂ | H | —OCONH₂ | H |
| 154 | p-HO—phenyl | —NH—C₆H₄—SO₂NH₂ | H |  | H |
| 155 | p-HO—phenyl | —NH—C₆H₄—SO₂NH₂ | H |  | H |
| 156 | p-HO—phenyl | —NH—C₆H₄—SO₂NH₂ | H | 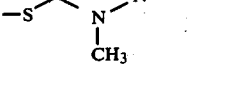 | H |
| 157 | p-HO—phenyl | —NH—C₆H₄—SO₂NH₂ | H | 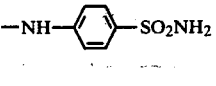 | H |
| 158 | p-HO—phenyl | —NH—C₆H₄—SO₂NH₂ | H | 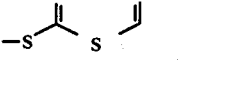 | H |

TABLE IX-continued

| Compound No. | A | R | Y | D | E |
|---|---|---|---|---|---|
| 159 | p-HO—phenyl | —NH—C₆H₄—SO₂NH₂ | H | 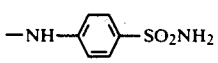 | H |
| 160 | p-HO—phenyl | —NH—C₆H₄—SO₂NH₂ | H | 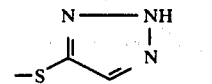 | H |
| 161 | p-HO—phenyl | —NH—C₆H₄—SO₂NH₂ | H | 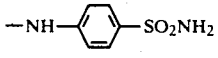 | — |
| 162 | p-HO—phenyl | —NH—C₆H₄—SO₂NH₂ | H | 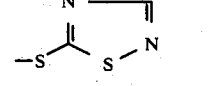 | |
| 163 | p-HO—phenyl | —NH—C₆H₄—SO₂NH₂ | H | 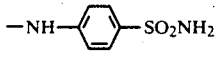 | H |
| 164 | p-HO—phenyl | —NH—C₆H₄—SO₂NH₂ | H | 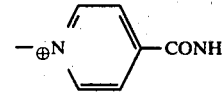 | H |
| 165 | 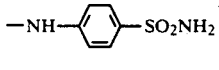 | —NH—C₆H₄—SO₂NH₂ | H | —OCOCH₃ | H |
| 166 | 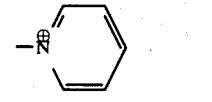 | —NH—C₆H₄—SO₂NH₂ | H | 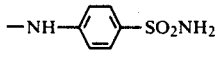 | H |
| 167 | 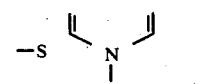 | —NH—C₆H₄—SO₂NH₂ | —OCH₃ | 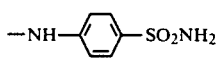 | H |
| 168 | 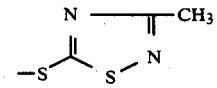 | —NH—C₆H₄—SO₂NH₂ | H | —OCONH₂ | H |
| 169 |  | —NH—C₆H₄—SO₂NH₂ | —OCH₃ | —OCONH₂ | H |
| 170 | 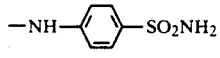 | —NH—C₆H₄—SO₂NH₂ | H | 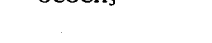 | H |
| 171 | p-HO—phenyl | —NH—C₆H₄—SO₂NH₂ | —OCH₃ | —OCOCH₃ | H |
| 172 | p-HO—phenyl | —NH—C₆H₄—SO₂NH₂ | —OCH₃ | —OCONH₂ | H |

TABLE IX-continued
| Compound No. | A | R | Y | D | E |
|---|---|---|---|---|---|
| 173 | p-HO—phenyl | —NH—C₆H₄—SO₂NH₂ | —OCH₃ | 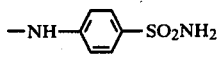 | H |
| 174 | p-HO—phenyl | —NH—C₆H₄—SO₂NH₂ | H |  | CH₂COOC(CH₃)₃ |
| 175 | p-HO—phenyl | —NH—C₆H₄—SO₂NH₂ | H | 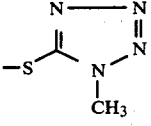 | 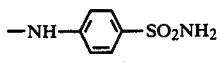 |
| 176 | 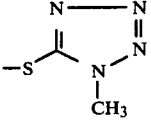 | —NH—C₆H₄—SO₂NH₂ | H |  | H |
| 177 | 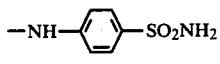 | —NH—C₆H₄—SO₂NH₂ | H | 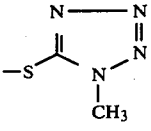 | H |
| 178 | 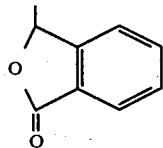 | —NH—C₆H₄—SO₂NH₂ | H | —OCOCH₃ | H |
| 179 |  | —NH—C₆H₄—SO₂NH₂ | H | 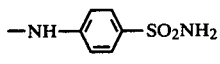 | H |
| 180 | 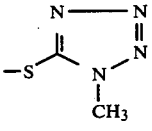 | —NH—C₆H₄—SO₂NH₂ | H | 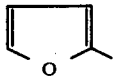 | H |
| 181 | 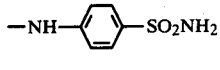 | —NH—C₆H₄—SO₂NH₂ | H | 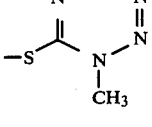 | H |
| 182 | p-HO—phenyl | —NH—C₆H₄—SO₂NHCH₃ | H | 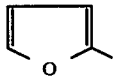 | H |
| 183 | p-HO—phenyl | —NH—C₆H₄—SO₂NHCH₃ | H | —OCOCH₃ | H |

TABLE IX-continued

| Compound No. | A | R | Y | D | E |
|---|---|---|---|---|---|
| 184 | p-HO—phenyl | —NH—C6H4—SO2NHCH3 | —OCH3 | -S-tetrazole-N-CH3 | H |
| 185 | 2-thienyl | —NH—C6H4—SO2NHCH3 | H | -S-tetrazole-N-CH3 | H |
| 186 | p-HO—phenyl | —NH—C6H4—SO2NHC2H5 | H | -S-tetrazole-N-CH3 | H |
| 187 | p-HO—phenyl | —NH—C6H4—SO2N(CH3)2 | H | -S-tetrazole-N-CH3 | H |
| 188 | p-HO—phenyl | —NH—C6H4—SO2NH2 (meta) | H | -S-tetrazole-N-CH3 | H |
| 189 | p-HO—phenyl | —NH—C6H5 | H | —OCOCH3 | H |
| 190 | p-HO—phenyl | —NH—C6H5 | H | -S-tetrazole-N-CH3 | H |
| 191 | p-HO—phenyl | —NH—C6H4—NO2 | H | -S-tetrazole-N-CH3 | H |
| 192 | p-HO—phenyl | —NH—C6H4—COCH3 | H | -S-tetrazole-N-CH3 | H |
| 193 | p-HO—phenyl | —NH—C6H4—NHCOCH3 | H | —OCOCH3 | H |
| 194 | p-HO—phenyl | —NH—C6H4—NHCOCH3 | H | -S-tetrazole-N-CH3 | H |
| 195 | p-HO—phenyl | —NH—C6H4—SOCH3 | H | -S-tetrazole-N-CH3 | H |

TABLE IX-continued

| Compound No. | A | R | Y | D | E |
|---|---|---|---|---|---|
| 196 | p-HO—phenyl | —NH—C₆H₄—SOCH₃ | H | —OCOCH₃ | H |
| 197 | p-HO—phenyl | —NH—C₆H₄—SOCH₃ | H | pyridinium-4-CONH₂ (±N) | — |
| 198 | thienyl (S) | —NH—C₆H₄—SOCH₃ | H | —S-(1-methyltetrazol-5-yl) | H |
| 199 | thienyl (S) | —NH—C₆H₄—SOCH₃ | —OCH₃ | —S-(1-methyltetrazol-5-yl) | H |
| 200 | p-HO—phenyl | —NH—C₆H₄—CONH₂ | H | —S-(1-methyltetrazol-5-yl) | H |
| 201 | p-HO—phenyl | —NH—C₆H₄—CONH₂ | —OCH₃ | —S-(1-methyltetrazol-5-yl) | H |
| 202 | p-HO—phenyl | —NH—C₆H₄—CONH₂ | H | —OCOCH₃ | H |
| 203 | p-HO—phenyl | —NH—C₆H₄—CONH₂ | H | —S-(5-methyl-1,3,4-thiadiazol-2-yl) | H |
| 204 | thienyl (S) | —NH—C₆H₄—CONH₂ | H | —S-(1-methyltetrazol-5-yl) | H |
| 205 | p-HO—phenyl | —NH—C₆H₄—NHCONH₂ | H | —S-(1-methyltetrazol-5-yl) | H |
| 206 | p-HO—phenyl | —NH—C₆H₄—NHCONH₂ | H | —OCOCH₃ | H |
| 207 | p-HO—phenyl | —NH—C₆H₃(CONH₂)(OH) | H | —S-(1-methyltetrazol-5-yl) | H |
| 208 | p-HO—phenyl | —NH—C₆H₃(CONH₂)(OH) | H | —OCOCH₃ | H |

TABLE IX-continued

| Compound No. | A | R | Y | D | E |
|---|---|---|---|---|---|
| 209 | p-HO—phenyl | —NH—⟨phenyl(OH)(CONH$_2$)⟩ | H | —OCOCH$_3$ | H |
| 210 | p-HO—phenyl | —NH—⟨phenyl(OH)(CONH$_2$)⟩ | H | —S—(1-methyl-tetrazol-5-yl) | H |
| 211 | p-HO—phenyl | —NH—⟨phenyl(OH)(SO$_2$NH$_2$)⟩ | H | —S—(1-methyl-tetrazol-5-yl) | H |
| 212 | p-HO—phenyl | —NH—⟨phenyl(OH)(SO$_2$NH$_2$)⟩ | H | —OCOCH$_3$ | H |
| 213 | p-HO—phenyl | —NHCOCH$_3$ | H | —OCOCH$_3$ | H |
| 214 | p-HO—phenyl | —NHCOCH$_3$ | H | —S—(1-methyl-tetrazol-5-yl) | H |
| 215 | p-HO—phenyl | —NHCOCH$_3$ | H | —S—(5-methyl-1,3,4-thiadiazol-2-yl) | H |
| 216 | p-HO—phenyl | —NH—⟨phenyl-SO$_2$CH$_3$⟩ | H | —S—(1-methyl-tetrazol-5-yl) | H |

The antibiotic activities of the compounds of the present invention were ascertained by the following test methods:

1. In vitro tests:

The tests were performed using the serial dilution test in the microtiter system. The effect of the test compounds on bacteriostasis was examined at the following concentrations: 80, 40, 20, 10, 5, 2.5, 1.25, 0.6, 0.3, 0.08 and 0.02 μgm/ml. The nutrient medium consisted of 10 gm of peptone, 8 gm of meat extract oxoid, 3 gm of sodium chloride, and 2 gm of sec. sodium phosphate diluted with distilled water to 100 ml (pH 7.2–7.4). Only in the test against streptococci 1% of glucose was added. The age of the primary cultures was approximately 20 hours. The standardization of the bacteria suspension was effected using a photometer according to the method of Eppendorf (test tube φ14 mm, filter 546 nm), using for comparison a barium sulfate suspension formed by the addition of 3.0 ml of 1% barium chloride solution to 97 ml of 1% sulfuric acid. After the standardization, *Streptococcus aronson* was further diluted to a concentration of 1:15, and the other bacteria to a concentration of 1:1500, using a sodium chloride solution.

16 mgm of the particular test compound were put into a 10 ml measuring flask, and the flask was subsequently filled to the mark with solvent. The further dilution series was standardized with distilled water or the appropriate solvent.

The cavities of the microtiter plates were filled with 0.2 ml of nutrient medium. 0.01 ml of the appropriate test compound solution was then added, followed by inoculation with 0.01 ml of the standardized bacteria suspension. The bacteria were incubated at 37° C. for 18 to 20 hours. Control tests using only the solvent were carried out simultaneously.

The measurement was carried out macroscopically to determine the minimum inhibitory concentration (the lowest still bacteriostatically effective concentration).

The following test organisms were used:

Staphylococcus aureus SG 511, St. aureus E 88 (β-lactamase carrier), Escherichia coli ATCC 11 775, *Pseudomonas aeruginosa Hamburgensis* and *Pseudomonas aeruginosa Walter*, *Serratia marcescens* ATCC 13 880, *Klebsiella pneumoniae* ATCC 10 031 and 272, *Proteus mirabilis Hamburgensis*, *Proteus rettgeri Eb. cloaceae* ATCC 13047, and E. coli R+TEM (β-lactamase carrier).

The following tables show the determined minimum inhibitory concentrations (MIC) for a few representative compounds (E=Na) of the present invention, and two known cephalosporins for comparison:

TABLE X

| A | R | Y | D | Compound |
|---|---|---|---|---|
| p-HO—phenyl | cyclopropyl | H |  | A |
| p-HO—phenyl | NHC₃H₇ | H | 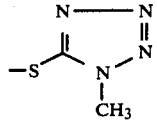 | B |
| p-HO—phenyl | NH—cyclohexyl—OH | H | 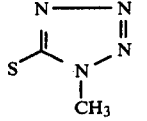 | C |
| p-HO—phenyl | NH—cyclohexyl—OH | H | 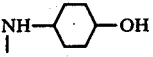 | D |
| p-HO—phenyl | NH(CH₂)₃OH | H | 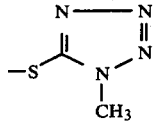 | E |
| thienyl (D,L) | NH—cyclohexyl—OH | H | 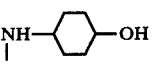 | F |
| p-HO—phenyl | NH—cyclohexyl—OH | H | 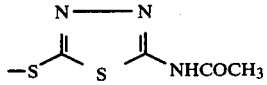 | G |
| p-HO—phenyl | NH—C₆H₄—SO₂NHCH₃ | H | —OCOCH₃ | H |
| p-HO—phenyl | NH—C₆H₄—SO₂NHCH₃ | H | 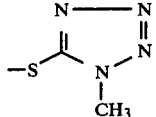 | J |
| p-HO—phenyl | NH—C₆H₄—SO₂NHCH₃ | H | 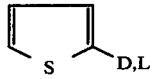 | K |
| p-HO—phenyl | NH—C₆H₄—SO₂NH₂ | H | 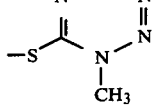 | L |
| thienyl (D,L) | NH—C₆H₄—SO₂NH₂ | H | 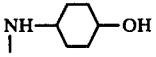 | M |

TABLE X-continued

| A | R | Y | D | Compound |
|---|---|---|---|---|
| p-HO—phenyl | NH—⟨phenyl⟩—SO$_2$NHCH$_3$ | H | N——N, —S⟨⟩S⟨⟩CH$_3$ | N |

TABLE XI

MIC values of various cephalosporins (in μg/ml)

| Compound | S. aureus SG 511 | S. aureus E 88 | E. coli ATCC 11775 | Pseud. aerug. Hbg. | Pseud. aerug. Walter | Klebs. pneum. ATCC 10031 | Klebs. pneum. 272 | Prot. mir. Hbg. | Prot. rettg. | Eb. cloaceae | E. coli R + TFM | Serr. marcesc. ATCC 1388 |
|---|---|---|---|---|---|---|---|---|---|---|---|---|
| Cefuroxim | 1 | 16 | 8 | >100 | >100 | 2 | 4 | 0.5 | 2 | 32 | 4 | 8 |
| Cephazolin | 0.06 | 8 | 4 | >100 | >100 | 1 | 2 | 4 | >100 | >100 | 4 | >100 |
| A | 0.5 | 8 | 0.5 | 8 | 8 | 1 | 1 | 0.5 | 2 | 2 | 8 | 2 |
| B | 1 | 8 | 0.5 | 4 | 8 | 0.5 | 0.5 | 0.25 | 1 | 1 | 8 | 1 |
| C | 1 | 8 | 0.13 | 4 | 4 | 0.5 | 0.5 | 0.13 | 1 | 0.5 | 8 | 0.5 |
| D | 1 | 8 | 1 | 8 | 8 | 2 | 2 | 1 | 8 | 8 | 16 | 4 |
| E | 1 | 8 | 0.25 | 4 | 8 | 0.5 | 1 | 0.13 | 1 | 0.5 | 16 | 1 |
| F | 1 | 8 | 0.5 | 16 | 16 | 2 | 2 | 0.5 | 2 | 4 | 16 | 2 |
| G | 1 | 16 | 0.5 | 16 | 16 | 2 | 2 | 0.5 | 1 | 2 | 16 | 2 |
| H | 1 | 16 | 0.13 | 4 | 4 | 0.5 | 0.5 | 0.6 | 0.5 | 2 | 16 | 0.5 |
| J | 1 | 16 | 0.5 | 8 | 8 | 0.5 | 0.25 | 0.25 | 1 | 1 | 8 | 0.5 |
| K | 0.5 | 4 | <0.03 | 4 | 2 | 0.06 | 0.13 | 0.06 | 0.25 | 0.5 | 2 | 0.13 |
| L | 0.5 | 4 | <0.03 | 2 | 2 | 0.06 | 0.06 | <0.06 | 0.13 | 0.5 | 2 | 0.06 |
| M | 0.5 | 4 | 0.13 | 4 | 4 | 0.25 | 0.25 | 0.13 | 0.5 | 0.5 | 4 | 0.25 |
| N | 1 | 8 | 0.25 | 4 | 4 | 0.25 | 0.5 | 0.5 | 0.5 | 1 | 4 | 0.25 |

The acute toxicity was determined by peroral and subcutaneous administration of the compounds of table X to white mice at increasing dosage levels.

The $LD_{50}$ is the dose which leads to the death of 50% of the animals within 8 days. All of the compounds showed after oral administration an $LD_{50}$ of >4 gm/kg; and after subcutaneous administration an $LD_{50}$ of >3 gm/kg, i.e. at 3 gm/kg no animals died. This means that the compounds are substantially non-toxic at dosage levels for practical use.

A series of the compounds according to the invention was tested in vivo in mice against experimental infections. As pathogenic bacteria were used E. coli ATCC 11775 and Pseudomonas aeruginosa Walter. An intraperitoneal infection was induced in each mouse with 0.2 ml of a 5% mucin suspension of the bacteria corresponding to approximately $1.4 \times 10^6$ E. coli cells and $1.3 \times 10^6$ Pseudomonas cells per mouse. Female NMRI mice were used, divided into groups of 10 animals. Two groups were untreated and the remaining groups were treated with different doses of the cephalosporins to be tested to determine the $ED_{50}$ (dose at which 50% of the animals survived). The groups infected with E.coli were on the first day treated with the test compound three times (1.4 and 7 hours post infectionem) and on the second day twice. The groups with the Pseudomonas infection were on the first day treated with the test compound six times (1, 3, 5, 7, 9 and 11 hours post infectionem), and on the following two days twice.

The observation time was in both cases 7 days. The results of these tests with representatives of the cephalosporins according to the invention are shown in the following Table XII:

TABLE XII

In vivo activity in mice:

| Compound | $ED_{50}$ (mg*/kg) |
|---|---|
| (a) E. coli - infection (subcutaneous administration): | |
| A | 1.6 |
| B | 1.1 |

TABLE XII-continued

In vivo activity in mice:

| Compound | $ED_{50}$ (mg*/kg) |
|---|---|
| C | 0.4 |
| E | 0.8 |
| K | 0.3 |
| L | 0.15 |
| Cefuroxim | 37 |
| (b) Pseudomonas (subcutaneous administration): | |
| A | 15.2 |
| B | 12.4 |
| C | 4.2 |
| E | 11.2 |
| K | 3.6 |
| L | 2.1 |
| Cefuroxim | at 200 mg/kg all animals died |

*per dose

These values also show a significant superiority of compounds of the present invention over the comparison substance.

For pharmaceutical purposes the compounds of the present invention are administered to warm-blooded animals perorally, parenterally, topically or rectally as active ingredients in customary pharmaceutical compositions, that is, compositions consisting essentially of an inert pharmaceutical carrier and an effective amount of the active ingredient, such as tablets, coated tablets, capsules, granulates, suppositories, solutions, suspensions, emulsions, ointments, gels, creams, powders and sprays. The active ingredient or a mixture of the different active ingredients of the formula I may be administered to both humans and animals. The daily dose is from 5 to 500 mgm/kg, preferably from 10 to 200 mg/kg, body weight at intervals of 24 hours, optionally administered in the form of several single doses. A single dose will preferably contain the active ingredient according to the invention in amounts of from 1 to 250, especially 10 to 60 mg/kg body weight. Depending on the type and body weight of the patient to be treated, on the type and severity of the disease, on the type of preparation and on the route of administration as well as on the period or interval over which the administration takes place, it may, however, be necessary to deviate from the above dosages. Thus, it may be sufficient in some cases to administer less than the abovementioned amount of active ingredient, while in other cases the abovementioned amount of active ingredient must be exceeded. The optimum dosage and route of administration of the active ingredients which are necessary in each case can easily be determined by one skilled in the art.

If the new compounds are used as additives for animal feed, they can be administered in the usual concentrations and preparations together with the feed or with feed preparations or with drinking water. By means of such administration the infection by gram-negative or gram-positive bacteria can be prevented, improved and/or cured, and also a promotion of the growth and an improvement in the utilization of the feed can be achieved.

The following examples illustrate a few pharmaceutical dosage unit compositions comprising a compound of the present invention as an active ingredient and represent the best modes contemplated of carrying out the invention. The parts are parts by weight unless otherwise specified.

EXAMPLE 143

Tablets

The tablet composition is compounded from the following ingredients:

| | |
|---|---|
| Pivaloyloxymethyl 7-{D-α-[(2-p-amino-sulfonylanilino-4-hydroxy-5-pyrimidinyl)-ureido]-p-hydroxy-phenylacetamido}-3-[(1-methyl-tetrazol-5-yl)-thiomethyl]-ceph-3-em-4-carboxylate | 2.0 parts |
| Lactose | 5.0 parts |
| Potato starch | 1.8 parts |
| Magnesium stearate | 0.1 parts |
| Talcum | 0.1 parts |
| Total | 9.0 parts |

Preparation

The ingredients are admixed in conventional manner, and the composition is compressed into 900 mgm-tablets in a tablet making maching. Each tablet is an oral dosage unit composition containing 200 mgm of the active ingredient.

EXAMPLE 144

Coated tablets

The tablet composition is compounded from the following ingredients:

| | |
|---|---|
| Pivaloyloxymethyl 7-{D-α-[(2-p-amino-sulfonylanilino-4-hydroxy-5-pyrimidinyl)-ureido]-p-hydroxy-phenylacetamido}-3-[(1-methyl-tetrazol-5-yl)-thiomethyl]-ceph-3-em-4-carboxylate | 2.0 parts |
| Lactose | 5.0 parts |
| Potato starch | 1.8 parts |
| Magnesium stearate | 0.1 parts |
| Talcum | 0.1 parts |
| Total | 9.0 parts |

Preparation

The ingredients are admixed in conventional manner, and the composition is compressed into 900 mgm-tablets which are subsequently coated with a thin shell consisting essentially of a mixture of sugar, potato starch, talcum, and tragacanth. Each coated tablet is an oral dosage unit composition containing 200 mgm of the active ingredient.

EXAMPLE 145

Gelatin capsules 500 mgm portions of finely milled pivaloylmethyl 7-{D-α-[2-p-amino-sulfonylanilino-4-hydroxy-5-pyrimidinyl)-ureido]-p-hydroxy-phenylacetamido}-3-[(1-methyl-tetrazol-5-yl)-thiomethyl]-ceph-3-em-4-carboxylate are filled into hard gelatin capsules of suitable size.

EXAMPLE 146

Injectable solution

Under aseptic conditions, 251 gm of sodium 7-{D-α-[(2-p-amino-sulfonylanilino-4-hydroxy-5-pyrimidinyl)-ureido]-p-hydroxy-phenylacetamido}-3-[(1-methyl-tetrazol-5-yl)-thiomethyl]-ceph-3-em-4-carboxylate are dissolved in 2008 ml of distilled water suitable for injection, the solution is filtered through a Millipore filter (pore size: 0.22 μm), 2.0 ml-portions of the filtrate are filled into 10 cc-ampules, the contents are lyophilized, and the ampules are closed with a rubber stopper and sealed with an aluminum cap. Each of these dry ampules contains 250 mgm of the active ingredient (ampule A).

Likewise under aseptic conditions, 2.0 ml-portions of a physiological salt solution are filled into 2 cc-ampules which are then sealed (ampule B).

Prior to injection, the contents of ampule B are added to the contents of ampule A, whereby a solution suitable for intravenous injection is obtained.

EXAMPLE 147

Infusion solution 20 ml of distilled water suitable for injection are added to the contents of two ampules A of the preceding example, and the resulting solution is dissolved in 250 ml of an aqueous 5% solution of glucose suitable for injection, whereby a continuous infusion solution is obtained.

Any one of the other compounds embraced by formula I or a non-toxic, pharmacologically acceptable salt thereof may be substituted for the particular active ingredient in Examples 143 through 147. Likewise, the amount of active ingredient in these illustrative examples may be varied to achieve the dosage unit range set forth above, and the amounts and nature of the inert pharmaceutical carrier ingredient may be varied to meet particular requirements.

While the present invention has been illustrated with the aid of certain specific embodiments thereof, it will be readily apparent to others skilled in the art that the invention is not limited to these particular embodiments, and that various changes and modifications may be made without departing from the spirit of the invention or the scope of the appended claims.

We claim:
1. A compound of the tautomeric formulas

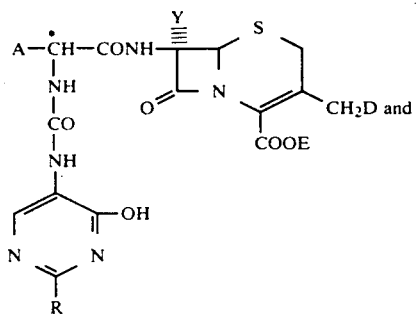

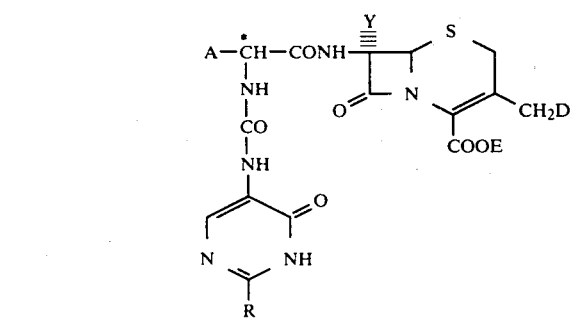

wherein

A is phenyl, 4-hydroxyphenyl, cyclohexyl, cyclohexene-1-yl, cyclohexa-1,4-diene-1-yl, 2-thienyl, 3-thienyl, 2-furyl, 3-furyl or 3,4-disubstituted phenyl, where the substituents are each chlorine, hydroxyl or methoxy;

Y is hydrogen or methoxy;

D is S-Het, where Het is 1-methyl-tetrazol-5-yl, tetrazol-5-yl, 3-methyl-1,2,4-thiadiazol-5-yl, 1,2,4-thiadiazol-5-yl, 1,3,4-thiadiazol-5-yl, 2-methyl-1,3,4-thiadiazol-5-yl, 2-methylamino-1,3,4-thiadiazol-5-yl, 2-dimethylamino-1,3,4-thiadiazol-5-yl, 2-formylamino-1,3,4-thiadiazol-5-yl, 2-acetylamino-1,3,4-thiadiazol-5-yl, 2-methyl-1,3,4-oxadiazol-5-yl, 1,2,3-triazol-4-yl or 1,2,4-triazol-3-yl;

R is hydrogen, methyl, cyclopropyl, hydroxyl, methoxy, ethoxy, mercapto, morpholino, thiomorpholino, thiomorpholino-S-oxide, thiomorpholino-S,S-dioxide,

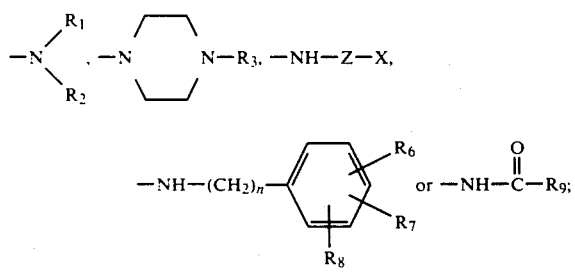

R₁ and R₂ are each hydrogen; straight or branched aliphatic hydrocarbyl of 1 to 6 carbon atoms, optionally containing one to two duble bonds or a triple bond; cycloalkyl of 3 to 6 carbon atoms; or cycloalkyl-alkyl of 3 to 6 carbon atoms in the cycloalkyl moiety and 1 to 2 carbon atoms in the alkyl moiety;

$R_3$ is formyl, acetyl or ethoxycarbonyl;

Z is alkylene of 1 to 4 carbon atoms or cycloalkylene of 3 to 6 carbon atoms;

X is cyano, hydroxyl, mercapto, amino, aminocarbonyl, aminosulfonyl, aminocarbonylamino,

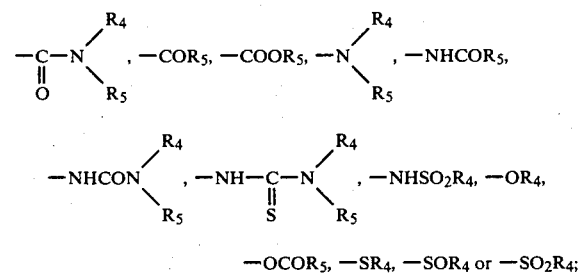

$-OCOR_5$, $-SR_4$, $-SOR_4$ or $-SO_2R_4$;

$R_4$ is alkyl of 1 to 3 carbon atoms;

$R_5$ is hydrogen or alkyl of 1 to 3 carbon atoms;

n is 0 or 1;

$R_6$, $R_7$ and $R_8$ are each hydrogen, halogen, amino, alkylamino, dialkylamino, hydroxy, alkoxy, formylamino, acetylamino, aminocarbonylamino, alkylaminocarbonylamino, dialkylaminocarbonylamino, nitro, alkylsulfonylamino, formyl, alkylcarbonyl, alkylcarbonyloxy, alkoxycarbonyl, alkoyxcarbonyloxy, carboxyl, aminocarbonyl, alkylaminocarbonyl, dialkylaminocarbonyl, aminocarboxyl, alkylaminocarboxyl, dialkylaminocarboxyl, alkoxycarbonylamino, cyano, mercapto, alkylmercapto, alkylsulfinyl, alkylsulfonyl, aminosulfonyl, alkylaminosulfonyl, dialkylaminosulfonyl, hydroxysulfonyl, or alkyl, where each alkyl moiety in these variants may contain 1 to 3 carbon atoms;

$R_9$ is hydrogen, alkyl of 1 to 4 carbon atoms, alkoxy of 1 to 3 carbon atoms, amino, methylamino or dimethylamino; and E is hydrogen or a protective group which is easily removable in vitro or in vivo;

or, when E is hydrogen, a non-toxic, pharmacologically acceptable salt thereof formed with an inorganic or organic base.

2. A compound of claim 1 which has the D═R— configuration.

3. The compound of claim 1 which is sodium 7-{D-α-[2-cyclopropyl-4-hydroxy-5-pyrimidinyl)-ureido]-p-hydroxy-phenylacetamido}-3-[1-methyl-tetrazol-5-yl)-thiomethyl]-ceph-3-em-4-carboxylate.

4. The compound of claim 1 which is sodium 7-{D-α-[(2-cyclopropyl-4-hydroxy-5-pyrimidinyl)-ureido]-p-hydroxy-phenylacetamido}-3-[(2-methyl-thiadiazol-5-yl)-thiomethyl]-ceph-2-em-4-carboxylate.

5. The compound of claim 1 which is sodium 7-{D-α-[(4-hydroxy-2-propylamino-5-pyrimidinyl)-ureido]-p-hydroxyphenylacetamido}-3-[(1-methyl-tetrazol-5-yl)-thiomethyl]-ceph-3-em-4-carboxylate.

6. The compound of claim 1 which is sodium 7-{D-α-[(4-hydroxy-2-isopropylamino-5-pyrimidinyl)-ureido]-p-hydroxy-phenylacetamido}-3-[(2-methyl-1,3,4-thiadiazol-5-yl)-thiomethyl]-ceph-3-em-4-carboxylate.

7. The compound of claim 1 which is sodium 7-{D-α-[(4-hydroxy-2-isopropylamino-5-pyrimidinyl)-ureido]- p-hydroxyphenylacetamido}-3-[(1-methyl-tetrazol-5-yl)-thiomethyl]-ceph-3-em-4-carboxylate.

8. The compound of claim 1 which is sodium 7-{D-α-[(2-allylamino-4-hydroxy-5-pyrimidinyl)-ureido]-phenylacetamido}-3-[(1-methyl-tetrazol-5-yl)-thiomethyl]-ceph-3-em-4-carboxylate.

9. The compound of claim 1 which is sodium 7-{D-α-[(4-hydroxy-2-(2'-methylallylamino)-5-pyrimidinyl)-ureido]-p-hydroxy-phenylacetamido}-3-[(1-methyl-tetrazol-5-yl)-thiomethyl]-ceph-3-em-4-carboxylate.

10. The compound of claim 1 which is sodium 7-{D-α-[(2-cyclopentylamino-4-hydroxy-5-pyrimidinyl)-ureido]-p-hydroxy-phenylacetamido}-3-[(1-methyl-tetrazol-5-yl)-thiomethyl]-ceph-3-em-4-carboxylate.

11. The compound of claim 1 which is sodium 7-{D-α-[(4-hydroxy-2-(4'-hydroxy-cyclohexylamino)-5-pyrimidinyl)-ureido]-p-hydroxy-phenylacetamido}-3-[(1-methyl-tetrazol-5-yl)-thiomethyl]-ceph-3-em-4-carboxylate.

12. The compound of claim 1 which is sodium 7-{D-α-[(2-p-aminosulfonylanilino-4-hydroxy-5-pyrimidinyl)-ureido]-p-hydroxy-phenylacetamido}-3-[(1-methyl-tetrazol-5-yl)-thiomethyl]-ceph-3-em-4-carboxylate.

13. The compound of claim 1 which is pivaloyloxymethyl 7-{D-α-[(2-p-aminosulfonylanilino-4-hydroxy-5-pyrimidinyl)-ureido]-p-hydroxy-phenylacetamido}-3-[(1-methyl-tetrazol-5-yl)-thiomethyl]-ceph-3-em-4-carboxylate.

14. The compound of claim 1 which is sodium 7-{D-α-[(2-p-methylaminosulfonylanilino-4-hydroxy-5-pyrimidinyl)-ureido]-p-hydroxyphenylacetamido}-3-[(1-methyl-tetrazol-5-yl)-thiomethyl]-ceph-3-em-4-carboxylate.

15. The compound of claim 1 which is sodium 7-{D-α-[(2-p-methylaminosulfonylanilino-4-hydroxy-5-pyrimidinyl)-ureido]-p-hydroxy-phenylacetamido}-3-[(2-methyl-thiadiazol-5-yl)-thiomethyl]-ceph-3-em-4-carboxylate.

16. The compound of claim 1 which is sodium 7-{D-α-[(2-p-methylaminosulfonylanilino-4-hydroxy-5-pyrimidinyl)-ureido]-p-hydroxy-phenylacetamido}-3-[2-methylamino-thiadiazol-5-yl)-thiomethyl]-ceph-3-em-4-carboxylate.

17. The compound of claim 1 which is sodium 7-{D-α-[(2-p-aminosulfonylanilino-4-hydroxy-5-pyrimidinyl)-ureido]-2'-thienylacetamido}-3-[(1-methyltetrazol-5-yl)-thiomethyl]-ceph-3-em-4-carboxylate.

18. An antibiotic pharmaceutical composition consisting essentially of an inert pharmaceutical carrier and an effective antibiotic amount of a compound of claim 1.

19. The method of inhibiting the growth of or destroying pathogenic bacteria in a warm-blooded animal in need thereof, which comprises perorally, parenterally, rectally or topically administering to said animal an effective antibiotic amount of a compound of claim 1.

20. A compound of claim 1, wherein
A is phenyl, p-hydroxyphenyl, 3,4-dihydroxyphenyl, 2-thienyl, 3-thienyl, 2-furyl or 3-furyl;
Y is hydrogen or methoxy;
D is S-Het, where Het is 3-methyl-1,2,4-thiadiazol-5-yl, 1,2,4-thiadiazol-5-yl, 1,3,4-thiadiazol-2-yl, 2-methyl-1,3,4-thiadiazol-5-yl, 2-methylamino-1,3,4-thiadiazol-5-yl, 2-dimethylamino-1,3,4-thiadiazol-5-yl, 2-formylamino-1,3,4-thiadiazol-5-yl, 2-acetylamino-1,3,4-thiadiazol-5-yl, 1-methyl-tetrazol-5-yl, tetrazol-5-yl, 1,2,3-triazol-4-yl, 1,2,4-triazol-3-yl or 2-methyl-1,3,4-oxadiazol-5-yl;
R is hydrogen, cyclopropyl, hydroxyl, methoxy, formylamino, acetylamino, aminocarbonylamino,

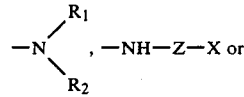
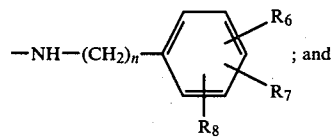

R$_1$, R$_2$, Z, X, R$_6$, R$_7$, R$_8$, n and E have the same meanings as in claim 1,
or, when E is hydrogen, a non-toxic, pharmacologically acceptable salt thereof formed with an inorganic or organic base.

21. A compound of claim 1, wherein
A is phenyl, p-hydroxyphenyl, 2-thienyl, 2-furyl or 3-furyl;
Y is hydrogen or methoxy;
E is hydrogen or pivaloyloxymethyl;
D is S-Het, where Het is tetrazol-5-yl, 1-methyltetrazol-5-yl, 1,3,4-thiadiazol-5-yl or 2-methyl-1,3,4-thiadiazol-5-yl;
R is hydrogen, cyclopropyl, hydroxyl, methoxy, dimethylamino, 4'-hydroxycyclohexyl-amino, acetylamino,

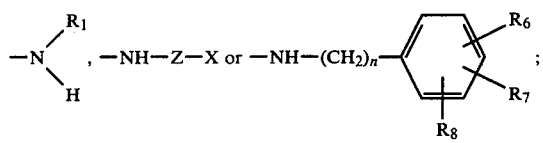

R$_1$ is hydrogen, saturated or unsaturated aliphatic hydrocarbyl of 1 to 4 carbon atoms, or cycloalkyl of 3 to 6 carbon atoms;
Z is ethylene or propylene;
X is hydroxyl, amino, methoxy, ethoxy, mercapto, aminocarbonyl, methylaminocarbonyl, dimethylaminocarbonyl, aminosulfonyl, methylaminosulfonyl, dimethylaminosulfonyl, aminocarbonylamino, methylaminocarbonylamino, methoxycarbonyl, ethoxycarbonyl, methylcarbonyl, ethylcarbonyl, methylmercapto, ethylmercapto, carboxy, methylamino, dimethylamino, formylamino, acetylamino, methylsulfonylamino, acetoxy, methylsulfinyl or methylsulfonyl;
n is 0 or 1; and
one to two of R$_6$, R$_7$ and R$_8$ are hydrogen, chlorine, fluorine, methyl, ethyl, amino, methylamino, dimethylamino, hydroxyl, methoxy, ethoxy, nitro, formylamino, acetylamino, aminocarbonylamino, methylaminocarbonylamino, methylsulfinyl, methylsulfonyl, acetyl, methylcarbonyloxy, methoxycarbonyl, carboxyl, aminocarbonyl, methylaminocarbonyl, dimethylaminocarbonyl, cyano, methylmercapto, methylsulfonylamino, aminosulfonyl, methylaminosulfonyl, dimethylaminosulfonyl or ethylaminosulfonyl, and the remainder of R$_6$, R$_7$ and R$_8$ are hydrogen;

or, when E is hydrogen, a non-toxic, pharmacologically acceptable salt thereof formed with an inorganic or organic base.

22. A compound of claim 1, wherein
R is

R$_6$ is hydrogen, chlorine, hydroxyl, nitro, acetylamino, methylsulfinyl, methylsulfonyl, acetyl, aminocarbonyl, aminocarbonylamino, methylsulfonylamino, aminosulfonyl, methylaminosulfonyl, dimethylaminosulfonyl or ethylaminosulfonyl; and A, Y, D and E have the same meanings as in claim 28; or, when E is hdyrogen, a non-toxic, pharmacologically acceptable salt thereof formed with an inorganic or organic base.

23. A compound of claim 1, wherein
A, Y, D, R, R$_1$, R$_2$, R$_3$, Z, X, R$_4$, R$_5$, R$_6$, R$_7$ and R$_8$ have the same meanings as in claim 1; and
E is benzyl, diphenylmethyl, trityl, tert. butyl, 2,2,2-trichloroethyl, trimethylsilyl, alkanoyloxyalkyl with 1 to 5 carbon atoms in the alkanoyl moiety and 1 to 3 carbon atoms in the alkyl moiety, phthalidyl or indanyl.

24. A compound of claim 1, wherein
A, Y, D, R, R$_1$, R$_2$, R$_3$, Z, X, R$_4$, R$_5$, R$_6$, R$_7$ and R$_8$ have the same meanings as in claim 1; and
E is acetoxymethyl, propionyloxymethyl, 2-acetoxyethyl or pivaloyloxymethyl.

* * * * *

UNITED STATES PATENT AND TRADEMARK OFFICE
CERTIFICATE OF CORRECTION

PATENT NO. : 4,388,315

DATED : June 14, 1983

INVENTOR(S) : BERND WETZEL ET AL.

It is certified that error appears in the above-identified patent and that said Letters Patent is hereby corrected as shown below:

Title page [73]: The assignee's name should read
-- Boehringer Ingelheim GmbH --.

Column 1, line 15, formula I: The portion of the formula which reads "A-CH-CONH" should read
-- A-$\overset{*}{C}$H-CONH --.

Column 3, line 6; Column 66, line 63: "pivaloylox-" should read -- pivaloyloxy- --.

Column 3, line 7; Column 22, line 63; Column 28, line 62; Column 65, line 45; Column 66, line 64: "ymethyl" should read -- methyl --.

Column 7, line 48: "system" should read -- systems --.

Column 13, line 26: "hydrox-" should read -- hydroxy- --.

Column 13, line 27: "ypyrimidines" should read -- pyrimidines --.

Column 22, line 62; Column 28, line 61; Column 65, line 44: "acetox-" should read -- acetoxy- --.

Column 25, lines 26-27: "Example 2 370 from mgm" should read -- Example 2 from 370 mgm --.

Column 26, line 42; Column 41, line 1; Column 54, line 37; Column 58, line 9; Column 63, lines 56 and 60; Column 66, lines 43 and 51: "thi-" should read -- thio- --.

UNITED STATES PATENT AND TRADEMARK OFFICE
CERTIFICATE OF CORRECTION

PATENT NO. : 4,388,315
DATED : June 14, 1983
INVENTOR(S) : BERND WETZEL ET AL.

It is certified that error appears in the above-identified patent and that said Letters Patent is hereby corrected as shown below:

Column 26, line 43; Column 41, line 2; Column 54, line 38; Column 58, line 10; Column 63, lines 57 and 61; Column 66, lines 44 and 52:

"omethyl" should read -- methyl --.

Column 32, Example 30 (column of NMR spectrum): "4.05 (d, 1H)" should read -- 4.95 (d, 1H) --.

Column 42, line 6: Delete "b".

Column 44, line 13: "2.05 mols" should read -- 2.05 mmols --.

Column 44, lines 28-38: The portion of the structural formula which reads " 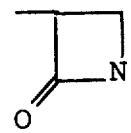 "

should read -- 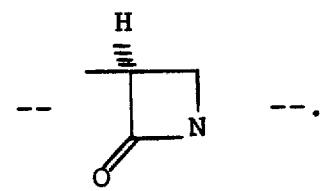 --.

Column 50, Example 81 (column for NMR spectrum):
"3.2-3.6 (m, 3H)" should read
-- 3.2-3.6 (m, 6H) --.

Column 50, Example 83 (column for NMR spectrum):
"3.93 (s, 3H)" should read
-- 3.95 (s, 3H) --.

UNITED STATES PATENT AND TRADEMARK OFFICE
CERTIFICATE OF CORRECTION

PATENT NO. : 4,388,315   Page 3 of 3
DATED      : June 14, 1983
INVENTOR(S) : BERND WETZEL ET AL.

It is certified that error appears in the above-identified patent and that said Letters Patent is hereby corrected as shown below:

Column 52, Example 89 (column for NMR spectrum):
  "4.85 (q,1H + s, 1H)" should read
  -- 4.85 (q, 2H + s, 1H) --.

Column 55, line 20: "dihydrox-" should read -- dihydroxy- --.

Column 55, line 21: "ypyrimidine" should read -- pyrimidine --.

Column 58, line 12: "phenylacetamino" should read
  -- phenylacetamido --.

Column 58, line 16" "hydroxyphenylacetamido" should read
  -- hydroxyphenylacetamino --.

Column 58, line 63; Column 59, line 23: "Sodium 7-}D-"
  should read -- Sodium 7-{D- --.

Column 61, line 63: "5pyrimidinyl" should read
  -- 5-pyrimidinyl --.

Column 110, line 4 of claim 4: "2-em-4-carboxylate" should
  read -- 3-em-4-carboxylate --.

Signed and Sealed this

Twenty-first Day of February 1984

[SEAL]

Attest:

GERALD J. MOSSINGHOFF

Attesting Officer   Commissioner of Patents and Trademarks